United States Patent
Ji et al.

(10) Patent No.: US 11,389,483 B2
(45) Date of Patent: Jul. 19, 2022

(54) METHODS FOR TREATING PAIN

(71) Applicant: Duke University, Durham, NC (US)

(72) Inventors: Ru-Rong Ji, Durham, NC (US); Gang Chen, Durham, NC (US)

(73) Assignee: Duke University, Durham, NC (US)

( * ) Notice: Subject to any disclaimer, the term of this patent is extended or adjusted under 35 U.S.C. 154(b) by 526 days.

(21) Appl. No.: 15/743,208

(22) PCT Filed: Jul. 8, 2016

(86) PCT No.: PCT/US2016/041655
§ 371 (c)(1),
(2) Date: Jan. 9, 2018

(87) PCT Pub. No.: WO2017/011352
PCT Pub. Date: Jan. 19, 2017

(65) Prior Publication Data
US 2019/0117697 A1    Apr. 25, 2019

Related U.S. Application Data

(60) Provisional application No. 62/190,953, filed on Jul. 10, 2015.

(51) Int. Cl.
*A61K 35/28* (2015.01)
*A61K 38/18* (2006.01)
*A61P 29/00* (2006.01)
*A61K 9/00* (2006.01)

(52) U.S. Cl.
CPC ............ *A61K 35/28* (2013.01); *A61K 9/0019* (2013.01); *A61K 38/1841* (2013.01); *A61P 29/00* (2018.01)

(58) Field of Classification Search
CPC .. A61K 35/28; A61K 38/1841; A61K 9/0019; A61P 29/00
See application file for complete search history.

(56) References Cited

U.S. PATENT DOCUMENTS

| | | | |
|---|---|---|---|
| 4,554,101 A | 11/1985 | Hopp | |
| 2002/0001826 A1 | 1/2002 | Wager et al. | |
| 2005/0152905 A1 | 7/2005 | Omoigui | |
| 2012/0076759 A1 | 3/2012 | Li et al. | |
| 2012/0115224 A1 | 5/2012 | Ochiai et al. | |

FOREIGN PATENT DOCUMENTS

| | | |
|---|---|---|
| CN | 1187773 A | 7/1998 |
| CN | 1683004 A | 10/2005 |
| CN | 105274055 A | 1/2016 |

OTHER PUBLICATIONS

Chen et al., J Clin Invest. 2015;125(8):3226-3240.*
Musolino et al., Neuroscience Letters 41 8 (2007) 97-101.*
Echeverry et al., Molecular Pain 2009, 5:16.*
Oh et al., Stem Cells Translational Medicine, 4: 590-597, 2015, published online May 1, 2015.*
"Amyotrophic Lateral Sclerosis (ALS) Fact Sheet", NINDS, Publication date Jun. 2013, NIH Publication No. 16-916, pp. 1-12.*
Zhang et al., Korean J. Pain, 27(3): 239-245, Jul. 2014.*
Zhang et al., European Review for Medical and Pharmacological Sciences, 20: 899-905, 2016.*
Zhang L., Chan C. (2010). Isolation and Enrichment of Rat Mesenchymal Stem Cells (MSCs) and Separation of Single-colony Derived MSCs. JoVE. 37: 1-4.*
Tencerova et al., Frontiers in Endocrinology, 7, Article 127: 1-12, 2016.*
Guo et al., "Bone Marrow Stromal Cells Produce Long-Term Pain Relief in Rat Models of Persistent Pain," Stem Cels Translational and Clinical Research; 29:1294-1303 (2011) www.StemCells.com.
Knerlich-Lukoschus et al., "Spatiotemporal CCRI, CCL3(MIP-la), CXCR4, CXCL12(SDF-la) expression patterns in a rat spinal cord in jury model of posttraumatic neuropathic pain," laboratory investigation, J Neurosurg Spine 14:583-597 (2011).
PCT/US2016/41655 International Search Report and Written Opinion of the International Searching Authority dated Oct. 4, 2016 (9 pages).
Kyte et al., "A Simple Method for Displaying the Hydropathic Character of a Protein," J. Mol. Biol., 1982, 157:105-132.
Bennett et al., "A Distinct Subgroup of Small DRG Cells Express GDNF Receptor Components and GDNF Is Protective for These Neurons after Nerve Injury," J. Neurosci., 1998, 18:3059-3072.
Decosterd et al., "Spared nerve injury: an animal model of persistent peripheral neuropathic pain," Pain, 2000, 87:149-158.
Hylden et al., "Intrathecal morphine in mice: a new technique," Eur. J. Pharmacol., 1980, 67:313-316.
Kawasaki et al., "Distinct roles of matrix metalloproteases in the early- and late-phase development of neuropathic pain," Nat. Med , 2008, 14:331-336.
Berta et al., "Extracellular caspase-6 drives murine inflammatory pain via microglial TNF-α secretion," J. Clin. Invest., 2014, 124:1173-1186.
Xu et al., "Neuroprotectin/Protectin D1 protects neuropathic pain in mice after nerve trauma," Ann. Neurol., 2013, 74:490-495.
Lee et al., "A monoclonal antibody that targets a NaV1.7 channel voltage sensor for pain and itch relief," Cell, 2014, 157:1393-1404.
King et al., "Unmasking the tonic-aversive state in neuropathic pain," Nat. Neurosci., 2009, 12:1364-1366.
Morris et al., "Phase 1 Study of GC1008 (Fresolimumab): A Human Anti-Transforming Growth Factor-Beat (TGFbeta) Monoclonal Melanoma or Renal Cell Carcinoma", PLOS One, 2014, vol. 9, Issue 3, e90353, 11 pages.

(Continued)

*Primary Examiner* — Ralph J Gitomer
(74) *Attorney, Agent, or Firm* — Michael Best & Friedrich LLP

(57) ABSTRACT

Disclosed herein are bone marrow stromal cells. The bone marrow stromal cells may express and/or secrete TGF-β1. The bone marrow stromal cells may express CXCR4. Also disclosed herein is a method of treating pain in a subject in need thereof. The method of treating may include administration of the bone marrow stromal cells to the subject. The pain may be neuropathic pain.

22 Claims, 40 Drawing Sheets

(56) References Cited

OTHER PUBLICATIONS

Chinese Patent Office Action for Application No. 201680052435.8 dated Aug. 4, 2020 (40 pages).
Salazar et al., "Mesenchymal stem cells produce Wnt isoforms and TGF-β1 that mediate proliferation and procollagen expression by lung fibroblasts," Am J Physiol Lung Cell Mol Physiol, 2009,c297: L1002-L1011.
Qian et al., "Short-term Exposure of Mesenchymal Stem Cells to TGF-β1 Increases Expression of CXCR4 and Migratory Capacity of the Cells in vitro," Acta Med Univ Sci Technol Huazhong, 2012, 41(5): 523-528.
Jiang Dengchuan et al., "Peripheral Mechanism of Nerve Injury Pain," Basis and Clinic of Pain, Fudan University Press, published on Jul. 30, 2001, p. 18.
Chinese Patent Office Action for Application No. 201680052435.8 dated Mar. 26, 2021 (27 pages, English translation included).
Chinese Patent Office Action for Application No. 201680052435.8 dated Feb. 15, 2022 (19 pages, English translation included).

\* cited by examiner

METHODS FOR TREATING PAIN

CROSS REFERENCE TO RELATED APPLICATIONS

This application claims priority to U.S. Provisional Application No. 62/190,953, filed on Jul. 10, 2015, which is incorporated herein by reference in its entirety.

STATEMENT OF GOVERNMENT INTEREST

This invention was made with government support under grants R01-DE17794, R01-NS87988, R01-NS67686, R01-NS89479, and R01-DE22743 awarded by the United States National Institutes of Health. The government has certain rights in the invention.

TECHNICAL FIELD

This Disclosure Relates to Bone Marrow Stromal Cells and Methods for Treating Pain.

BACKGROUND

Disease and injury may give rise to pain in a subject. One type of pain is neuropathic pain, which may be triggered by multiple insults to the nervous system. Pathogenesis of neuropathic pain is complex, involving structural and neurophysiological changes throughout the neuroaxis, from the site of peripheral nerve injury to the cell bodies (primary sensory neurons) in dorsal root ganglia (DRGs) and to the spinal cord and/or brain. As such, treatment of neuropathic pain is a clinical challenge.

Presently, no drugs are available that treat neuropathic pain in a complete and definitive way. Rather, present therapies focus on suppression of nerve impulse propagation or inhibition of synaptic transmission to provide limited pain relief and often undesirable side effects. Additionally, systemic injection of bone marrow stromal cells (BMSCs) may alleviate inflammatory and neuropathic pain, but pain relief may be short-lived. The BMSCs are short-lived after systemic administration to a subject (e.g., 2-3 days) and do not necessarily localize at the site of inflammatory and/or neuropathic pain.

Accordingly, a need exists in the art for the identification of therapies for treating pain, including neuropathic pain, and effective routes of administration for such therapies.

SUMMARY

The present invention relates to a method of treating pain in a subject in need thereof. The method may comprise administering to the subject a composition comprising bone marrow stromal cells (BMSCs). The composition may further comprise TGF-β1. The composition may be administered by injection. The composition may be injected intrathecally. The composition may be injected directly into the dorsal root ganglia. The pain may comprise neuropathic pain, inflammatory pain, cancer pain, or a combination thereof. The pain may be chronic. The pain may be reduced or suppressed in the subject for at least about 30 minutes, at least about 12 hours, at least about 7 days, at least about 2 weeks, or at least about 6 months. The subject may be mammalian. The subject may be human. The BMSCs may be autologous BMSCs, heterologous BMSCs, or a combination thereof. The BMSCs may be derived from a cell line, a donor subject, or a combination thereof. The method may comprise the administration of $0.5 \times 10^5$ to about $5.0 \times 10^7$ BMSCs to the subject. The BMSCs may secrete TGF-β1. The BMSCs may express CXCR4. The BMSCs may secrete TGF-β1 and express CXCR4. The BMSCs may be targeted to one or more injured neurons, inflamed dorsal root ganglia (DRGs), or a combination thereof. The BMSCs may be targeted to one or more dorsal root ganglia (DRGs) with injured axons, inflamed DRGs, or a combination thereof. The method may comprise protecting the axons of the subject from injury. After administration of the composition, the BMSCs may migrate to dorsal root ganglions (DRGs) expressing CXCL12. After migration, the BMSCs may be localized at an edge or surrounding membrane of the dorsal root ganglia (DRGs), spinal cord, or a combination thereof. After administration of the composition, the BMSCs may be present in the subject for at least about 1 day, at least about 1 week, or at least about 1 month. The BMSCs may be tolerated by an immune system of the subject. The method may further comprise administering to the subject a composition comprising TGF-β1. The composition comprising TGF-β1 may be administered by injection. The composition comprising TGF-β1 may be administered by intrathecal injection. The composition comprising TGF-β1 may be administered by direct injection into the dorsal root ganglia.

Statistical significance was determined by one-way ANOVA followed by Bonferroni post-hoc test. All data are expressed as mean±S.E.M.

Figure 4:
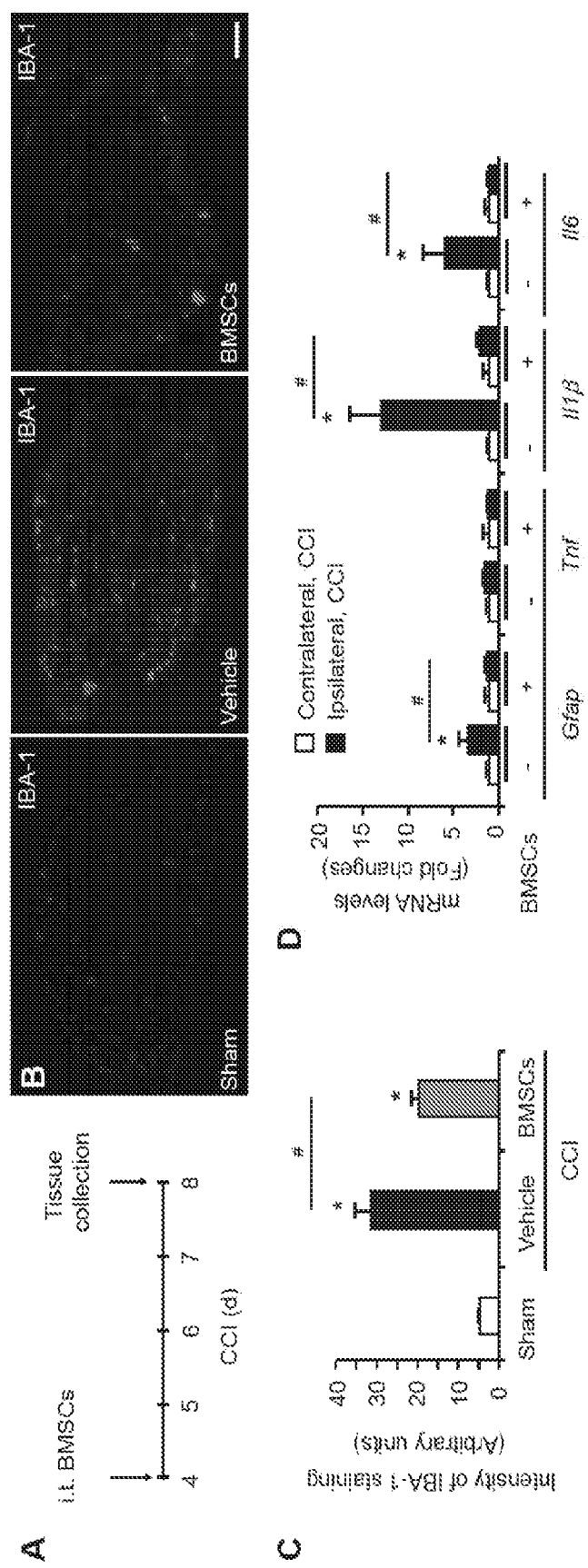
Figure 4:
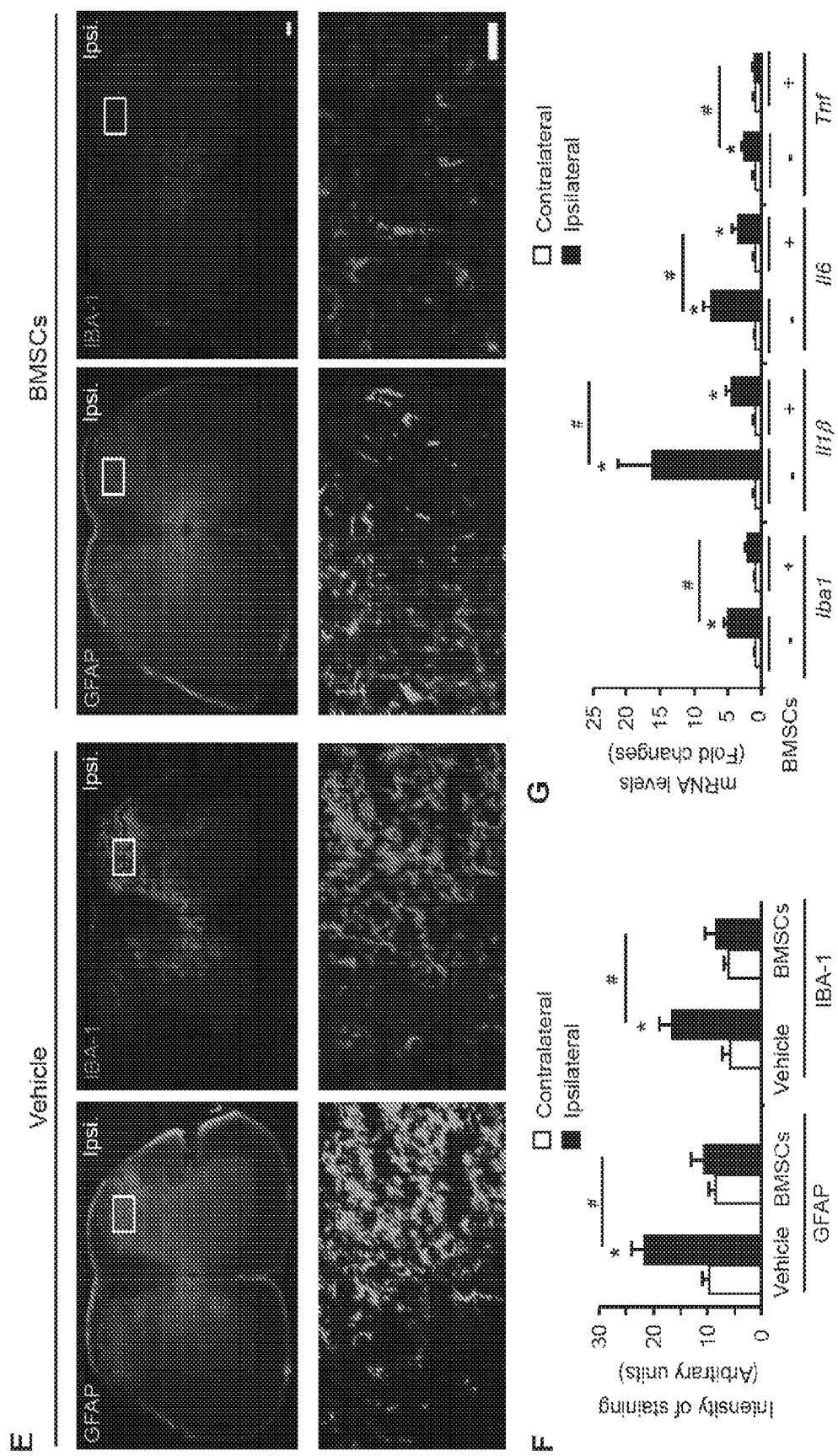

FIG. 4 shows that intrathecal administration of BMSCs inhibits CCI-induced glial activation and neuroinflammation in lumbar DRG and spinal cord dorsal horn. (A) Paradigm showing the time of BMSCs treatment (CCI-4 d) and tissue collection (CCI-8 d). (B) Inhibition of CCI-induced upregulations of macrophage marker IBA-1 in L4-L5 DRGs by BMSCs (i.t., $2.5 \times 10^5$ cells). Scale, 50 (C) Quantification of IBA-1 staining. *P<0.05, compared with sham group; #P<0.05. n=4 mice/group. (D) Real-time RT-PCR showing the expression levels of Gfap, Il1β, Il6, and Tnf mRNAs in L4-L5 DRGs and the effects of BMSCs. *P<0.05, compared to contralateral group; #P<0.05, n=4 mice/group. (E and F) Inhibition of CCI-induced upregulations of microglial marker IBA-1 and astrocyte marker GFAP in L4-L5 dorsal horn by BMSCs. F was quantification of GFAP and IBA-1 staining. Scale, 200 μm (up panel) and 50 μm (low panel). Low panels are enlarged images of up panels. *P<0.05, compared with contralateral group; #P<0.05, n=4 mice/group. (G) Real-time RT-PCR showing the expression levels of Iba1, Il1β, Il6 and Tnf mRNAs and the effects of BMSCs. *P<0.05, compared to contralateral group; #P<0.05, n=4-5 mice/group. Statistical significance was determined by one-way ANOVA followed by Bonferroni post-hoc test. All data are expressed as mean±S.E.M.

Figure 5:
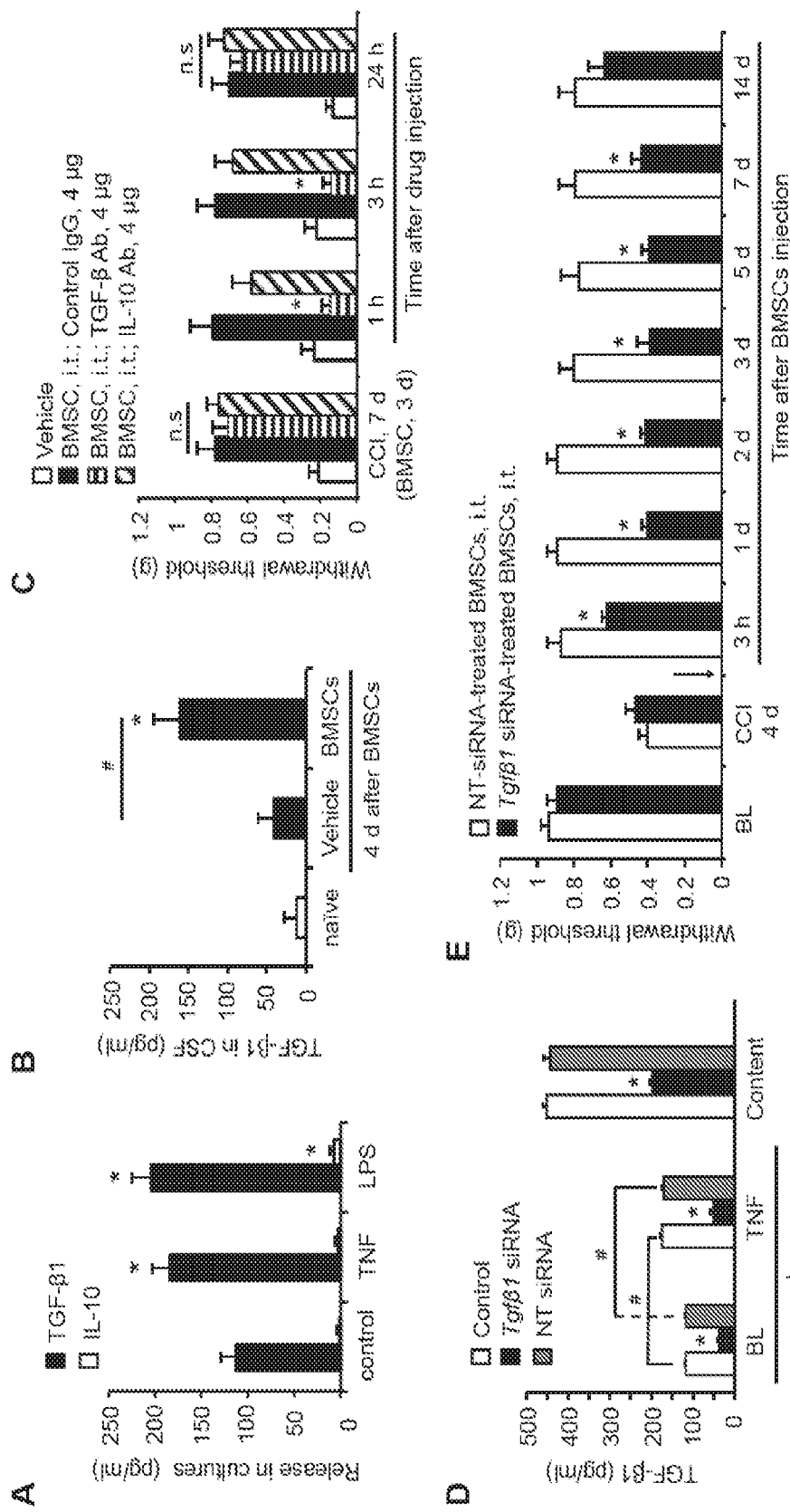
Figure 5:
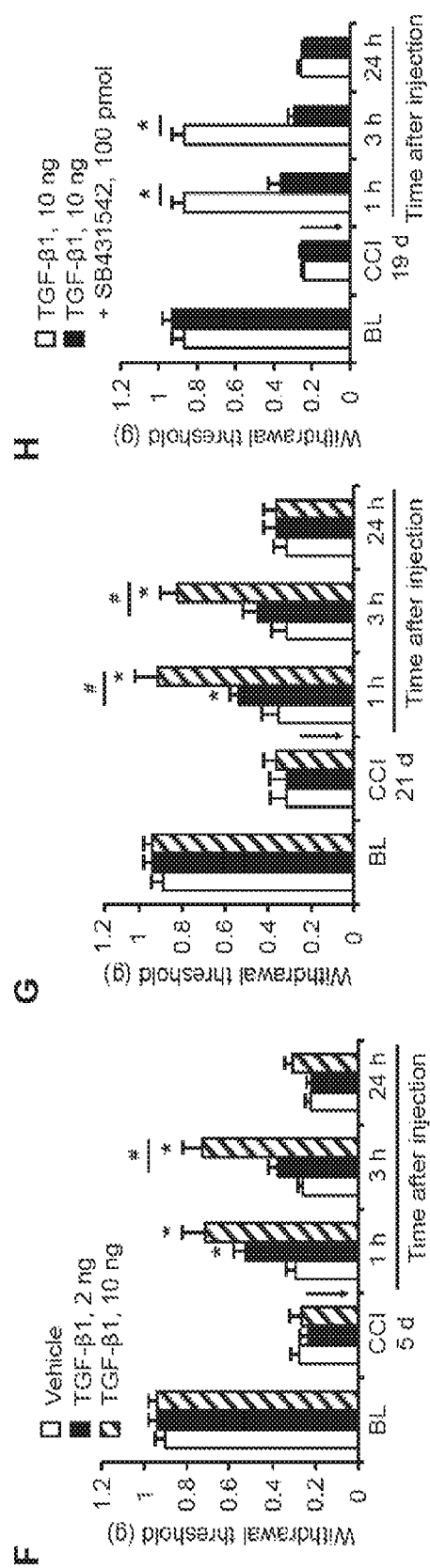

FIG. 5 shows that BMSCs release TGF-β1 to inhibit neuropathic pain in CCI mice. (A) ELISA analysis showing TGF-β1 and IL-10 release in BMSCs culture medium and the effects of TNF (10 ng/mL, 60 min) and LPS (100 ng/mL, 60 min) on the release. *P<0.05, compared with respective control group. n=8 separate cultures from different mice. (B) ELISA analysis showing increased TGF-β1 release in CSF 8 d after CCI and 4 d after intrathecal $2.5 \times 10^5$ BMSCs. *P<0.05, compared with naïve and vehicle; #P<0.05. n=4 mice/group. (C) Reversal of BMSCs-induced inhibition of mechanical allodynia by TGF-β1 neutralizing antibody (4 μg, i.t.) but not by IL-10 neutralizing antibody (4 μg, i.t.) and control IgG (4 μg, i.t.). n.s., no significance; *P<0.05, compared with control IgG group; n=5 mice/group. (D) Reduction of TGF-β1 release and expression in BMSCs by the Tgfβ1 siRNA treatment (1 μg/mL, 18 h). Both baseline (BL) release and evoked release by TNF (10 ng/mL, 1 h) were measured. *P<0.05, compared with non-targeting siRNA; #P<0.05. n=4 separate cultures from different mice. (E) Anti-allodynic effect of BMSCs ($2.5 \times 10^5$) is compromised by pre-treatment of BMSCs with Tgfβ1 siRNA (1 μg/mL for 18 h) but not non-targeting control siRNA. Arrow indicates the time of the BMSCs injection. *P<0.05, compared with non-targeting siRNA control. n=5 mice/group. (F and G) Dose-dependent reversal of mechanical allodynia by intrathecal TGF-β1 at 5 and 21 d after CCI. *P<0.05, compared with vehicle group; #P<0.05, n=5 mice/group. (H) TGF-βR1 inhibitor SB431542 (100 pmol, i.t.) completely blocks the anti-allodynic effect of TGF-β1 (10 ng, i.t.). Arrow indicates i.t. injection 19 d after CCI. *P<0.05, n=4-5 mice/group. Statistical significance was determined by one-way ANOVA (A, B, D), 2-way ANOVA followed by Bonferroni post-hoc test (C, E, F, G, H) or Student's t test (E, H). All data are expressed as mean±S.E.M.

Figure 6:
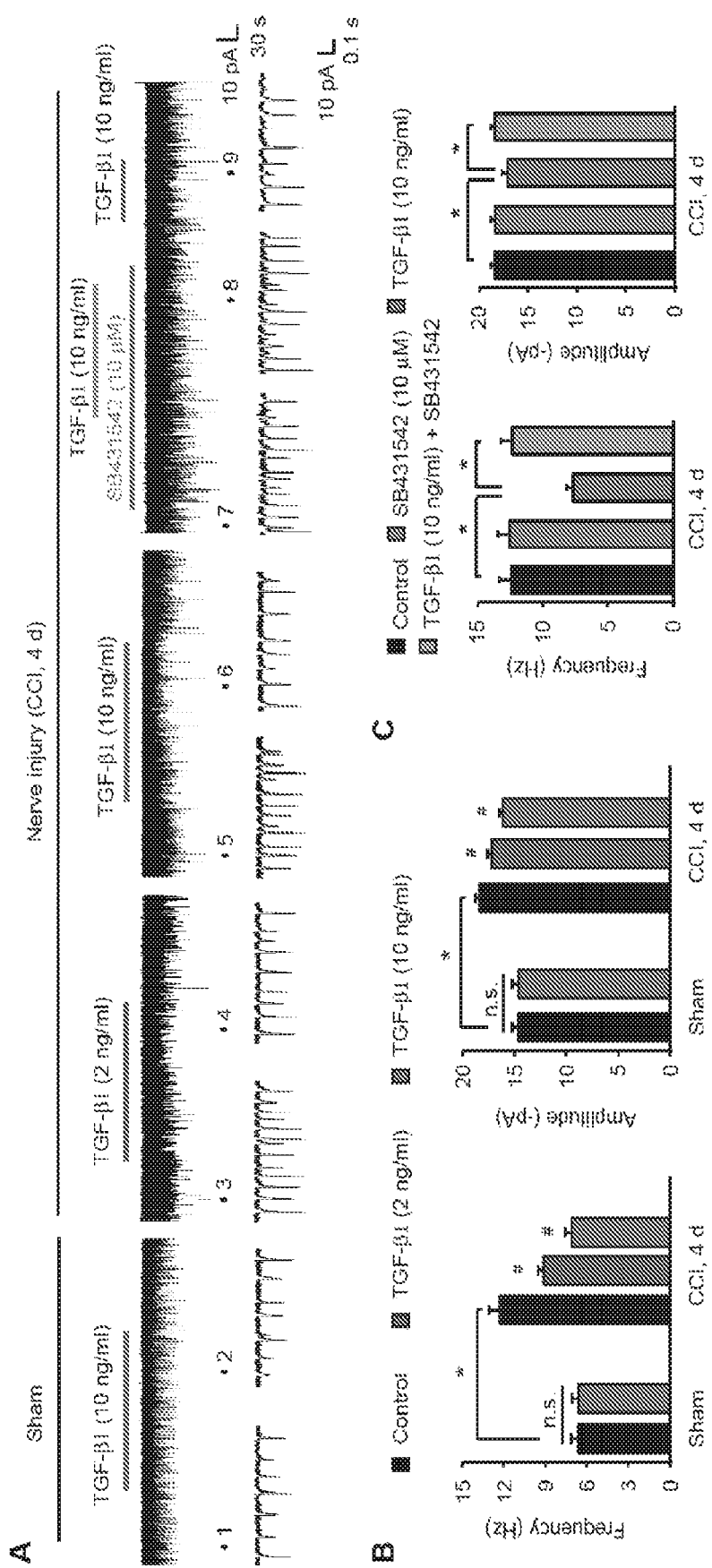

FIG. 6 shows that exogenous TGF-β1 rapidly suppresses CCI-induced enhancement of excitatory synaptic transmission in lamina IIo neurons of spinal cord slices via TGF-β1R. (A) Traces of spontaneous excitatory postsynaptic currents (sEPSCs) in lamina IIo neurons of spinal cord slices. (B) Frequency and amplitude of sEPSCs. CCI (4 d) induces profound increases in sEPSC frequency and amplitude, which are suppressed by TGF-β1 (2 or 10 ng/mL). Note that TGF-β1 has no effects on the frequency and amplitudes of sEPSCs in sham control spinal cord. n.s., no significance; *P<0.05, compared with sham surgery; #P<0.05, compared with control group, n=5 neurons/group. (C) TGF-β1 receptor (TGF-β1R) antagonist SB431542 blocks TGF-β1-induced inhibition of sEPSC frequency and amplitude. *P<0.05, n=5 neurons/group. Statistical significance was determined by one-way ANOVA followed by Bonferroni post-hoc test. All data are expressed as mean±S.E.M.

Figure 7:
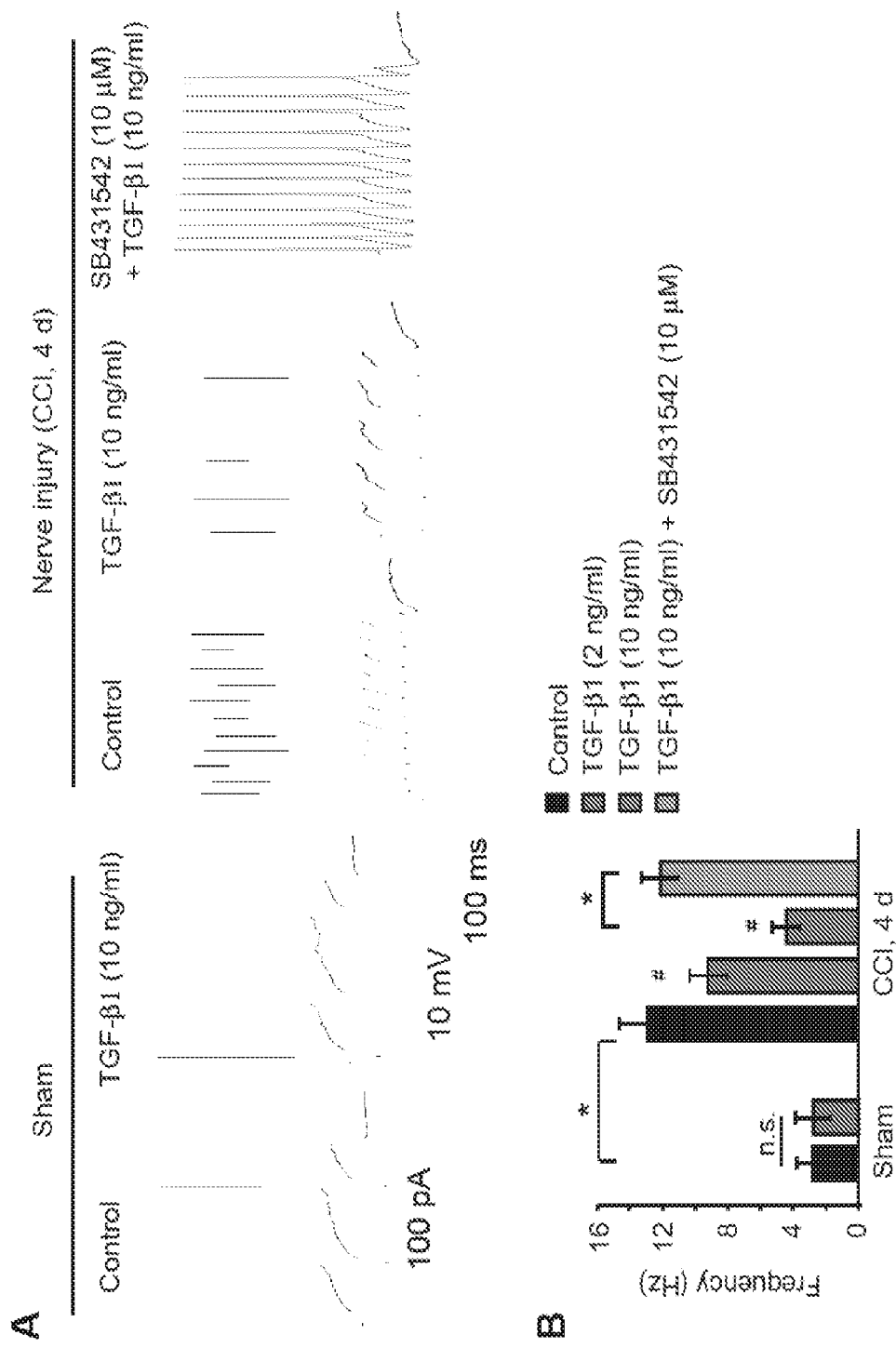

FIG. 7 shows that exogenous TGF-β1 blocks CCI-induced increases in action potential frequency in whole mount DRG via TGF-β1R. (A) Traces of evoked action potentials in small-sized neurons of whole mount DRGs of sham and CCI mice. (B) Frequency of action potentials and the effects of CCI, TGF-β1, and SB431542. Note that the CCI-induced increase in action potential frequency is suppressed by TGF-β1 (2 or 10 ng/mL) and this suppression is abrogated by SB431542. n.s., no significance; *P<0.05; #P<0.05, compared with CCI-control; one-way ANOVA followed by Bonferroni post-hoc test. n=5 neurons/group. All data are expressed as mean±S.E.M.

Figure 8:
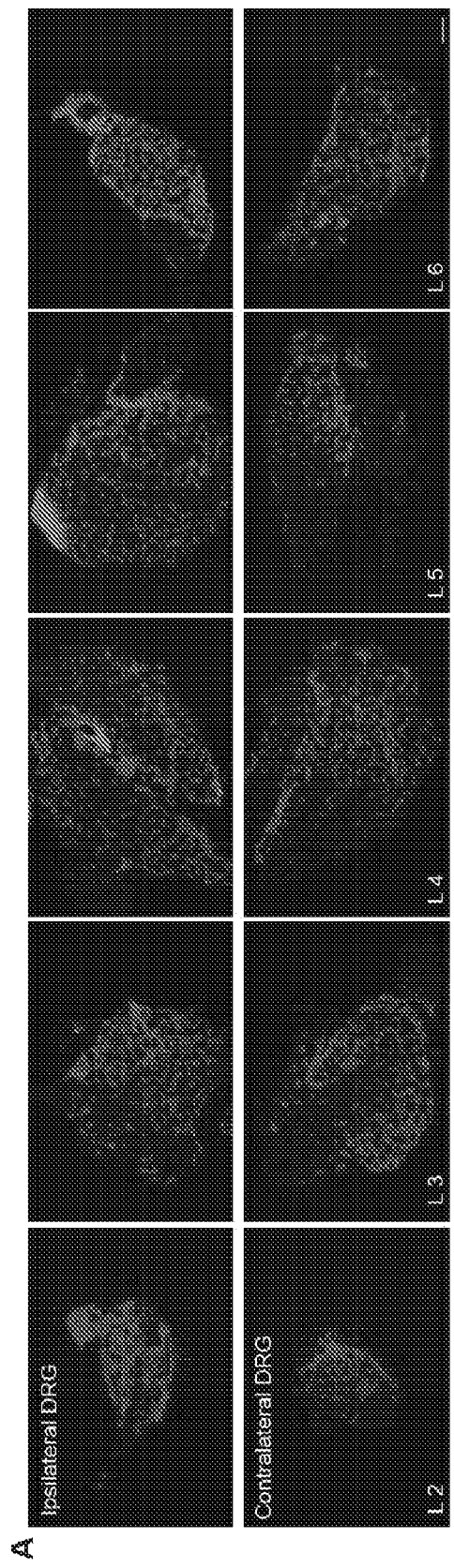
Figure 8:
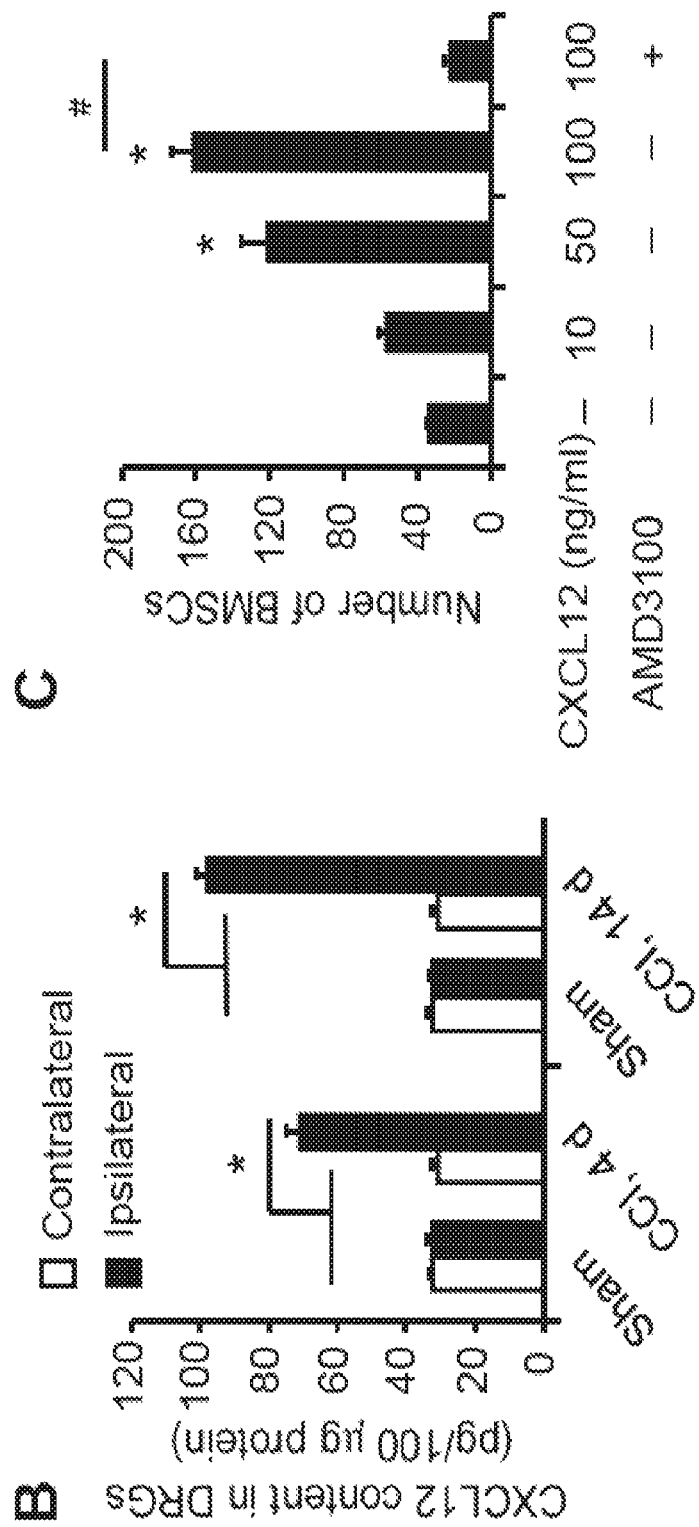
Figure 8:
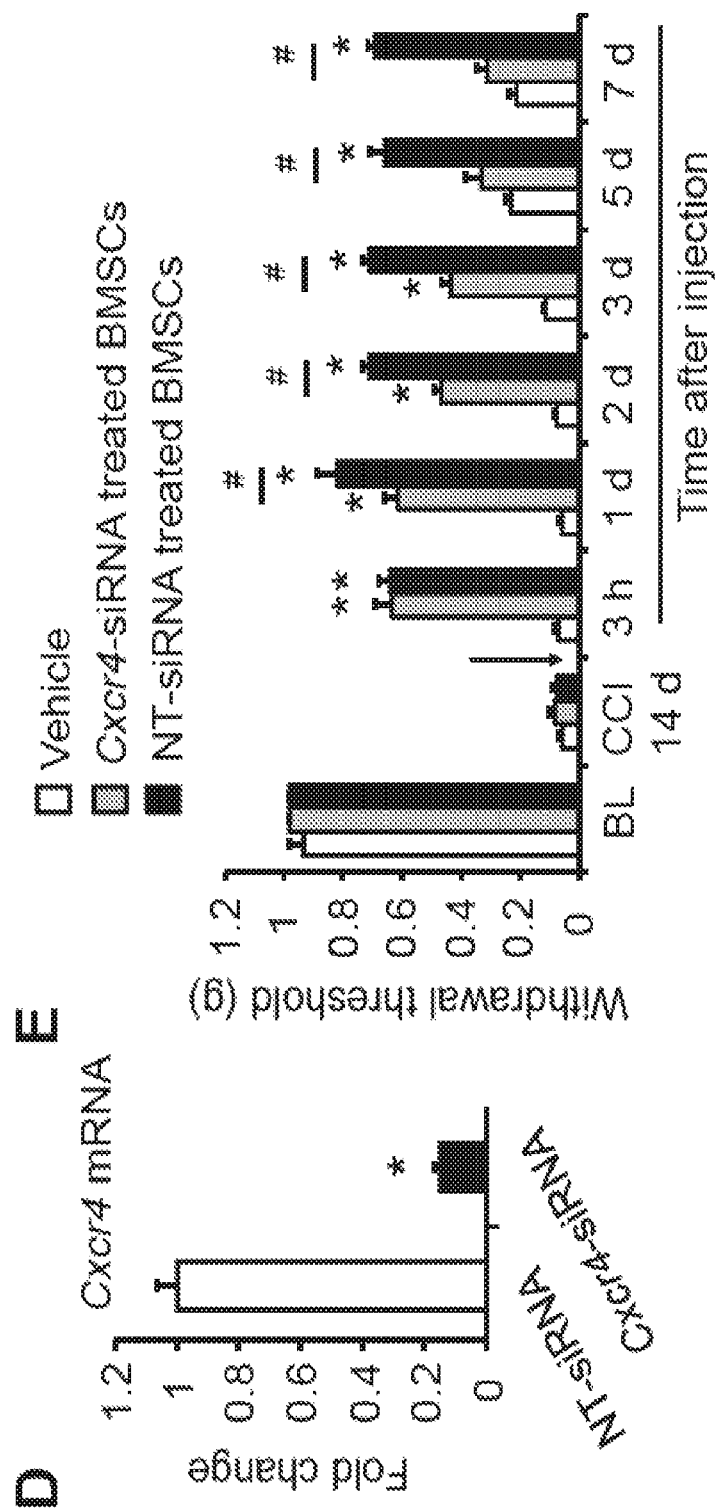
Figure 8:
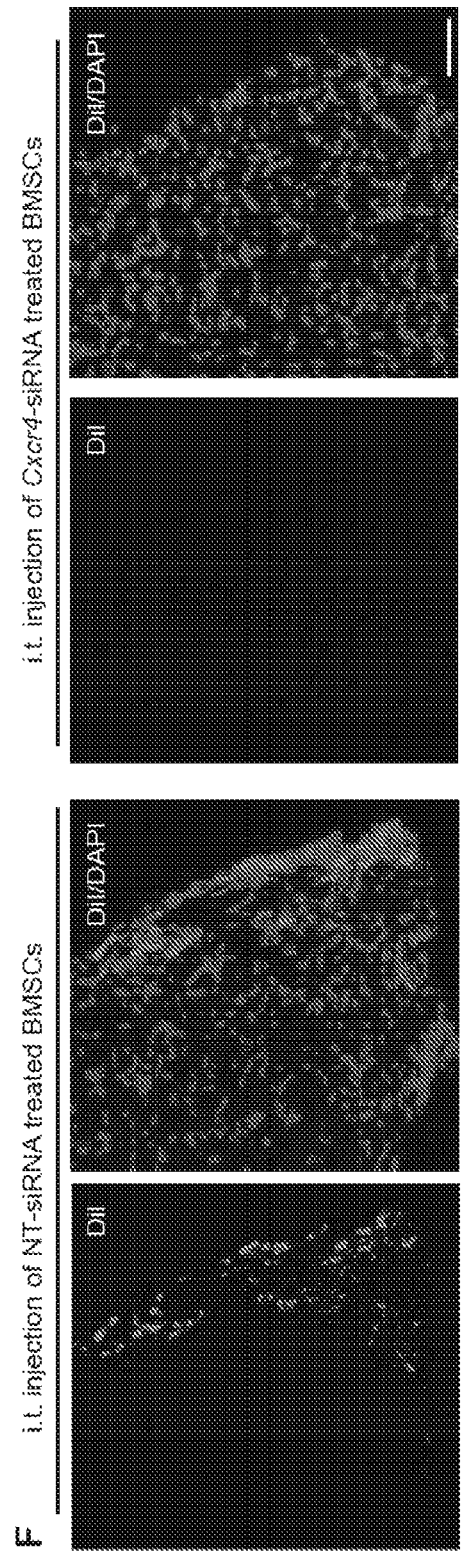
Figure 8:
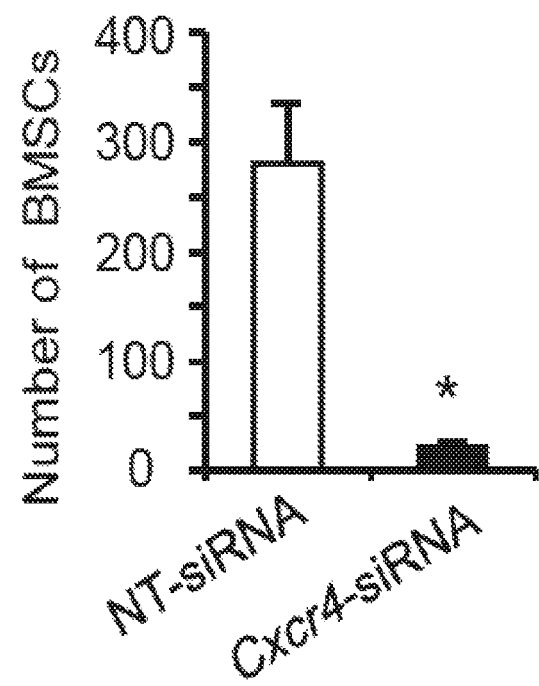

FIG. 8 shows that CXCL12-CXCR4 axis controls BMSCs migration to lumbar DRGs and mediates BMSCs' anti-allodynic effect in CCI mice. (A) Selective targeting of intrathecally injected BMSCs (CM-Dil labeled) to the ipsilateral L4-L6 DRGs 3 d after i.t. injection (CCI-7 d). Scale, 100 μm. Note there is only limited migration of BMSCs to contralateral DRGs. (B) ELISA analysis showing CXCL12 expression in contralateral and ipsilateral L4-L6 DRGs 4 and 14 d after CCI. *P<0.05, n=4 mice/group. (C) Chemotaxis (transwell invasion) assay showing the migration of BMSCs in response to CXCL12 (0-100 ng/ml) and the inhibitory effect of CXCR4 antagonist AMD3100 (5 mg/L 30 min). *P<0.05, compared with control group (no treatment); #P<0.05, n=4 wells from separate cultures. (D) Reduction of Cxcr4 mRNA levels in BMSCs treated with Cxcr4-siRNA (1 μg/mLl, 18 h). *P<0.05, n=3 separate cultures. (E) Anti-allodynic effect of i.t. BMSCs ($2.5 \times 10^5$ cells) was compromised by pre-treatment of BMSCs with Cxcr4 siRNA but not with non-targeting (NT) control siRNA. Arrow indicates BMSC injection on CCI-14 d. *P<0.05, compared with vehicle group, #P<0.05; n=5 mice/group. (F) Migration of CM-Dil labeled BMSCs to the ipsilateral L5-DRG 7 d after i.t. injection (CCI-21 d). Note this migration is blocked by Cxcr4 siRNA. Scale, 50 μm. (G) Number of CM-Dil-labeled BMSCs in ipsilateral L4-L6 DRGs after treatment in F. *P<0.05, n=5 mice/group. Statistical significance was determined by one-way ANOVA followed by Bonferroni post-hoc test (B and C), 2-way repeated-measures ANOVA followed by Bonferroni post-hoc test (E) or Student's t test (D and G). All data are expressed as mean±S.E.M.

Figure 9:
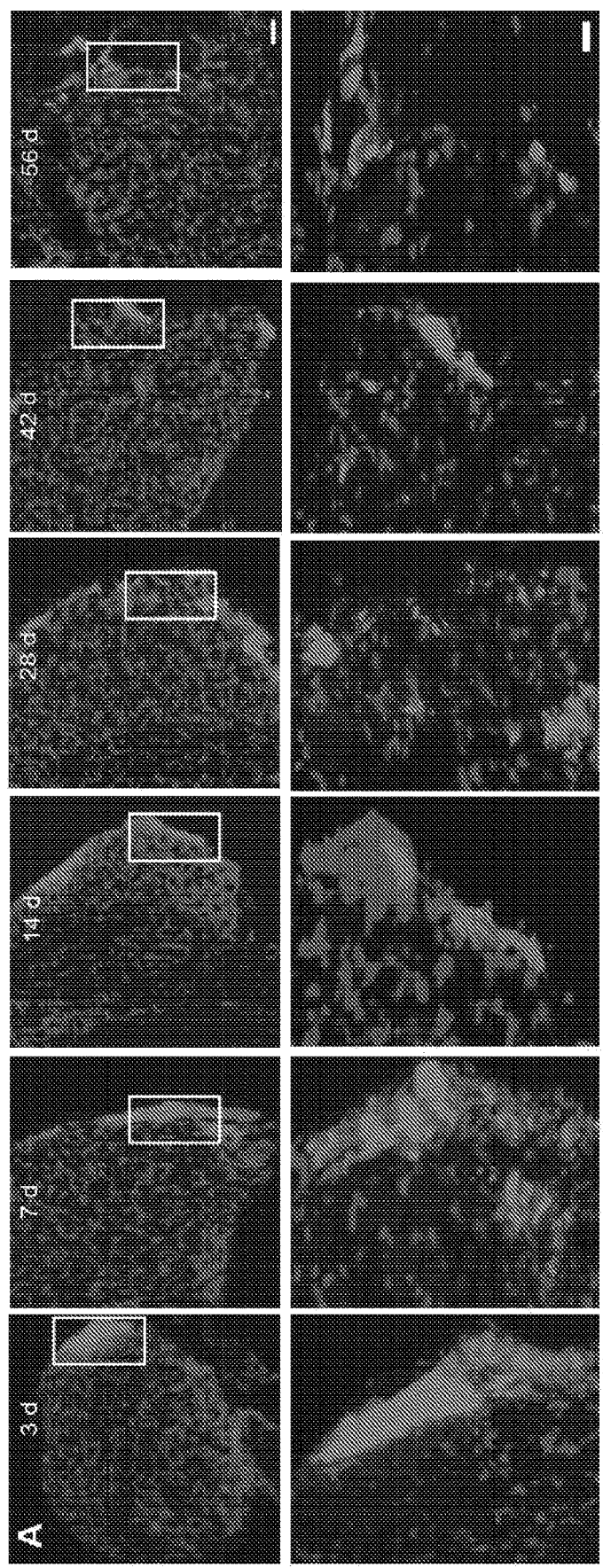
Figure 9:
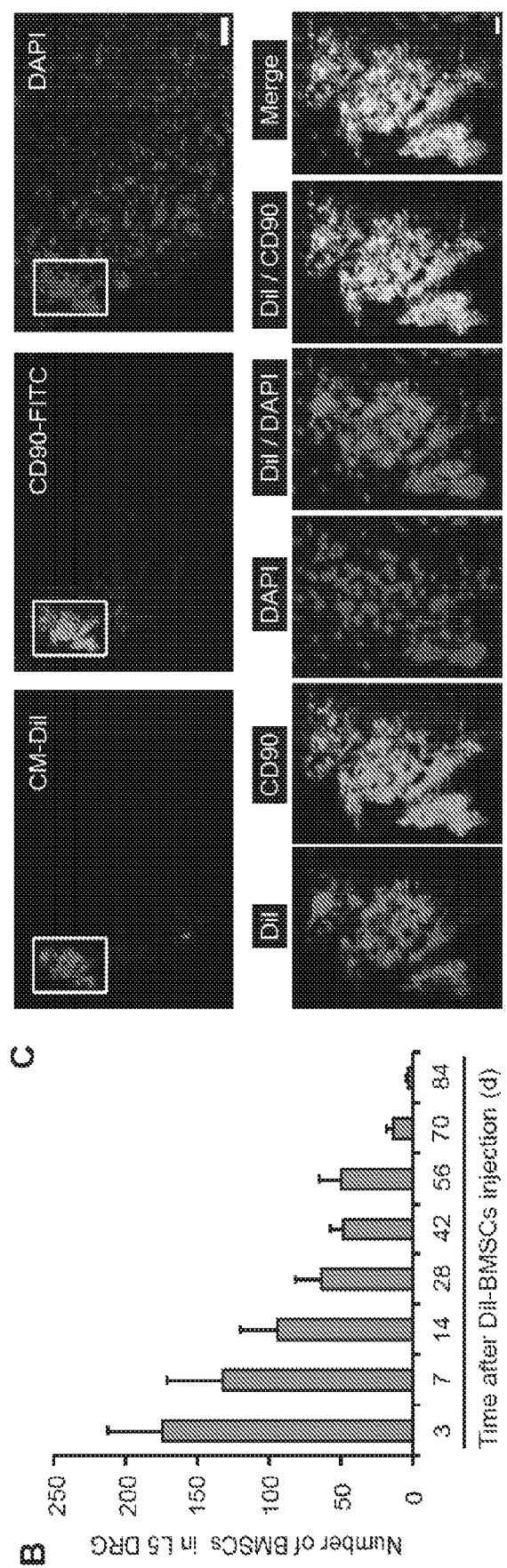

FIG. 9 shows that long-term survival of CM-Dil labeled BMSCs in ipsilateral L5-DRGs following intrathecal injection in CCI mice. (A) Localization of CM-Dil labeled BMSCs to the ipsilateral L5-DRG at 3-56 days after intrathecal injection. Scale, 50 μm (up panel) and 10 μm (low panel). Low panels are enlarged images of up panels. Note that BMSCs are mainly localized on the edges of DRGs. (B) Number of CM-Dil labeled BMSCs in L5 DRGs 3-84 d after i.t. BMSCs injection, given 4 days after CCI. n=4 mice per group. (C) CM-Dil labeled BMSCs express the stem cell marker CD90 in L5 DRG 28 d after the BMSCs injection.

Low panels are high magnification merged images of up panels. Scale, 50 μm (up) and 10 μm (low).

Figure 10:
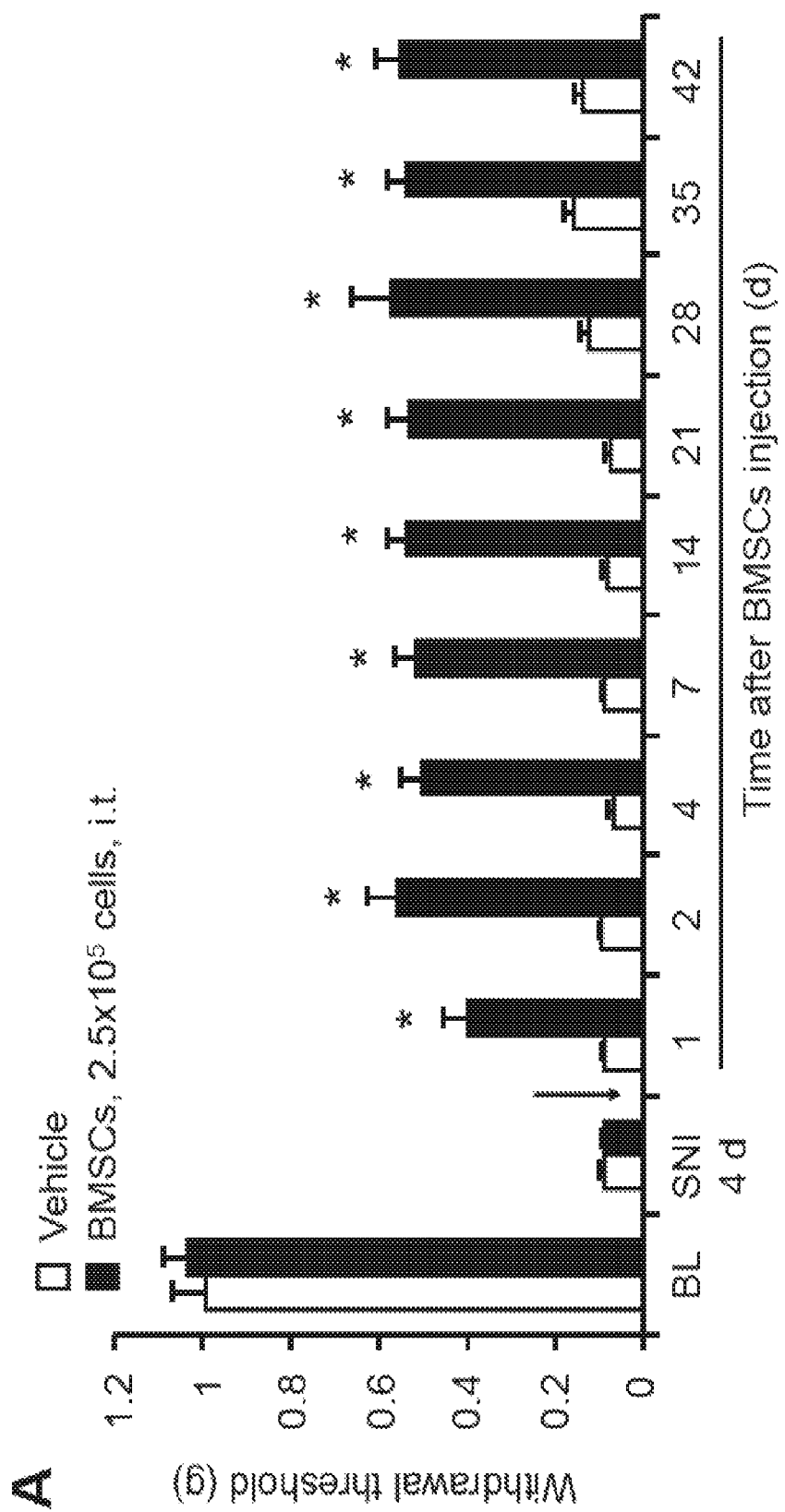
Figure 10:
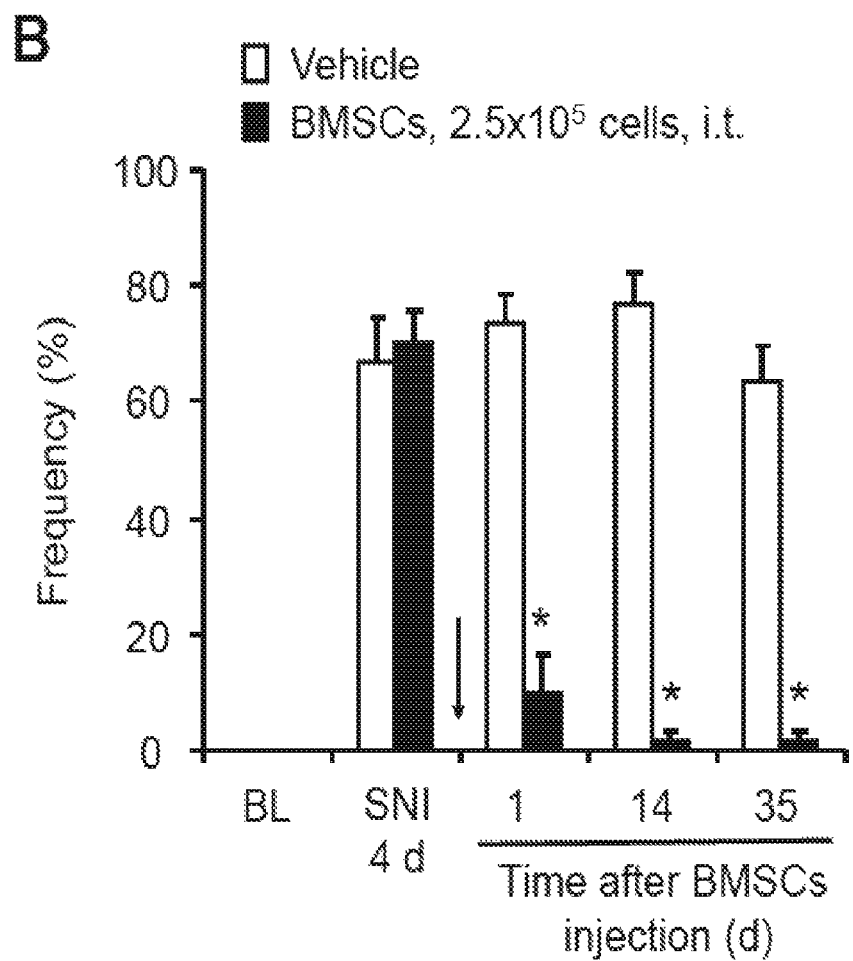
Figure 10:
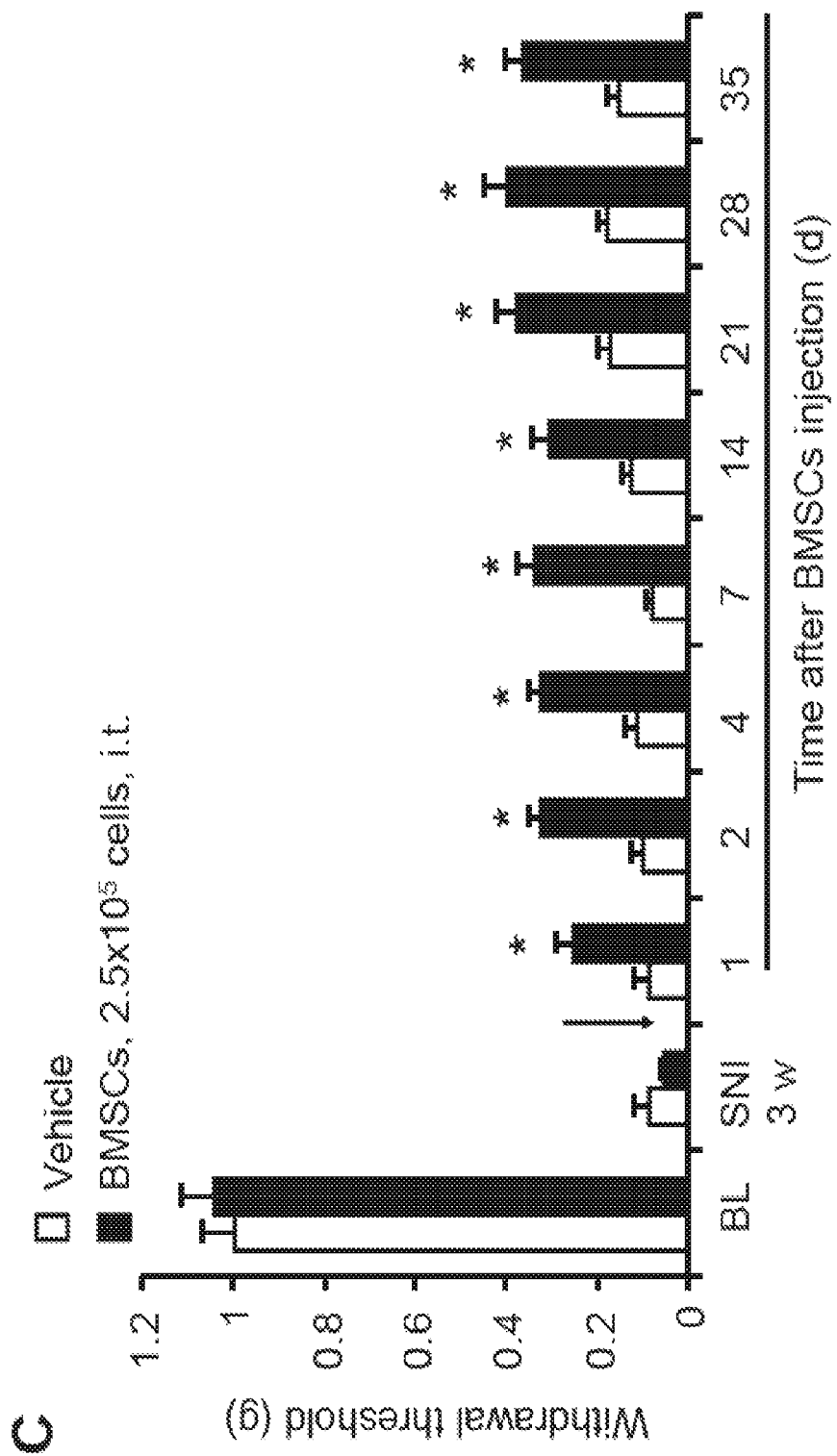
Figure 10:
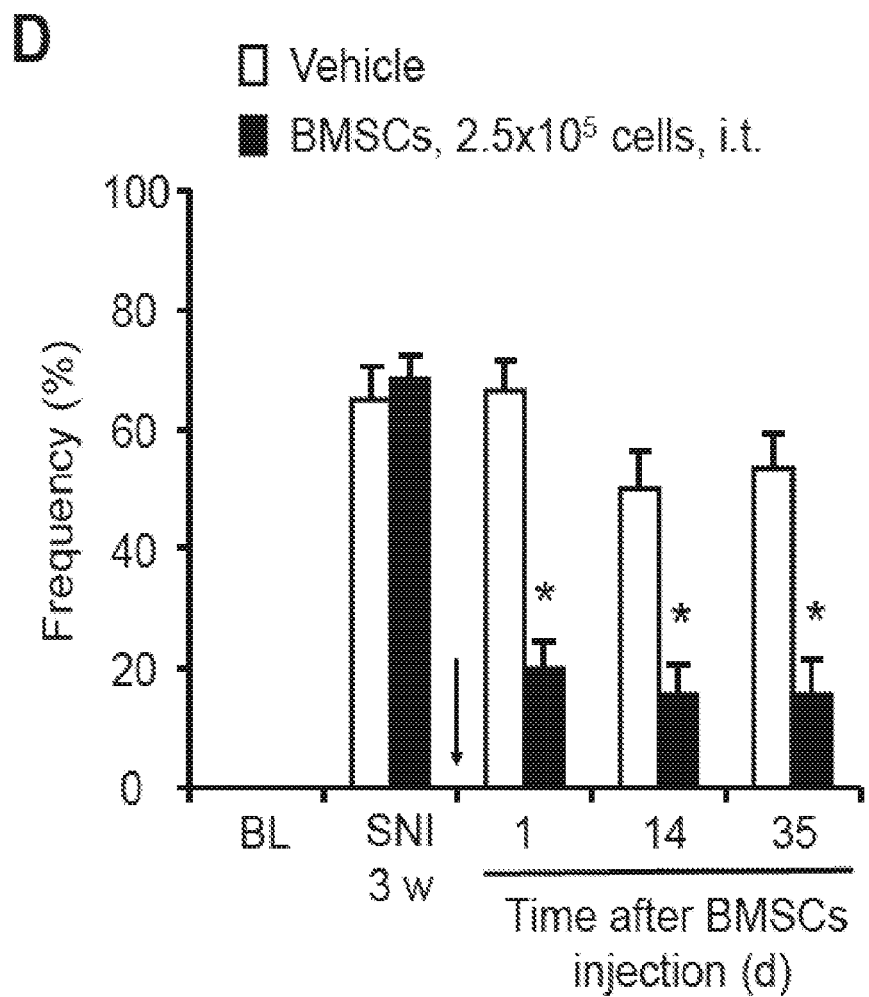
Figure 10:
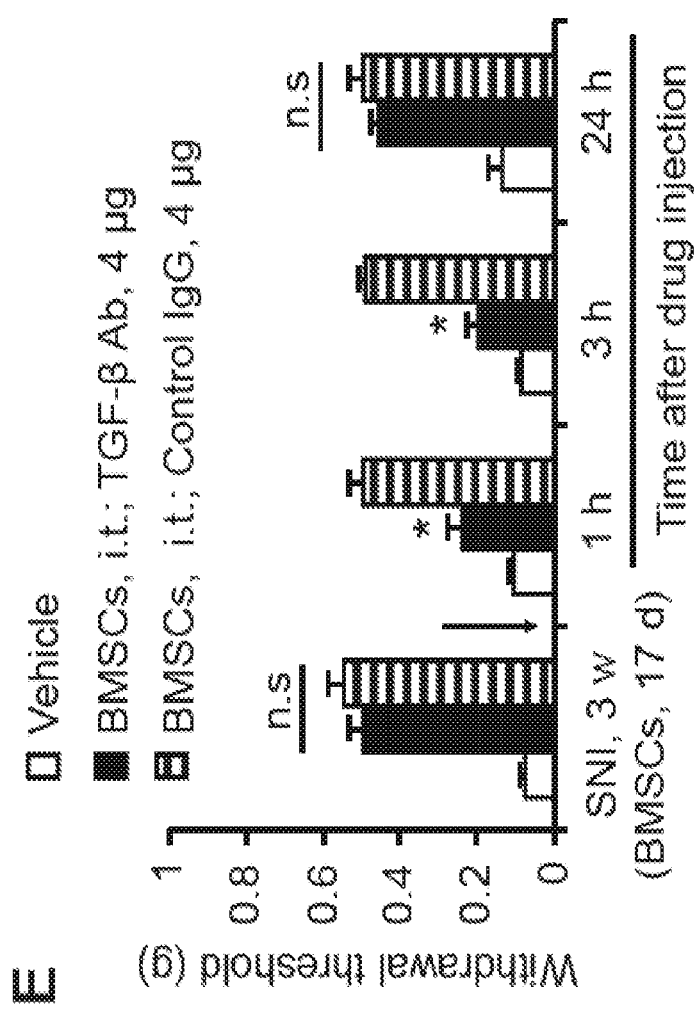

FIG. 10 shows that prolonged inhibition of SNI-induced mechanical allodynia by intrathecal BMSCs in early or late phase and its reversal by TGF-β1 antibody. (A and B) Long-term inhibition of mechanical allodynia by early treatment of BMSCs ($2.5 \times 10^5$ cells) via intrathecal (i.t.) injection, given 4 days after SNI. Mechanical allodynia was tested by paw withdrawal threshold (A) and by percentage response to a single 0.16 g filament (10 times, B). BL, baseline. *$P<0.05$, compared with vehicle (PBS), n=6 mice/group. (C and D) Sustained inhibition of mechanical allodynia by late treatment of BMSCs ($2.5 \times 10^5$ cells, i.t.), given 21 days after SNI. *$P<0.05$, compared with vehicle; #$P<0.05$, n=6 mice/group. (E) Reversal of BMSCs-induced inhibition of mechanical allodynia by TGF-β1 neutralizing antibody (4 μg, i.t.) given 3 weeks after SNI. n.s., no significance; *$P<0.05$, compared with control IgG group; n=5 mice per group. All data are expressed as mean±S.E.M. Statistical significance was determined by two-way ANOVA followed by Bonferroni post-hoc test.

Figure 11:
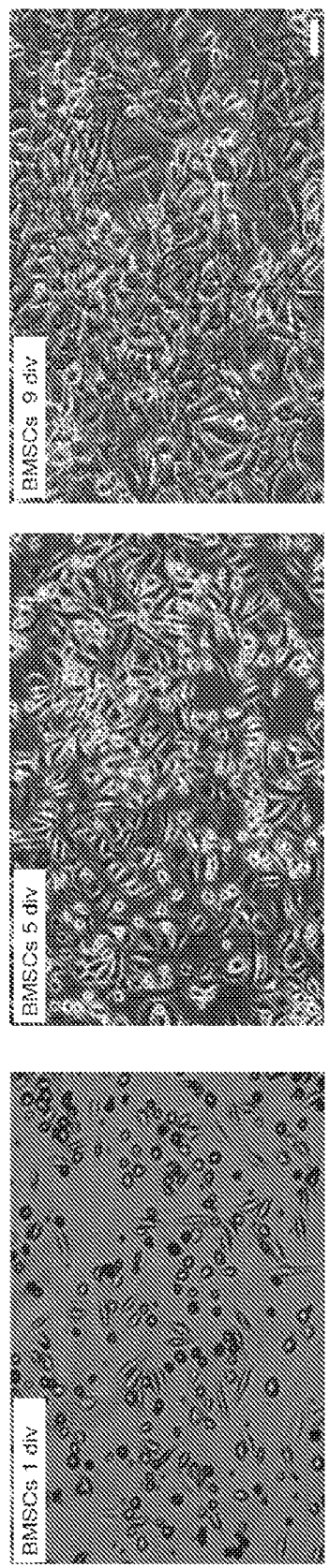
Figure 11:
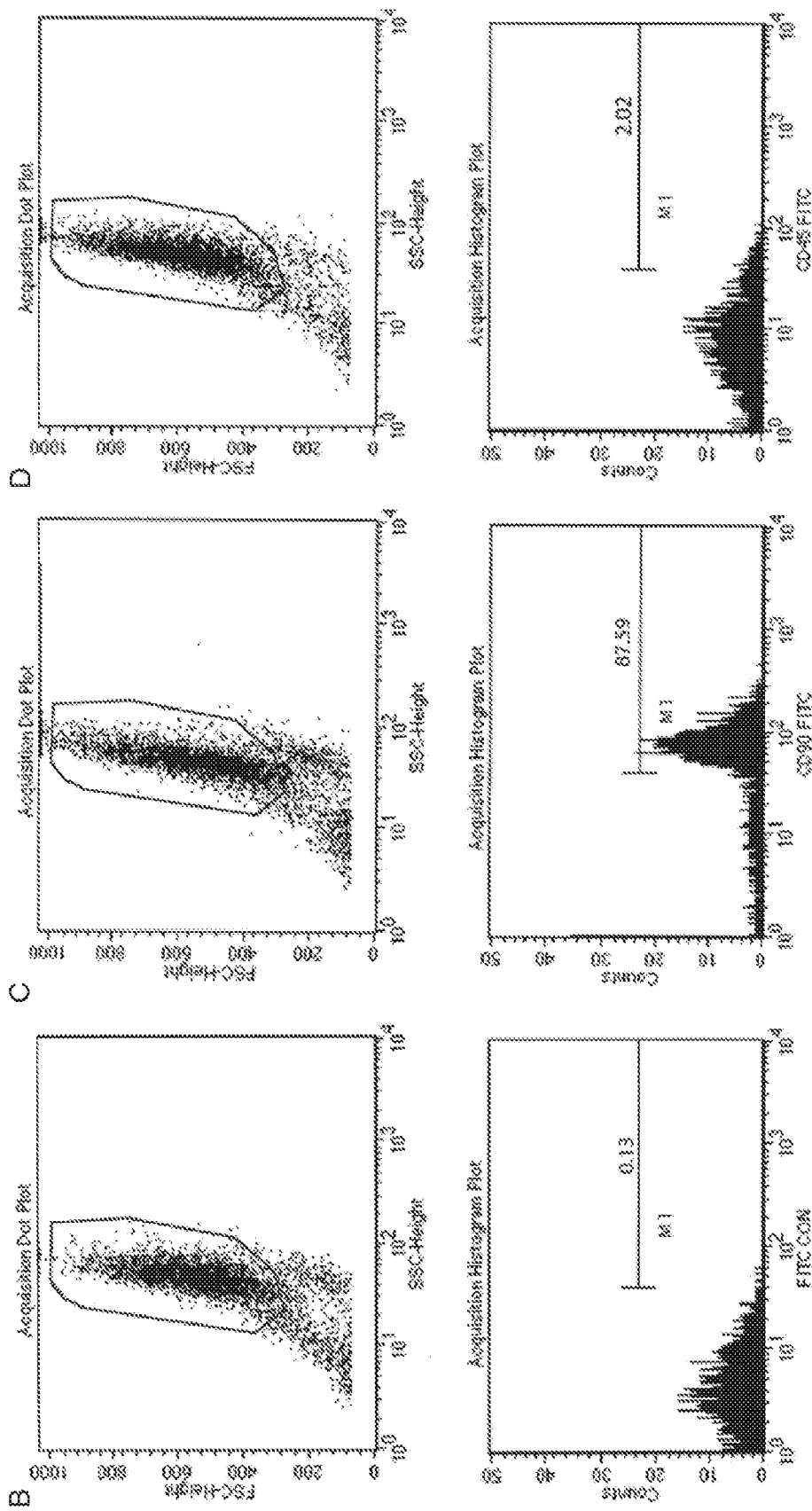

FIG. 11 shows that characterization of mouse BMSCs. (A) Typical images of mouse BMSCs cultures at 1, 5 and 9 days in vitro (div) after plating. Initially, the cultured cells are mostly spindle-shaped with large round nuclei and a few thin cell processes (left); cells then became locally confluent, growing in distinct colonies at 5 days (middle) and approached confluence at 9 days (right). Scale, 20 μm. (B-D) Flow cytometry analysis of cultured BMSCs at 9 days after plating. Up panels, SSC versus FSC scatter graphs. Low panels, plots of the number of immunoreactive cells versus relative fluorescence intensities. Note that 88% of the cultured BMSCs are positive for the stem cell marker CD90 (C) and only 2% of the cells are positive for the hematopoietic marker CD45 (D). Isotype-matched IgG-FITC antibody (B) was used as control.

Figure 12:
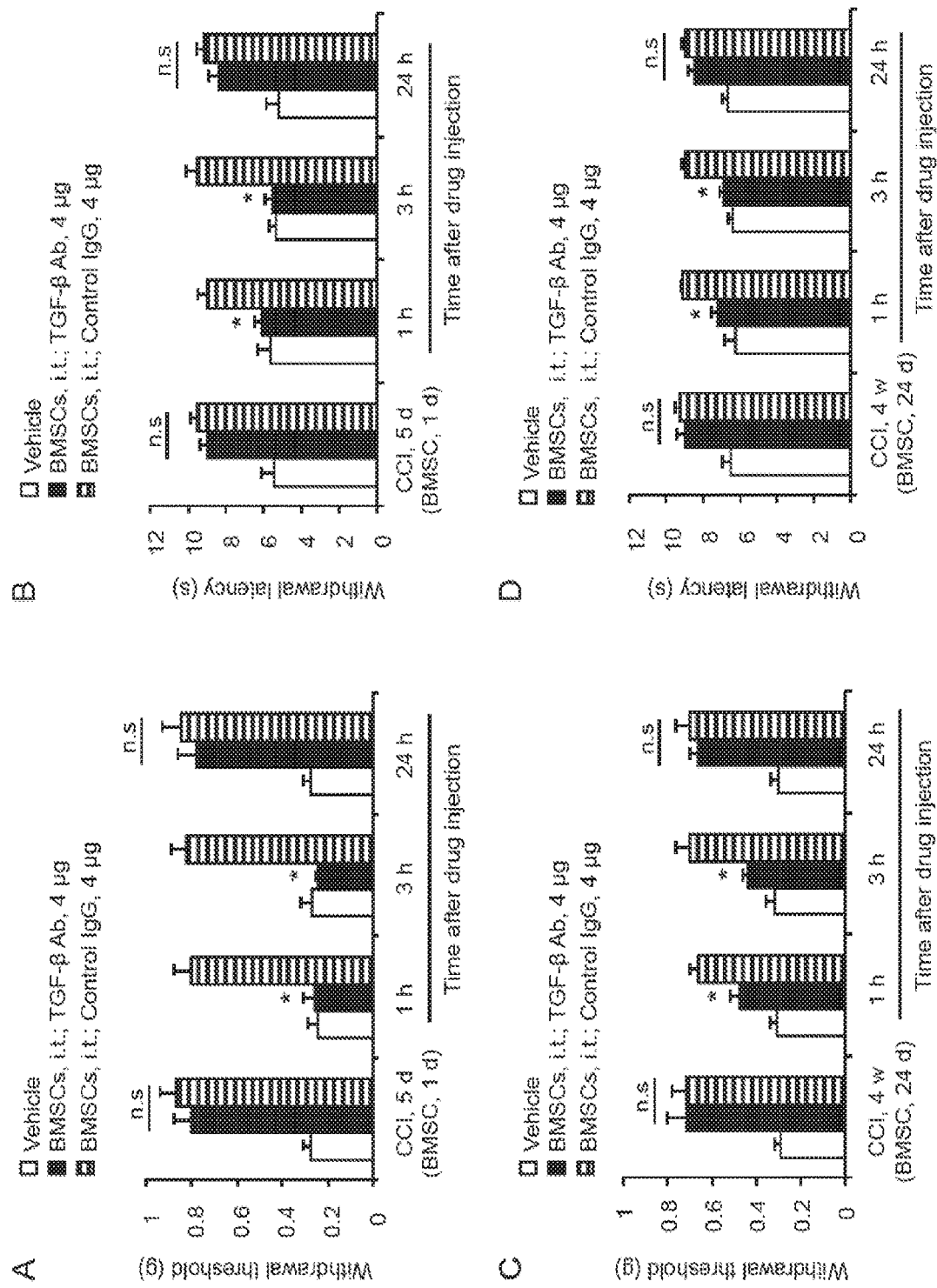
Figure 12:
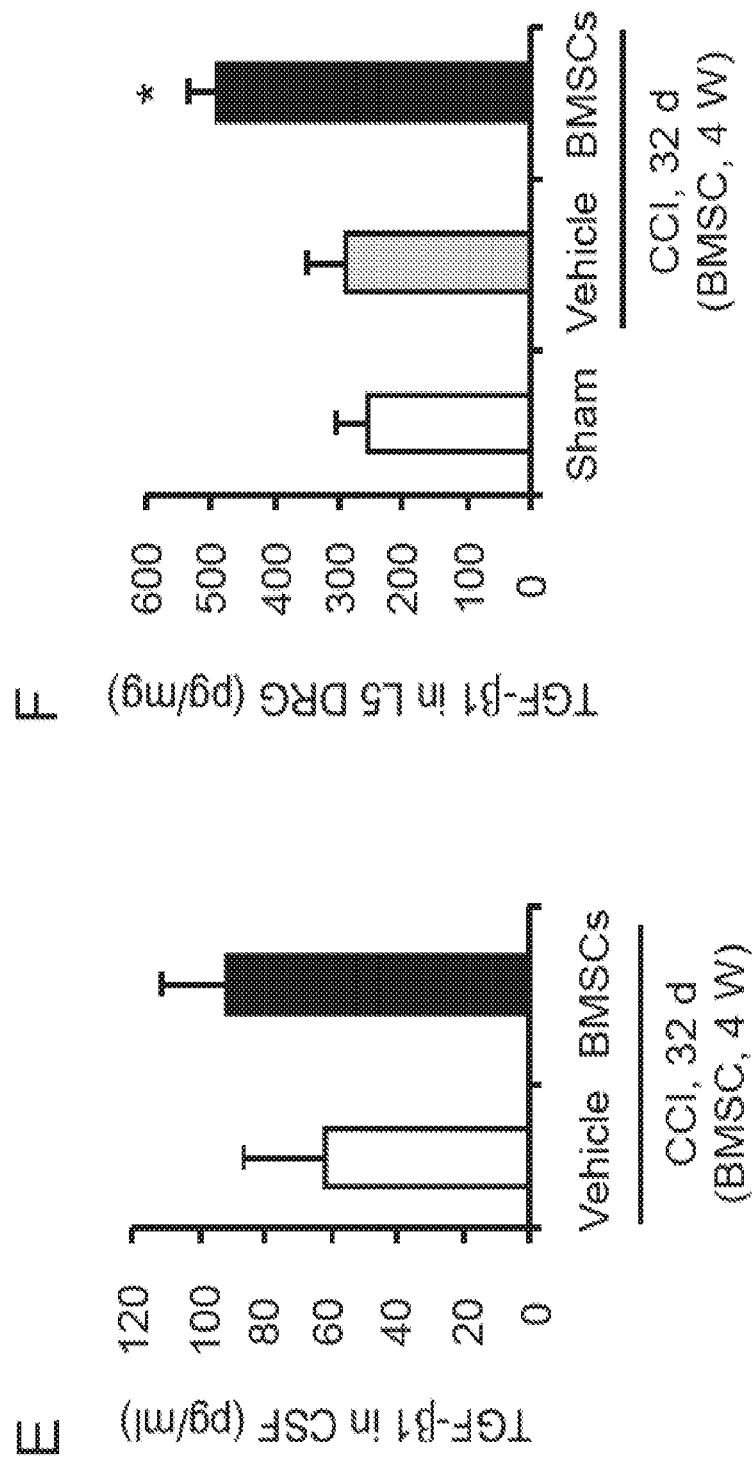

FIG. 12 shows that the anti-allodynic and anti-hyperalgesic effects of intrathecal BMSCs ($2.5 \times 10^5$) in earlier and later phases of CCI were reversed by the TGF-β1 neutralization. (A-D) TGF-β neutralizing antibody (4 μg, i.t.), given at 1 day (A, B) or 24 days (C, D) after BMSCs injection, reverses BMSCs-induced inhibition of mechanical allodynia (A, C) and hyperalgesia (B, D) after CCI. n.s., no significance; *$P<0.05$, compared with control IgG group; n=5-6 mice per group. (E, F) TGF-β1 levels in CSF (E) and L5 DRGs (F) 28 days after BMSCs injection. *$P<0.05$, compared with vehicle group. n=5-7 mice per group. Statistical significance was determined by two-way ANOVA followed by Bonferroni post-hoc test (A-D) or Student's t test (E and F). All data are expressed as mean±S.E.M.

Figure 13:
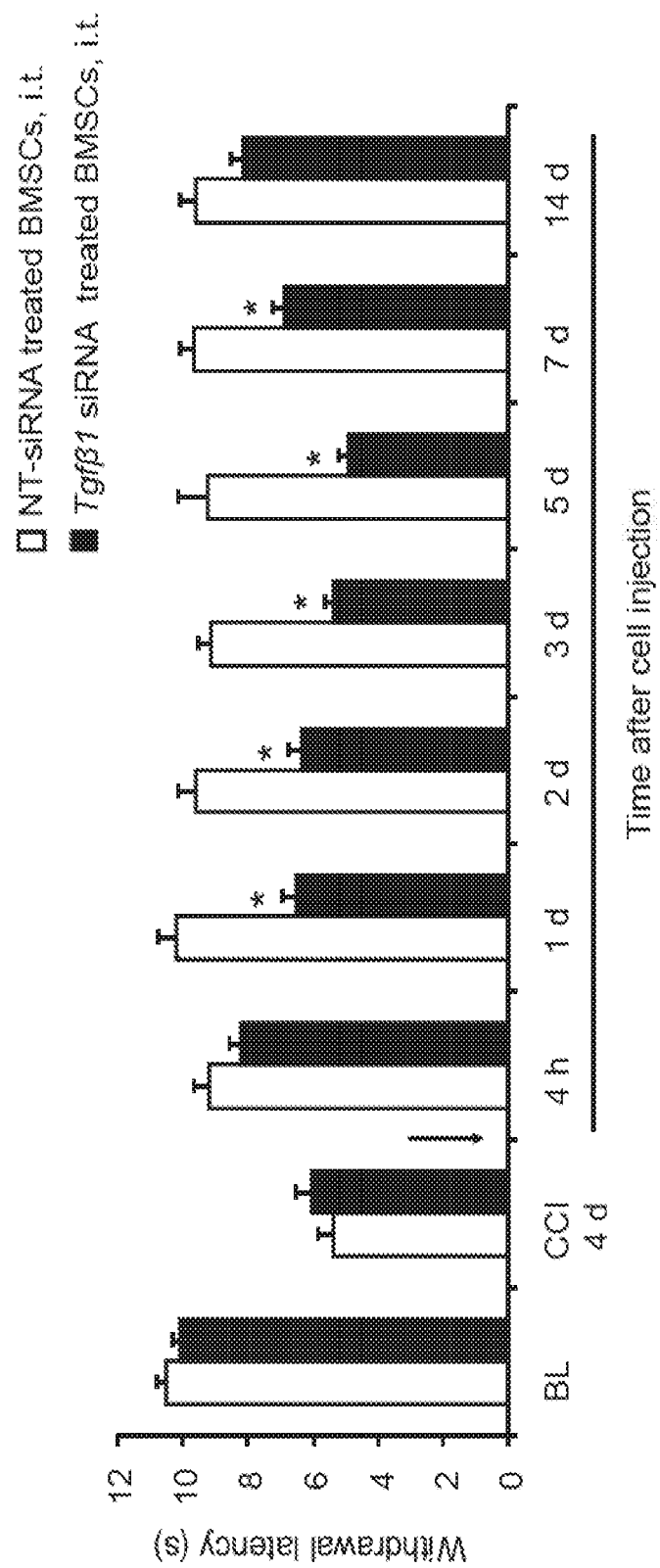

FIG. 13 shows the effects of BMSCs, pre-treated with Tgfβ1 or control siRNA, on CCI-induced thermal hyperalgesia in CCI mice. Intrathecal injection of non-targeting siRNA treated BMSCs ($2.5 \times 10^5$) reversed thermal hyperalgesia for >14 d. However, this inhibitory effect was compromised when BMSCs were pre-treated with Tgfβ1 siRNA. Arrow indicates the injection of BMSCs on CCI day 4. Note the difference between the two groups disappeared 2 weeks after the BMSCs injection. *$P<0.05$, compared with non-targeting control siRNA treated group. n=5 mice per group. Statistical significance was determined by Student's t test. Data are expressed as mean±S.E.M.

Figure 14:
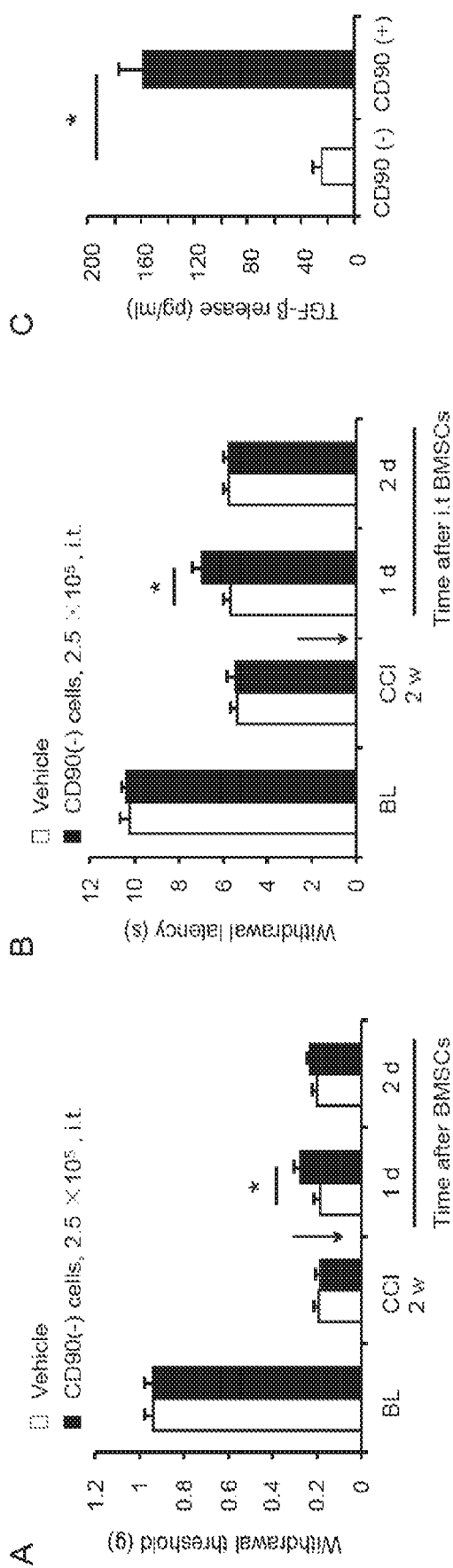

FIG. 14 shows that intrathecal injection of CD90-negative cells produced mild and transient relief of neuropathic pain after CCI. (A, B) Intrathecal injection of CD90-negative cells, 2 weeks after CCI, only elicited mild and transient inhibition of CCI-induced mechanical allodynia (A) and heat hyperalgesia (B). *$P<0.05$, compared with vehicle group; n=6 mice/group. (C) ELISA analysis showing that CD90-negative cells secreted much less TGF-β1, compared to CD90-positive cells. *$P<0.05$, n=6 mice/group. Statistical significance was determined by two-way ANOVA followed by Bonferroni post-hoc test (A and B) or Student's t test (C). All data are expressed as mean±S.E.M.

Figure 15:
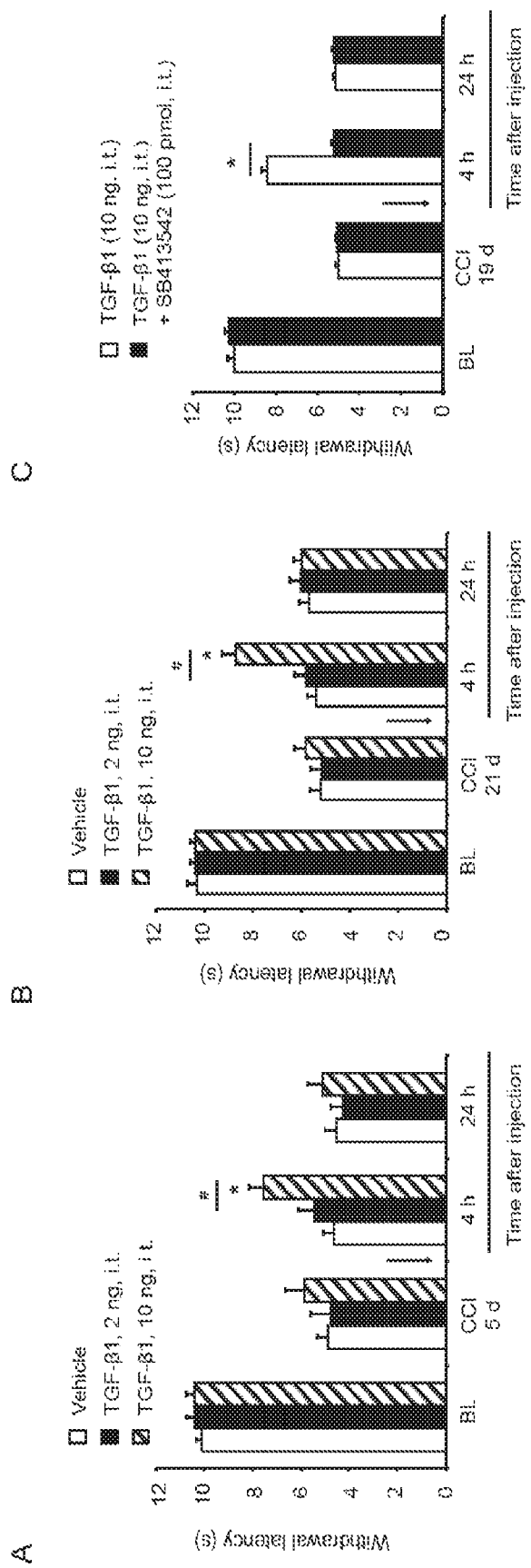

FIG. 15 shows that TGF-β1 significantly attenuated CCI-induced thermal hyperalgesia through TGF-β receptor 1 (TGF-βR1). (A, B) Intrathecal injection (indicated with an arrow) of TGF-β1 (2 and 10 ng) dose-dependently suppressed thermal hyperalgesia 5 and 21 days after CCI. *$P<0.05$, compared with vehicle group; #$P<0.05$; n=5 mice per group. (C) Intrathecal injection (indicated with an arrow) of the TGF-βR1 inhibitor SB413542 (100 pmol) blocked the effect of TGF-β1 (10 ng) on thermal hyperalgesia. *$P<0.05$, compared with TGF-β1 group; n=4 mice for TGF-β1 group, n=5 mice for TGF-β1 plus SB431542 group. Statistical significance was determined by Two-way repeated-measures ANOVA followed by Bonferroni post-hoc test (A, B) or Student's t test (C). All data are expressed as mean±S.E.M.

Figure 16:
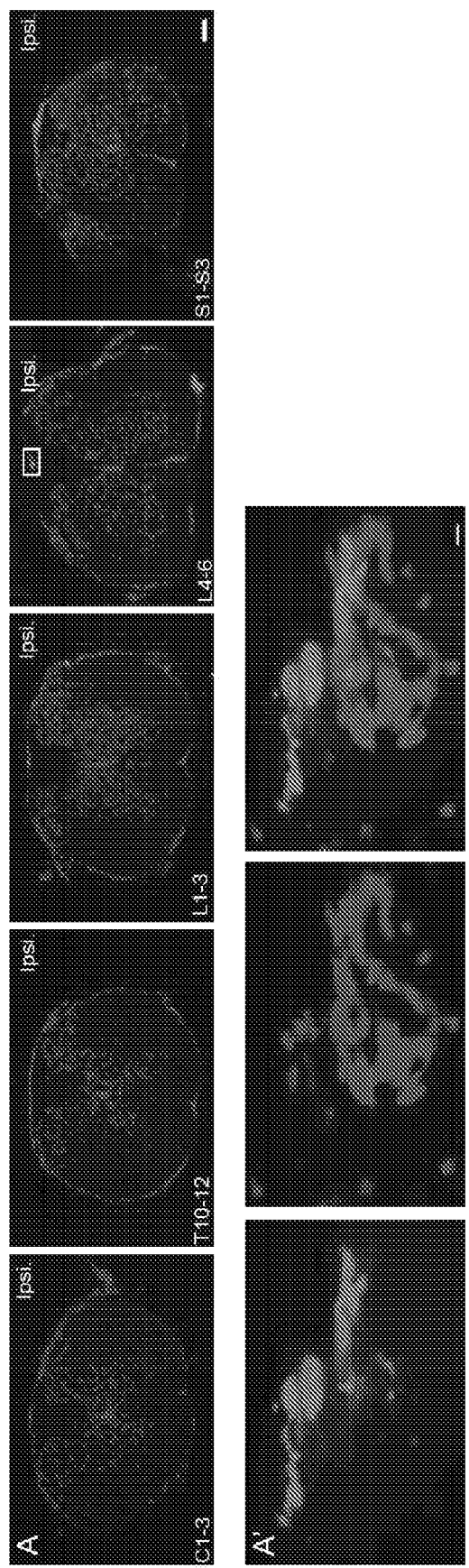

FIG. 16 shows the distribution of CM-Dil labeled BMSCs in spinal cord segments of CCI mice after intrathecal injection of Dil-labeled BMSCs. (A) Dil-labeling on spinal cord sections from cervical (C), thoracic (T), lumbar (L), and sacral (S) segments of CCI mice receiving i.t. injection of CM-Dil-labeled BMSCs ($2.5 \times 10^5$, CCI-4 d). Animals were sacrificed 3 d after i.t. injection (7 d after CCI). Note a preferential accumulation of Dil-BMSCs on the edges of the spinal cord especially on the ipsilateral side. (A') Enlargement of the box in A for the staining of Dil (left), DAPI (middle), and merged (right). Scales, 200 μm in A and 20 μm in A'.

Figure 17:
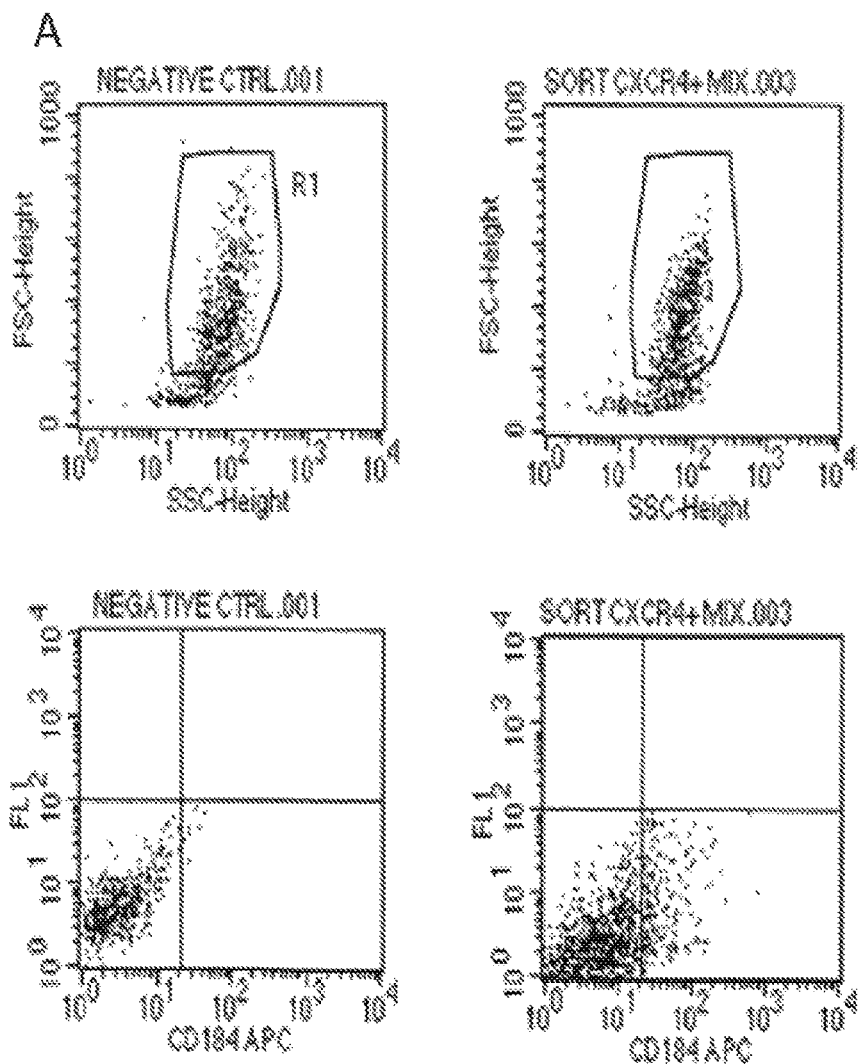
Figure 17:
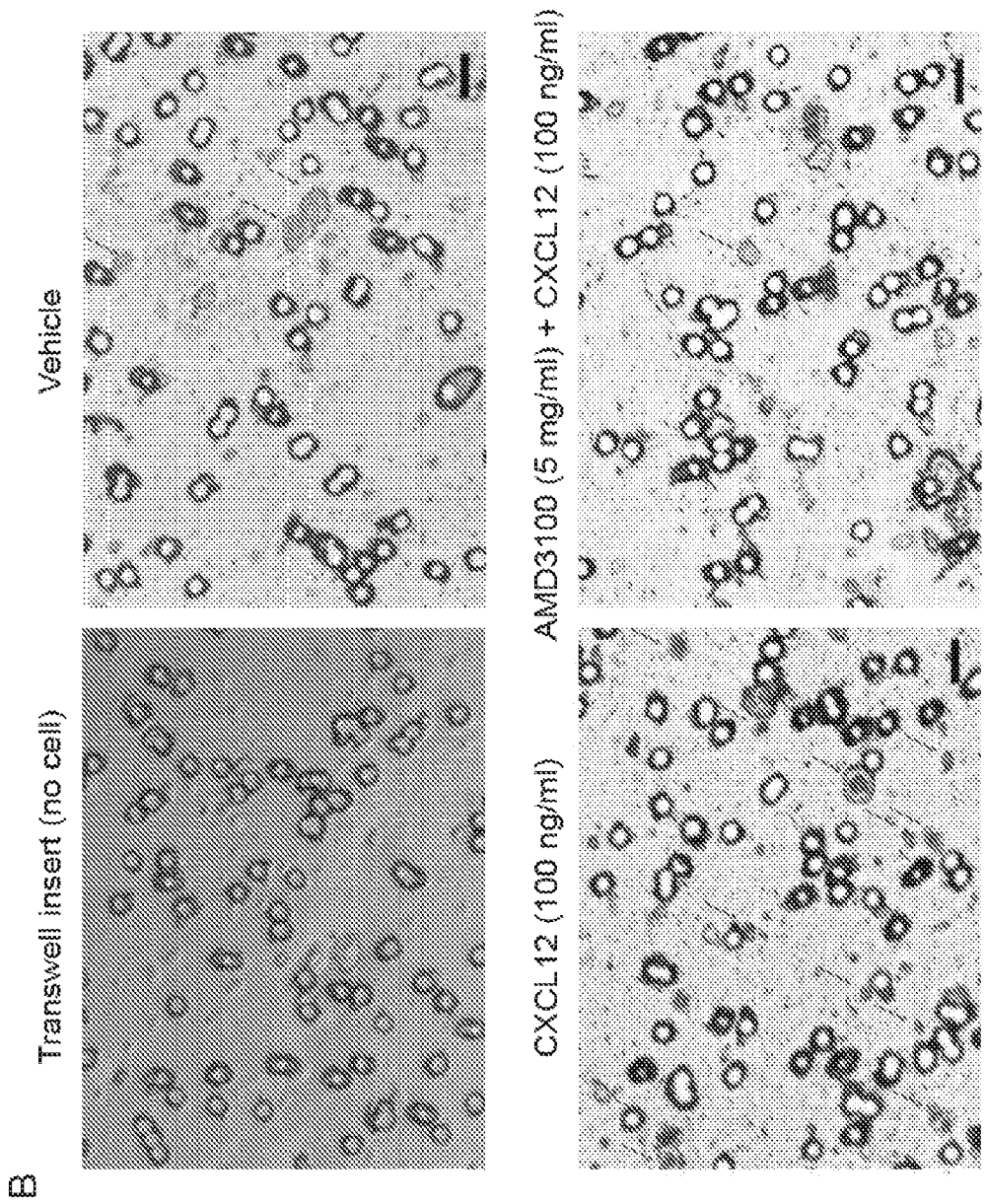

FIG. 17 shows CXCL12/CXCR4 axis controls the migration of BMSCs in vitro. (A) Representative images of flow cytometric analysis showing surface expression of CXCR4 in BMSCs. Cells were stained with either specific anti-mouse CXCR4 antibody (right) or isotype-matched control antibody (left). The percentage of CXCR4+ BMSCs is 18.84%. It is possible that cells with low expression of CXCR4 were not detected. (B) Representative images of the transwell migratory assay. CXCL12 induced BMSCs migration, which was inhibited by CXCR4 antagonist AMD3100. Scale, 20 μm.

Figure 18:
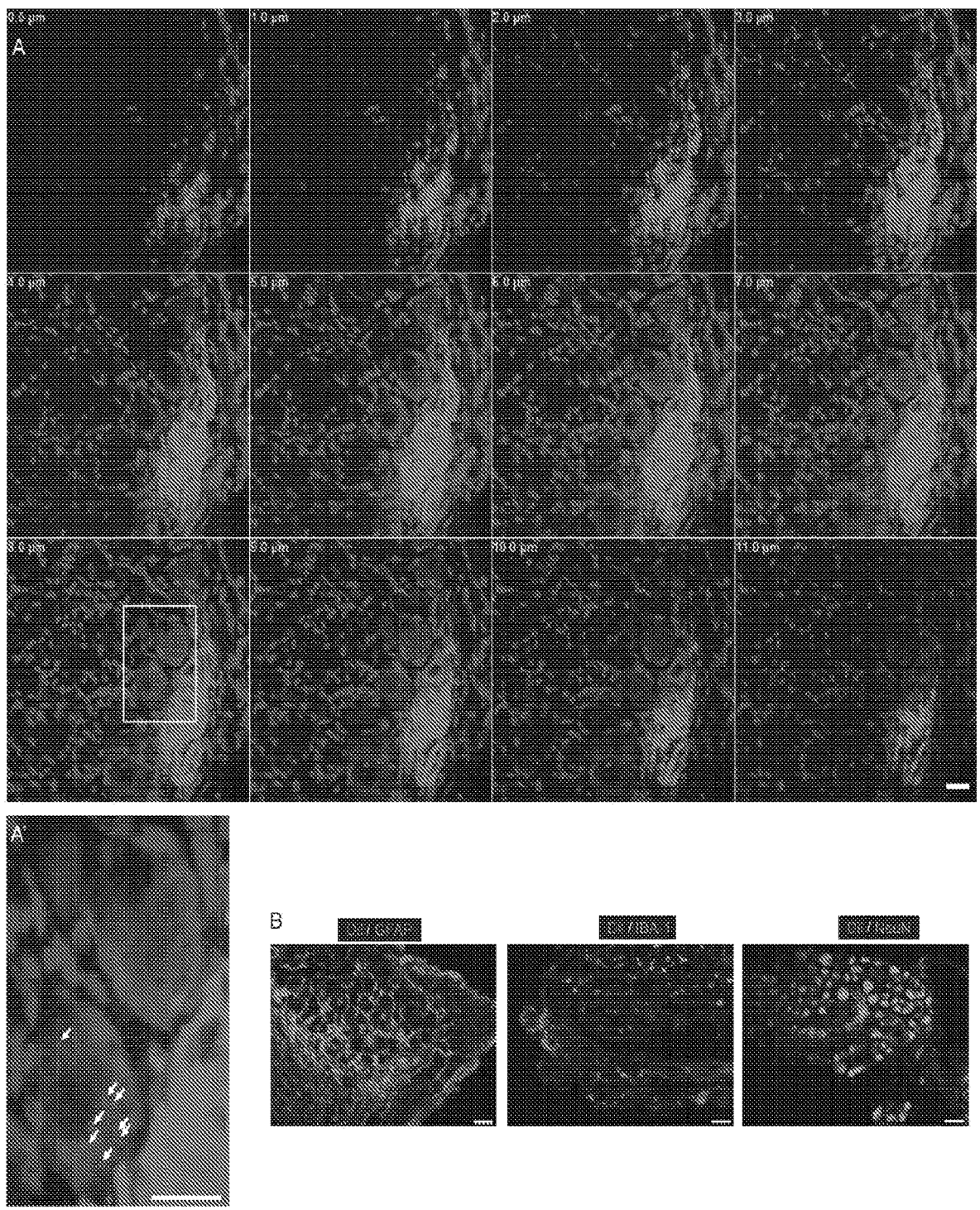

FIG. 18 shows (A) Z-stack (1 μm interval) confocal images showing CM-Dil labeled BMSCs ($2.5 \times 10^5$) in the L5-DRG 28 d after the i.t. injection. Note the close-proximity of BMSCs with DRG neurons. Scale, 20 μm. (A') Enlarged box in A. Arrows show the uptake of Dil-labeled particles by neurons adjacent to BMSCs, indicating active exchanges between neurons and BMSCs. Scale, 20 μm. Blue cells are DAPI-labeled nuclei. (B) Double staining of CM-Dil labeled BMSCs with GFAP (satellite glial marker), IBA-1 (macrophage marker), and NeuN (neuronal marker) in L5-DRGs 28 d after the i.t. injection of BMSCs. Note there is no co-localization with GFAP, IBA-1, and NeuN. Scales, 50 μm.

FIG. 19 shows (A) paradigm for induction of the chemotherapy-induced neuropathic pain model. Paclitaxel (PAX, 2 mg/kg, i.p.) was given on day 1, 3, 5 and 7, and BMSC were intrathecally injected on day 10. (B) PAX-induced neuropathic pain (mechanical allodynia), as evaluated by paw withdrawal frequency to von Frey hair (0.4 g) stimuli (10×). PAX-induced mechanical allodynia was significantly reduced by BMSC. *$P<0.05$, vs vehicle, Two-Way ANOVA, n=7 mice/group. Data are mean±SEM.

Figure 20:
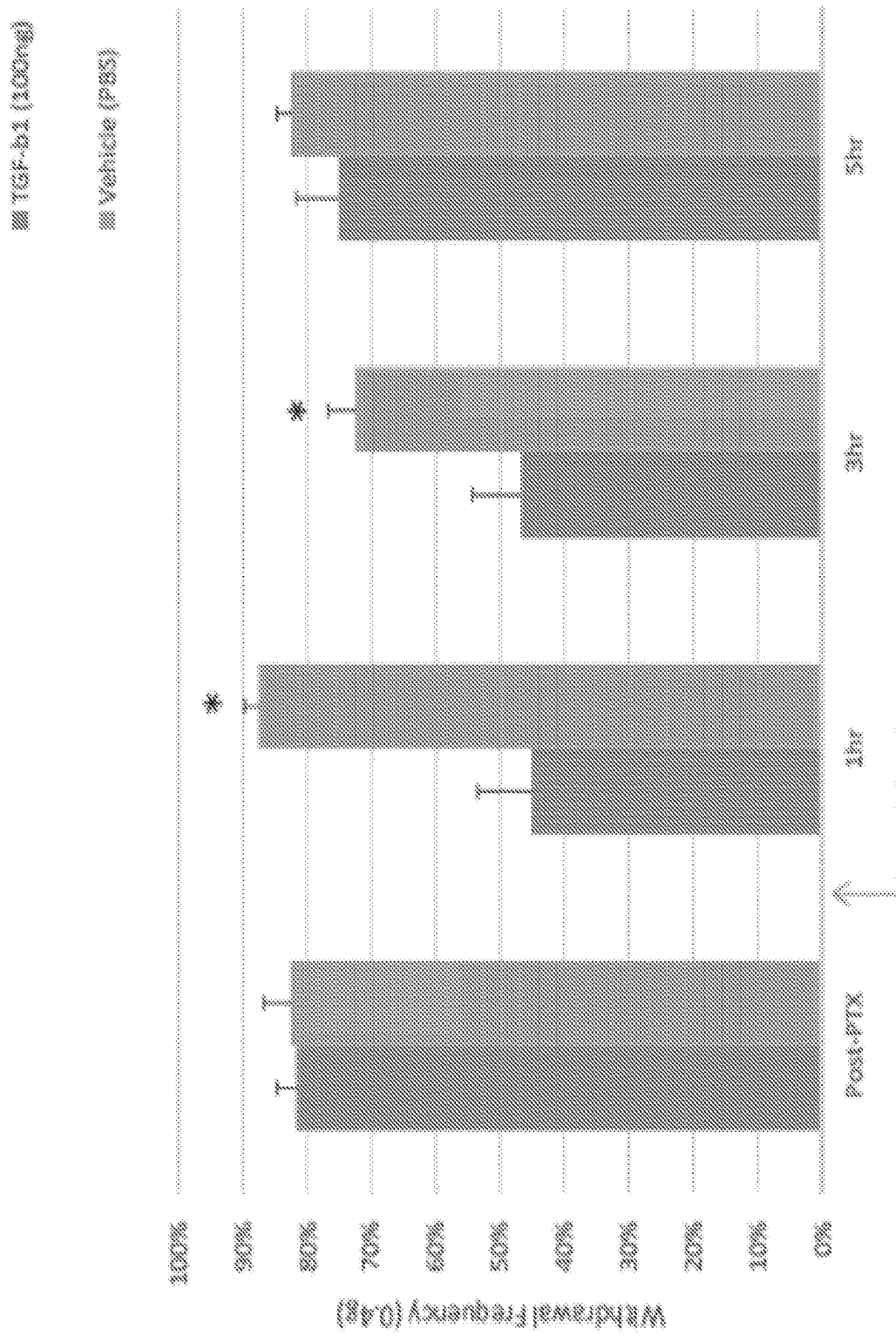

FIG. 20 shows the analgesic effects of TGF-β1 on PAX-induced neuropathic pain. Paclitaxel (2 mg/kg, i.p.) was given on day 1, 3, 5, and 7. At 7 weeks following the first injection with Paclitaxel, mice were intrathecally injected with TGF-β1 (100 ng). PAX-induced neuropathic pain was evaluated by paw withdrawal frequency to von Frey hair (0.4 g) stimuli (10×). Intrathecal TGF-β1 transiently reversed PAX-induced mechanical allodynia for 3 hours following injection. *$P<0.05$, vs TGF-β1, Two-Way ANOVA, n=4 mice/group for vehicle treatment, n=6 mice/per group for TGF-β1 treatment. Data are mean±SEM.

DETAILED DESCRIPTION

The present invention relates to the use of bone marrow stromal cells for the treatment of pain. The bone marrow stromal cells may express and secrete TGF-β1. The bone marrow stromal cells may express CXCR4, which binds to CXCL12. CXCL12 may be produced by the dorsal root ganglia (DRGs) and spinal cord segments that are affected by nerve and tissue injury. The bone marrow stromal cells may be administered by injection. For example the bone marrow stromal cells may be injected intrathecally or injected directly into the dorsal root ganglia. The bone marrow stromal cells, upon intrathecal administration, may migrate towards DRGs and spinal cord tissue (including DRG neurons expressing CXCL12). The neurons expressing CXCL12 may be injured neurons. For example, the CXCL12-expressing neurons may have injured axons or may be inflamed. The CXCL12-expressing neurons may be intact and activated by injury-induced inflammatory mediators. After migration, the bone marrow stromal cells may remain localized at the edge of dorsal root ganglia (DRGs), secreting TGF-β1 and without differentiation into other types of cells. TGF-β1, in turn, facilitates reduction or suppression of pain associated with the neurons expressing CXCL12 (i.e., injured neurons). This reduction or suppression of pain may be for at least about 1 day, 1 week, 1 month, or 1 year. The bone marrow stromal cells may also facilitate protection of axons from injury. The herein described methods may also administer TGF-β1. TGF-β1 may be useful for the treatment of pain. The TGF-β1 may also be administered by injection. TGF-β1 may be injected intrathecally, or injected directly into the dorsal root ganglia.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an," and "the" include plural references unless the context clearly dictates otherwise. The present disclosure also contemplates other embodiments "comprising," "consisting of" and "consisting essentially of," the embodiments or elements presented herein, whether explicitly set forth or not.

"Autologous administration" as used herein may refer to administration of a cell(s) to a subject from which the cell was obtained or derived from. In some embodiments, the cell(s) may be a bone marrow stromal cell(s) as described herein.

"Autologous bone marrow stromal cells" and "autologous BMSCs" as used interchangeably herein may refer to bone marrow stromal cells derived from the same subject or donor subject. Autologous bone marrow stromal cells may also be bone marrow stromal cells intended for administration to the subject from which they were obtained or derived from.

"Donor subject" and "donor patient" as used herein interchangeably refer to any vertebrate from which bone marrow stromal cells are obtained and may include, but is not limited to, a mammal (e.g., cow, pig, camel, llama, horse, goat, rabbit, sheep, hamster, guinea pig, cat, rat, mouse, a non-human primate (for example, a monkey such as a cynomolgous or rhesus monkey, chimpanzee, etc.), and a human). In some embodiments, the donor subject or donor patient may be a human or a non-human. In other embodiments, the donor subject or donor patient may be a bovine, a canine, an equine, a feline, or a porcine. In still other embodiments, the donor subject or donor patient may be a transgenic organism.

"Fragment" as used herein, may mean a portion of a reference peptide or polypeptide or nucleic acid sequence. The fragments can be DNA fragments selected from at least one of the various nucleotide sequences that encode protein fragments. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth herein.

The fragments can be polypeptide fragments. Fragments of proteins can comprise at least 10%, at least 20%, at least 30%, at least 40%, at least 50%, at least 60%, at least 70%, at least 80%, at least 90% or at least 95% of a reference protein. In some embodiments, fragments of reference proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a protein sequence disclosed herein.

"Heterologous administration" as used herein may refer to administration of a cell(s) to a subject, wherein the cell(s) was obtained or derived from a source other than the subject. In some embodiments, the source may be a cell line as described herein or a donor subject. In other embodiments, the source may be a donor subject that is a different species than the subject receiving the cell(s). In still other embodiments, the source may be a cell(s) obtained or derived from a species that is a different species than the subject receiving the cell(s). In some embodiments, the cell(s) may be a bone marrow stromal cell(s) as described herein.

"Heterologous bone marrow stromal cells" and "heterologous BMSCs" as used interchangeably herein may refer to bone marrow stromal cells derived from different subjects or donor subjects. Heterologous bone marrow stromal cells may also be bone marrow stromal cells intended for administration to a subject other than the subject from which they were obtained or derived from. Heterologous bone marrow stromal cells may further be bone marrow stromal cells intended for administration to a subject that is a different species than the species from which the bone marrow stromal cells were obtained or derived from.

"Inflammation" as used herein may refer to a biological response of a vascular tissue to stimuli, for example, but not limited to, tissue injury, infection, and irritants. Signs of acute inflammation may include pain, heat, redness, swelling, and/or loss of function. Inflammation may result in the production of inflammatory mediators, leading to generation and sensitization of pain.

"Intrathecal" administration, as used herein, refers to administration via injection into the spinal canal. Intrathecal administration may include administration via injection into the subarachnoid space. Intrathecal administration may facilitate contact with the cerebrospinal fluid (CSF). Intrathecal administration may facilitate delivery beyond the blood-brain barrier.

"Neurogenic inflammation" as used herein may refer to inflammation that may be triggered by the activation of primary afferent neurons and the subsequent release of inflammatory mediators, for example, but not limited to, substance P and calcitonin gene-related peptide.

"Neuroinflammation" as used herein may refer to local inflammation that may occur in the peripheral nervous system (PNS; e.g., peripheral nerves and ganglia) and/or central nervous system (CNS; e.g., spinal cord and brain). In some embodiments, neuroinflammation may include infiltration of leukocytes and increased production of inflammatory mediators in the PNS and CNS. In some embodiments, neuroinflammation may include activation of glial cells (e.g., microglia and astrocytes) in the PNS and CNS.

"Prophylactically effective amount" as used herein refers to an amount effective, at dosages and for periods of time necessary, to achieve the desired prophylactic result. Typically, since a prophylactic dose is used in subjects prior to or at an earlier stage of pain, disease or injury, the prophylactically effective amount will be less than the therapeutically effective amount.

"Recombinant" as used herein may refer to a cell, or nucleic acid, protein, or vector, wherein the cell, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant) form of the cell or express native genes that are otherwise abnormally expressed, under expressed or not expressed at all.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, mouse, a non-human primate (for example, a monkey, such as a cynomolgous or rhesus monkey, chimpanzee, etc.) and a human). In some embodiments, the subject may be a human or a non-human. In other embodiments, the subject may be a bovine, a canine, an equine, a feline, or a porcine. The subject or patient may be undergoing other forms of treatment.

"Therapeutically effective amount" as used herein refers to an amount effective, at dosages and for periods of time necessary, to achieve the desired therapeutic result. A therapeutically effective amount may be the amount and/or duration of a therapy which is sufficient to reduce or ameliorate the severity and/or duration of pain, an injury, a disorder or one or more symptoms thereof, prevent the advancement of a disorder, cause regression of a disorder, prevent the recurrence, development, onset, or progression of one or more symptoms associated with a disorder, detect a disorder, or enhance or improve the prophylactic or therapeutic effect(s) of another therapy (e.g., prophylactic or therapeutic agent). A therapeutically effective amount of the bone marrow stromal cells, TGF-β1, or pharmaceutical composition may be determined by a person skilled in the art and may vary according to factors such as the pain, injury, or disease state, age, sex, and weight of the individual, and the ability of the bone marrow stromal cells, TGF-β1, or pharmaceutical composition to elicit a desired response in the individual. A therapeutically effective amount is also one in which any toxic or detrimental effects of the bone marrow stromal cells, TGF-β1, or pharmaceutical composition, are outweighed by the therapeutically beneficial effects.

"Transformation" as used herein refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells that transiently express the inserted DNA or RNA for limited periods of time.

"Transgenic organism" as used herein refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

"Treat," "treating," or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of pain, injury, or disease or symptoms associated with such disease prior to affliction with the pain, injury, or disease. Such prevention or reduction of the severity of a disease prior to affliction refers to administration of bone marrow stromal cells, TGF-β1, or a pharmaceutical composition of the present invention to a subject that is not at the time of administration afflicted with the pain, injury, or disease. "Preventing" also refers to preventing the recurrence of a disease or of one or more symptoms associated with such disease. "Treatment" and "therapeutically" refer to the act of treating, as "treating" is defined above.

"Variant" as used herein may refer to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554, 101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. BONE MARROW STROMAL CELLS (BMSCS)

Provided herein are bone marrow stromal cells (BMSCs) for use in a method of treating pain. The method of treating pain is described below in more detail. Bone marrow stromal cells are progenitor cells of mesodermal origin that are present in the bone marrow of adult subjects and may give rise to various tissues. The bone marrow stromal cells may express and/or secrete transforming growth factor beta-1 (TGF-β1). The bone marrow stromal cells may express chemokine (C-X-C Motif) Receptor 4 (CXCR4). The bone marrow stromal cells may migrate towards cells expressing CXCL12. The bone marrow stromal cells may express and/or secrete TGF-β1 and express CXCR4. The bone marrow stromal cells may express and/or secrete TGF-β1 and migrate towards cells expressing CXCL12. The bone marrow stromal cells may express CXCR4 and migrate towards cells expressing CXCL12. The bone marrow stromal cells may express and/or secrete TGF-β1, express CXCR4, and migrate towards cells expressing CXCL12.

The bone marrow stromal cells may suppress the immune system, i.e., they may be immunosuppressive. Accordingly, the bone marrow stromal cells may be employed in autologous administration or heterologous administration without requiring immune suppressants. As such, the bone marrow stromal cells may be autologous bone marrow stromal cells, heterologous bone marrow stromal cells, or a combination thereof.

The bone marrow stromal cells may exhibit a high expansion potential, genetic stability, and/or a stable phenotype(s). The bone marrow stromal cells, upon administration, may not differentiate into another type of cell.

The bone marrow stromal cells may be administered by injection. The bone marrow stromal cells may be injected intrathecally. The bone marrow stromal cells may be injected directly into the dorsal root ganglia. Upon administration, the bone marrow stromal cells may remain in a subject receiving the administration for at least about 15 minutes to about 6 months, from about 60 minutes to about 3 months, from about 12 hours to about 1 month, from about 1 day to about 2 months, from about 7 days to about 1 month, from about 10 days to about 20 days, or from about 4 days to about 14 days, for example. The bone marrow stromal cells may remain in a subject receiving the administration for at least about 15 minutes, 30 minutes, 60 minutes, 90 minutes, 120 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 1 month, 2 months, 3 months, 4 months, 5 months, or 6 month, for example.

The bone marrow stromal cells may be collected and shipped from the laboratory to the bedside. Preparation of the bone marrow stromal cells is described below in more detail. The bone marrow stromal cells may be compatible with different methods for administration and with formulations utilized in such methods of administration.

a. Transforming Growth Factor Beta-1 (TGF-β1)

The bone marrow stromal cells may express and/or secrete transforming growth factor beta-1 (TGF-β1). In humans, TGF-β1 is encoded by the TGFB1 gene and this gene is located on the q arm of chromosome 19 at position 13.1 (19q13.1). TGF-β1 is a cytokine involved in multiple cellular processes, for example, cell growth, cell proliferation, cell differentiation, cell movement, and apoptosis. In particular, TGF-β1 is an anti-inflammatory cytokine that may inhibit the activation and proliferation of microglia and astrocytes, and reduce the expression of pro-inflammatory cytokines in neuropathic pain conditions.

TGF-β1 may suppress pain. For example, TGF-β1 secreted by bone marrow stromal cells may suppress neuropathic pain. The neuropathic pain may be caused by injured dorsal root ganglion (DRG) neurons. The neuropathic pain may be early- or late-phase neuropathic pain. The presence of TGF-β1 may normalize nerve injury-induced spinal cord synaptic plasticity and DRG neuronal hyperexcitability. This neuromodulation by TGF-β1 may not occur via the canonical TGF-β1 signaling mechanism, which requires gene transcription.

b. Chemokine (C-X-C Motif) Receptor 4 (CXCR4) and Chemokine (C-X-C Motif) Ligand 12 (CXCL12)

The bone marrow stromal cells may express chemokine (C-X-C Motif) receptor 4 (CXCR4). CXCR4 may also be known as fusin or cluster of differentiation 184 (CD184). In humans, CXCR4 is encoded by the CXCR4 gene and this gene is located on the q arm of chromosome 2 at position 21 (2q21). CXCR4 is a chemokine receptor for chemokine (C-X-C Motif) ligand 12 (CXCL12), which exhibits chemotactic activity.

Administered bone marrow stromal cells expressing CXCR4 may migrate towards injured DRG neurons producing CXCL12. After migration, the bone marrow stromal cells may localize at the border, edge, or surrounding membrane of DRGs and the spinal cord. The bone marrow stromal cells may not migrate deep into these tissues nor differentiate into other cell types (e.g., neurons, satellite cells, or monocytes). Accordingly, after administration of bone marrow stromal cells expressing TGF-β1 and CXCR4, the bone marrow stromal cells may migrate towards injured DRG neurons producing CXCL12 and secrete TGF-β1 to suppress neuropathic pain caused by these injured DRG neurons.

c. Preparation of BMSCs

The bone marrow stromal cells may be prepared from any number of sources of bone marrow stromal cells (BMSC source). The BMSC source may be, for example, but is not limited to, a donor subject and a cell line. The bone marrow stromal cells prepared from the BMSC source may be a heterogeneous population of bone marrow stromal cells or a homogeneous population of bone marrow stromal cells. The bone marrow stromal cells may be autologous bone marrow stromal cells or heterologous bone marrow stromal cells.

Preparation of the bone marrow stromal cells may include sorting and/or modification of the bone marrow stromal cells, for example.

(1) Donor Subject

The bone marrow stromal cells may be prepared from the donor subject. Such preparation may include isolating the bone marrow stromal cells from the subject during surgery. The surgery may be, but is not limited to, hip surgery, knee surgery, and amputation.

(2) Cell Line

The bone marrow stromal cells may be prepared from the cell line. The cell line may be a bone marrow stromal cell line that expresses TGF-β1. The cell line may be a bone marrow stromal cell line that has been modified to express higher levels of TGF-β1 than the unmodified bone marrow stromal cell line.

The cell line may be a bone marrow stromal cell line that secretes TGF-β1. The cell line may be a bone marrow stromal cell line that has been modified to secrete higher levels of TGF-β1 than the unmodified bone marrow stromal cell line.

The cell line may be a bone marrow stromal cell line that expresses CXCR4. The cell line may be a bone marrow stromal cell line that has been modified to express higher levels of CXCR4 than the unmodified bone marrow stromal cell line.

The cell line may be a bone marrow stromal cell line that migrates towards cells expressing CXCL12.

The cell line may be a bone marrow stromal cell line that expresses TGF-β1 and CXCR4. The cell line may be a bone marrow stromal cell line that has been modified to express higher levels of TGF-β1 and CXCR4 than the unmodified bone marrow stromal cell line.

The cell line may be a bone marrow stromal cell line that secretes TGF-β1 and expresses CXCR4. The cell line may be a bone marrow stromal cell line that has been modified to secrete higher levels of TGF-β1 and express higher levels of CXCR4 than the unmodified bone marrow stromal cell line.

The cell line may be a bone marrow stromal cell line the expresses TGF-β1 and migrates towards cells expressing CXCL12. The cell line may be a bone marrow stromal cell line that has been modified to express higher levels of TGF-β1 than the unmodified bone marrow stromal cell line and migrates towards cells expressing CXCL12.

The cell line may be a bone marrow stromal cell line that secretes TGF-β1 and migrates towards cells expressing CXCL12. The cell line may be a bone marrow stromal cell line that has been modified to secrete higher levels of TGF-β1 than the unmodified bone marrow stromal cell line and migrates towards cells expressing CXCL12.

The cell line may be a bone marrow stromal cell line that expresses CXCR4 and migrates towards cells expressing CXCL12. The cell line may be a bone marrow stromal cell line that has been modified to express higher levels of CXCR4 than the unmodified bone marrow stromal cell line and migrates towards cells expressing CXCL12.

The cell line may be a bone marrow stromal cell line that expresses TGF-β1 and CXCR4, and migrates towards cells expressing CXCL12. The cell line may be a bone marrow stromal cell line that has been modified to express higher levels of TGF-β1 and CXCR4 than the unmodified bone marrow stromal cell line, and migrates towards cells expressing CXCL12.

The cell line may be a bone marrow stromal cell line that secretes TGF-β1, expresses CXCR4, and migrates towards cells expressing CXCL12. The cell line may be a bone marrow stromal cell line that has been modified to secrete higher levels of TGF-β1 and to express higher levels of CXCR4 than the unmodified bone marrow stromal cell line, and migrates towards cells expressing CXCL12.

The cell line may be a human bone marrow mesenchymal stem cell line.

(3) Sorting of BMSCs

As described above, the bone marrow stromal cells prepared from the BMSC source may be a heterogeneous population of bone marrow stromal cells. Such a heterogeneous population of bone marrow stromal cells may be sorted to isolate a homogeneous population of bone marrow stromal cells exhibiting a desired characteristic. The heterogeneous population of bone marrow stromal cells may be sorted by, for example, flow cytometry. The flow cytometry may be fluorescence-activated cell sorting (FACS) or based on the ability of the bone marrow stromal cells to migrate towards a CXCL12 gradient in a chemotaxis assay.

The desired characteristic may be expression of TGF-β1 and/or CXCR4. Accordingly, the heterogeneous population of bone marrow stromal cells may be sorted into a population of bone marrow stromal cells that express TGF-β1 and a population of bone marrow stromal cells that do not express TGF-β1. The heterogeneous population of bone marrow stromal cells may be sorted into a population of cells that express CXCR4 and a population of bone marrow stromal cells that do not express CXCR4. The heterogeneous population of bone marrow stromal cells may be sorted into a population of cells that express TGF-β1 and CXCR4, and a population of cells that do not express TGF-β1 and CXCR4.

(4) Modification of BMSCs

Preparation of the bone marrow stromal cells may include modification of the bone marrow stromal cells. Modification may be, but is not limited to, transformation of the bone marrow stromal cells with one or more nucleic acid molecules. The one or more nucleic acid molecules may encode a protein such as TGF-β1 and CXCR4, a fragment thereof, a variant thereof, or any combination thereof. The one or more nucleic acid molecules may be recombinant. This, in turn, may allow for increased expression of TGF-β1 and/or CXCR4 by the modified bone marrow stromal cells as compared to the unmodified bone marrow stromal cells. This may also allow for increased secretion of TGF-β1 and/or increased expression of CXCR4 by the modified bone marrow stromal cells as compared to the unmodified bone marrow stromal cells.

3. PHARMACEUTICAL COMPOSITION

Provided herein are pharmaceutical compositions for use in a method of treating pain. The pharmaceutical composition may contain the bone marrow stromal cells. The pharmaceutical composition may contain TGF-β1. The pharmaceutical composition may contain the bone marrow stromal cells and TGF-β1. The pharmaceutical composition may contain a pharmaceutically acceptable carrier. The pharmaceutically acceptable carrier may include any and all solvents, dispersion media, coatings, anti-bacterial and anti-fungal agents, isotonic and absorption delaying agents, and the like that are physiologically compatible. The isotonic agent may be, but is not limited to, sugars, polyalcohols such as mannitol, sorbitol, or sodium chloride. The pharmaceutically acceptable carrier may include minor amounts of auxiliary substances such as wetting or emulsifying agents, preservatives, or buffers, which enhance the effectiveness of the bone marrow stromal cells. Examples of pharmaceutically acceptable carriers include, but are not limited to, one or more of water, saline, phosphate buffered saline, dextrose, glycerol, ethanol, and the like, as well as combinations thereof. The pharmaceutical composition may also contain a diluent and/or excipient.

The pharmaceutical composition may be formulated to be compatible with its intended route of administration, such as injection. For example, the route of administration may be intrathecal injection, or direct injection into the dorsal root ganglia. When necessary, the composition may also include a local anesthetic such as lignocaine to ease pain at the site of administration.

Any number of modes of administering the herein described bone marrow stromal cells, TGF-β1, and pharmaceutical compositions may be used. Modes of administration may also include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. The following formulations and methods are merely exemplary and are in no way limiting. The pharmaceutical composition optionally may be sterile.

Formulations suitable for parenteral administration may include aqueous and non-aqueous, isotonic sterile injection solutions, which may contain anti-oxidants, buffers, bacteriostats, and solutes that render the formulation isotonic with the blood of the intended recipient, and aqueous and non-aqueous sterile suspensions that may include suspending agents, solubilizers, thickening agents, stabilizers, and preservatives. The formulations may be presented in unit-dose or multi-dose sealed containers, such as ampules and vials, and may be stored in a freeze-dried (lyophilized) condition requiring only the addition of the sterile liquid excipient, for example, water, for injections, immediately prior to use. Extemporaneous injection solutions and suspensions may be prepared from sterile powders, granules, and tablets of the kind previously described.

The bone marrow stromal cells, TGF-β1, and pharmaceutical compositions may include a "therapeutically effective amount" or a "prophylactically effective amount" of the bone marrow stromal cells and/or TGF-β1. A therapeutically effective amount or a prophylactically effective amount of the bone marrow stromal cells, TGF-β1, and/or pharmaceutical compositions may be determined by a person skilled in the art and may vary according to factors such as the disease state, age, sex, and weight of the individual, and the ability of the composition to elicit a desired response in the individual.

a. Bone Marrow Stromal Cells

The above-described bone marrow stromal cells may be a component in a pharmaceutical composition. The pharmaceutical composition may be administered using the method of treatment as described herein.

The pharmaceutical composition may further contain one or more prophylactic and/or therapeutic agents other than the bone marrow stromal cells. Such prophylactic and/or therapeutic agents may be useful for, or have been used, or are currently being used in the prevention, treatment, management, or amelioration of a disorder, or one or more symptoms thereof. In some embodiments, the one or more prophylactic and/or therapeutic agents may be prostaglandin E2 (PGE2). PGE2 may increase CXCL12 expression and/or promote stem cell proliferation.

Dosage regimens of the composition may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. The composition may be formulated in a dosage unit form for ease of administration and uniformity of dosage. Dosage unit form as used herein refers to physically discrete units suited as unitary dosages for the subject to be treated; each unit containing a predetermined quantity of bone marrow stromal cells calculated to produce the desired therapeutic effect in association with the required pharmaceutical carrier. The specification for the dosage unit forms are dictated by and directly dependent on (a) the unique characteristics of the bone marrow stromal cells and the particular therapeutic or prophylactic effect to be achieved, and (b) the limitations inherent in the art of using such bone marrow stromal cells for the treatment of individuals.

b. Transforming Growth Factor Beta-1 (TGF-β1)

TGF-β1 may be a component in a pharmaceutical composition. The pharmaceutical composition may be administered using the method of treatment described herein.

The pharmaceutical composition may further contain one or more prophylactic and/or therapeutic agents other than TGF-β1. Such prophylactic and/or therapeutic agents may be useful for, or have been used, or are currently being used in the prevention, treatment, management, or amelioration of a disorder, or one or more symptoms thereof. In some embodiments, the one or more prophylactic and/or therapeutic agents may be prostaglandin E2 (PGE2). PGE2 may increase CXCL12 expression and/or promote stem cell proliferation.

Dosage regimens of the composition may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. The composition may be formulated in a dosage unit form for ease of administration and uniformity of dosage. Dosage unit form as used herein refers to physically discrete units suited as unitary dosages for the subject to be treated; each unit containing a predetermined quantity of TGF-β1 calculated to produce the desired therapeutic effect in association with the required pharmaceutical carrier. The specification for the dosage unit forms are dictated by and directly dependent on (a) the unique characteristics of the TGF-β1 and the particular therapeutic or prophylactic effect to be achieved, and (b) the limitations inherent in the art of using TGF-β1 for the treatment of individuals.

4. METHOD OF TREATMENT

Also provided herein is a method of treating pain in a subject in need thereof. The method of treatment may include administering the pharmaceutical composition. The method of treatment may include administration of the bone marrow stromal cells. The method of treatment may include administration of TGF-β1. The bone marrow stromal cells may be administered to the subject prior to administration of the TGF-β1. The TGF-β1 may be administered to the subject prior to the administration of the bone marrow stromal cells. The bone marrow stromal cells and the TGF-β1 may be administered to the subject concurrently.

The amount of TGF-β1 to be administered may be about 0.1 mg/kg to about 1000 mg/kg, about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg. A skilled practitioner, such as a physician (e.g., a neurologist) can readily determine optimal dosage levels. The TGF-β1 may be administered once per day, twice per day, once per week, or at a timing prescribed by a skilled artisan. The skilled artisan will appreciate that certain factors influence dosage and timing required to effectively treat a patient, including but not limited to the severity of the pain, injury, disease, previous treatments, the general health of the patient, the age of the patient, and other diseases or injuries present.

The method of treatment may include administration of about $0.5 \times 10^5$ to about $5.0 \times 10^7$, about $0.6 \times 10^5$ to about $5.0 \times 10^7$, about $0.7 \times 10^5$ to about $5.0 \times 10^7$, about $0.8 \times 10^5$ to about $5.0 \times 10^7$, about $0.9 \times 10^5$ to about $5.0 \times 10^7$, about $1.0 \times 10^5$ to about $5.0 \times 10^7$, about $1.5 \times 10^5$ to about $5.0 \times 10^7$, about $2.0 \times 10^5$ to about $5.0 \times 10^7$, about $2.5 \times 10^5$ to about $5.0 \times 10^7$, about $3.0 \times 10^5$ to about $5.0 \times 10^7$, about $3.5 \times 10^5$ to about $5.0 \times 10^7$, about $4.0 \times 10^5$ to about $5.0 \times 10^7$, about $4.5 \times 10^5$ to about $5.0 \times 10^7$, about $5.0 \times 10^5$ to about $5.0 \times 10^7$, about $5.5 \times 10^5$ to about $5.0 \times 10^7$, about $6.0 \times 10^5$ to about $5.0 \times 10^7$, about $6.5 \times 10^5$ to about $5.0 \times 10^7$, about $7.0 \times 10^5$ to about $5.0 \times 10^7$, about $7.5 \times 10^5$ to about $5.0 \times 10^7$, about $8.0 \times 10^5$ to about $5.0 \times 10^7$, about $8.5 \times 10^5$ to about $5.0 \times 10^7$, about $9.0 \times 10^5$ to about $5.0 \times 10^7$, about $9.5 \times 10^5$ to about $5.0 \times 10^7$, about $1.0 \times 10^6$ to about $5.0 \times 10^7$, about $1.5 \times 10^6$ to about $5.0 \times 10^7$, about $2.0 \times 10^6$ to about $5.0 \times 10^7$, about $2.5 \times 10^6$ to about $5.0 \times 10^7$, about $3.0 \times 10^6$ to about $5.0 \times 10^7$, about $3.5 \times 10^6$ to about $5.0 \times 10^7$, about $4.0 \times 10^6$ to about $5.0 \times 10^7$, about $4.5 \times 10^6$ to about $5.0 \times 10^7$, about $5.0 \times 10^6$ to about $5.0 \times 10^7$, about $5.5 \times 10^6$ to about $5.0 \times 10^7$, about $6.0 \times 10^6$ to about $5.0 \times 10^7$, about $6.5 \times 10^6$ to about $5.0 \times 10^7$, about $7.0 \times 10^6$ to about $5.0 \times 10^7$, about $7.5 \times 10^6$ to about $5.0 \times 10^7$, about $8.0 \times 10^6$ to about $5.0 \times 10^7$, about $8.5 \times 10^6$ to about $5.0 \times 10^7$, about $9.0 \times 10^6$ to about $5.0 \times 10^7$, about $9.5 \times 10^6$ to about $5.0 \times 10^7$, about $1.0 \times 10^7$ to about $5.0 \times 10^7$, about $1.5 \times 10^7$ to about $5.0 \times 10^7$, about $2.0 \times 10^7$ to about $5.0 \times 10^7$, about $2.5 \times 10^7$ to about $5.0 \times 10^7$, about $3.0 \times 10^7$ to about $5.0 \times 10^7$, about $3.5 \times 10^7$ to about $5.0 \times 10^7$, about $4.0 \times 10^7$ to about $5.0 \times 10^7$, about $4.5 \times 10^7$ to about $5.0 \times 10^7$, about $5.0 \times 10^7$ to about $4.5 \times 10^7$, about $0.5 \times 10^5$ to about $4.0 \times 10^7$, about $0.5 \times 10^5$ to about $3.5 \times 10^7$, about $0.5 \times 10^5$ to about $3.0 \times 10^7$, about $0.5 \times 10^5$ to about $2.5 \times 10^7$, about $0.5 \times 10^5$ to about $2.0 \times 10^7$, about $0.5 \times 10^5$ to about $1.5 \times 10^7$, about $0.5 \times 10^5$ to about $1.0 \times 10^7$, about $0.5 \times 10^5$ to about $9.5 \times 10^6$, about $0.5 \times 10^5$ to about $9.0 \times 10^6$, about $0.5 \times 10^5$ to about $8.5 \times 10^6$, about $0.5 \times 10^5$ to about $8.0 \times 10^6$, about $0.5 \times 10^5$ to about $7.5 \times 10^6$, about $0.5 \times 10^5$ to about $7.0 \times 10^6$, about $0.5 \times 10^5$ to about $6.5 \times 10^6$, about $0.5 \times 10^5$ to about $6.0 \times 10^6$, about $0.5 \times 10^5$ to about $5.5 \times 10^6$, about $0.5 \times 10^5$ to about $5.0 \times 10^6$, about $0.5 \times 10^5$ to about $4.5 \times 10^6$, about $0.5 \times 10^5$ to about $4.0 \times 10^6$, about $0.5 \times 10^5$ to about $3.5 \times 10^6$, about $0.5 \times 10^5$ to about $3.0 \times 10^6$, about $0.5 \times 10^5$ to about $2.5 \times 10^6$, about $0.5 \times 10^5$ to about $2.0 \times 10^6$, $0.5 \times 10^5$ to about $1.5 \times 10^6$, about $0.5 \times 10^5$ to about $1.0 \times 10^6$, about $0.5 \times 10^5$ to about $9.5 \times 10^5$, about $0.5 \times 10^5$ to about $9.0 \times 10^5$, about $0.5 \times 10^5$ to about $8.5 \times 10^5$, about $0.5 \times 10^5$ to about $8.0 \times 10^5$, about $0.5 \times 10^5$ to about $7.5 \times 10^5$, about $0.5 \times 10^5$ to about $7.0 \times 10^5$, about $0.5 \times 10^5$ to about $6.5 \times 10^5$, about $0.5 \times 10^5$ to about $6.0 \times 10^5$, about $0.5 \times 10^5$ to about $5.5 \times 10^5$, about $0.5 \times 10^5$ to about $5.0 \times 10^5$, about $0.5 \times 10^5$ to about $4.5 \times 10^5$, about $0.5 \times 10^5$ to about $4.0 \times 10^5$, about $0.5 \times 10^5$ to about $3.5 \times 10^5$, about $0.5 \times 10^5$ to about $3.0 \times 10^5$, about $0.5 \times 10^5$ to about $2.5 \times 10^5$, about 0.5×10⁵ to about 2.0×10⁵, about 0.5×10⁵ to about 1.5×10⁵, about 0.5×10⁵ to about 1.0×10⁵, about 0.6×10⁵ to about 4.5×10⁷, about 0.7×10⁵ to about 4.0×10⁷, about 0.8×10⁵ to about 3.5×10⁷, about 0.9×10⁵ to about 3.0×10⁷, about 1.0×10⁵ to about 2.5×10⁷, about 1.5×10⁵ to about 2.0×10⁷, about 2.0×10⁵ to about 1.5×10⁷, about 2.5×10⁵ to about 1.0×10⁷, about 3.0×10⁵ to about 9.5×10⁶, about 3.5×10⁵ to about 9.0×10⁶, about 4.0×10⁵ to about 8.5×10⁶, about 4.5×10⁵ to about 8.0×10⁶, about 5.0×10⁵ to about 7.5×10⁶, about 5.5×10⁵ to about 7.0×10⁶, about 6.0×10⁵ to about 6.5×10⁶, about 6.5×10⁵ to about 6.0×10⁶, about 7.0×10⁵ to about 5.5×10⁶, about 7.5×10⁵ to about 5.0×10⁶, about 8.0×10⁵ to about 4.5×10⁶, about 8.5×10⁵ to about 4.0×10⁶, about 9.0×10⁵ to about 3.5×10⁶, about 9.5×10⁵ to about 3.0×10⁶, about 1.0×10⁶ to about 2.5×10⁶, about 1.5×10⁶ to about 2.0×10⁶, or about 0.5×10⁵, about 0.6×10⁵, about 0.7×10⁵, about 0.8×10⁵, about 0.9×10⁵, about 1.0×10⁵, about 1.1×10⁵, about 1.2×10⁵, about 1.3×10⁵, about 1.4×10⁵, about 1.5×10⁵, about 1.6×10⁵, about 1.7×10⁵, about 1.8×10⁵, about 1.9×10⁵, about 2.0×10⁵, about 2.1×10⁵, about 2.2×10⁵, about 2.3×10⁵, about 2.4×10⁵, about 2.5×10⁵, about 2.6×10⁵, about 2.7×10⁵, about 2.8×10⁵, about 2.9×10⁵, about 3.0×10⁵, about 3.1×10⁵, about 3.2×10⁵, about 3.3×10⁵, about 3.4×10⁵, about 3.5×10⁵, about 3.6×10⁵, about 3.7×10⁵, about 3.8×10⁵, about 3.9×10⁵, about 4.0×10⁵, about 4.1×10⁵, about 4.2×10⁵, about 4.3×10⁵, about 4.4×10⁵, about 4.5×10⁵, about 4.6×10⁵, about 4.7×10⁵, about 4.8×10⁵, about 4.9×10⁵, about 5.0×10⁵, about 5.1×10⁵, about 5.2×10⁵, about 5.3×10⁵, about 5.4×10⁵, about 5.5×10⁵, about 5.6×10⁵, about 5.7×10⁵, about 5.8×10⁵, about 5.9×10⁵, about 6.0×10⁵, about 6.1×10⁵, about 6.2×10⁵, about 6.3×10⁵, about 6.4×10⁵, about 6.5×10⁵, about 6.6×10⁵, about 6.7×10⁵, about 6.8×10⁵, about 6.9×10⁵, about 7.0×10⁵, about 7.1×10⁵, about 7.2×10⁵, about 7.3×10⁵, about 7.4×10⁵, about 7.5×10⁵, about 7.6×10⁵, about 7.7×10⁵, about 7.8×10⁵, about 7.9×10⁵, about 8.0×10⁵, about 8.1×10⁵, about 8.2×10⁵, about 8.3×10⁵, about 8.4×10⁵, about 8.5×10⁵, about 8.6×10⁵, about 8.7×10⁵, about 8.8×10⁵, about 8.9×10⁵, about 9.0×10⁵, about 9.1×10⁵, about 9.2×10⁵, about 9.3×10⁵, about 9.4×10⁵, about 9.5×10⁵, about 9.6×10⁵, about 9.7×10⁵, about 9.8×10⁵, about 9.9×10⁵, about 1.0×10⁶, about 1.1×10⁶, about 1.2×10⁶, about 1.3×10⁶, about 1.4×10⁶, about 1.5×10⁶, about 1.6×10⁶, about 1.7×10⁶, about 1.8×10⁶, about 1.9×10⁶, about 2.0×10⁶, about 2.1×10⁶, about 2.2×10⁶, about 2.3×10⁶, about 2.4×10⁶, about 2.5×10⁶, about 2.6×10⁶, about 2.7×10⁶, about 2.8×10⁶, about 2.9×10⁶, about 3.0×10⁶, about 3.1×10⁶, about 3.2×10⁶, about 3.3×10⁶, about 3.4×10⁶, about 3.5×10⁶, about 3.6×10⁶, about 3.7×10⁶, about 3.8×10⁶, about 3.9×10⁶, about 4.0×10⁶, about 4.1×10⁶, about 4.2×10⁶, about 4.3×10⁶, about 4.4×10⁶, about 4.5×10⁶, about 4.6×10⁶, about 4.7×10⁶, about 4.8×10⁶, about 4.9×10⁶, about 5.0×10⁶, about 5.1×10⁶, about 5.2×10⁶, about 5.3×10⁶, about 5.4×10⁶, about 5.5×10⁶, about 5.6×10⁶, about 5.7×10⁶, about 5.8×10⁶, about 5.9×10⁶, about 6.0×10⁶, about 6.1×10⁶, about 6.2×10⁶, about 6.3×10⁶, about 6.4×10⁶, about 6.5×10⁶, about 6.6×10⁶, about 6.7×10⁶, about 6.8×10⁶, about 6.9×10⁶, about 7.0×10⁶, about 7.1×10⁶, about 7.2×10⁶, about 7.3×10⁶, about 7.4×10⁶, about 7.5×10⁶, about 7.6×10⁶, about 7.7×10⁶, about 7.8×10⁶, about 7.9×10⁶, about 8.0×10⁶, about 8.1×10⁶, about 8.2×10⁶, about 8.3×10⁶, about 8.4×10⁶, about 8.5×10⁶, about 8.6×10⁶, about 8.7×10⁶, about 8.8×10⁶, about 8.9×10⁶, about 9.0×10⁶, about 9.1×10⁶, about 9.2×10⁶, about 9.3×10⁶, about 9.4×10⁶, about 9.5×10⁶, about 9.6×10⁶, about 9.7×10⁶, about 9.8×10⁶, about 9.9×10⁶, about 1.0×10⁷, about 1.1×10⁷, about 1.2×10⁷, about 1.3×10⁷, about 1.4×10⁷, about 1.5×10⁷, about 1.6×10⁷, about 1.7×10⁷, about 1.8×10⁷, about 1.9×10⁷, about 2.0×10⁷, about 2.1×10⁷, about 2.2×10⁷, about 2.3×10⁷, about 2.4×10⁷, about 2.5×10⁷, about 2.6×10⁷, about 2.7×10⁷, about 2.8×10⁷, about 2.9×10⁷, about 3.0×10⁷, about 3.1×10⁷, about 3.2×10⁷, about 3.3×10⁷, about 3.4×10⁷, about 3.5×10⁷, about 3.6×10⁷, about 3.7×10⁷, about 3.8×10⁷, about 3.9×10⁷, about 4.0×10⁷, about 4.1×10⁷, about 4.2×10⁷, about 4.3×10⁷, about 4.4×10⁷, about 4.5×10⁷, about 4.6×10⁷, about 4.7×10⁷, about 4.8×10⁷, about 4.9×10⁷, or about 5.0×10⁷ bone marrow stromal cells to the subject.

The method of treatment may include administration of at least about 0.5×10⁵ to about 5.0×10⁷, about 0.6×10⁵ to about 5.0×10⁷, about 0.7×10⁵ to about 5.0×10⁷, about 0.8×10⁵ to about 5.0×10⁷, about 0.9×10⁵ to about 5.0×10⁷, about 1.0×10⁵ to about 5.0×10⁷, about 1.5×10⁵ to about 5.0×10⁷, about 2.0×10⁵ to about 5.0×10⁷, about 2.5×10⁵ to about 5.0×10⁷, about 3.0×10⁵ to about 5.0×10⁷, about 3.5×10⁵ to about 5.0×10⁷, about 4.0×10⁵ to about 5.0×10⁷, about 4.5×10⁵ to about 5.0×10⁷, about 5.0×10⁵ to about 5.0×10⁷, about 5.5×10⁵ to about 5.0×10⁷, about 6.0×10⁵ to about 5.0×10⁷, about 6.5×10⁵ to about 5.0×10⁷, about 7.0×10⁵ to about 5.0×10⁷, about 7.5×10⁵ to about 5.0×10⁷, about 8.0×10⁵ to about 5.0×10⁷, about 8.5×10⁵ to about 5.0×10⁷, about 9.0×10⁵ to about 5.0×10⁷, about 9.5×10⁵ to about 5.0×10⁷, about 1.0×10⁶ to about 5.0×10⁷, about 1.5×10⁶ to about 5.0×10⁷, about 2.0×10⁶ to about 5.0×10⁷, about 2.5×10⁶ to about 5.0×10⁷, about 3.0×10⁶ to about 5.0×10⁷, about 3.5×10⁶ to about 5.0×10⁷, about 4.0×10⁶ to about 5.0×10⁷, about 4.5×10⁶ to about 5.0×10⁷, about 5.0×10⁶ to about 5.0×10⁷, about 5.5×10⁶ to about 5.0×10⁷, about 6.0×10⁶ to about 5.0×10⁷, about 6.5×10⁶ to about 5.0×10⁷, about 7.0×10⁶ to about 5.0×10⁷, about 7.5×10⁶ to about 5.0×10⁷, about 8.0×10⁶ to about 5.0×10⁷, about 8.5×10⁶ to about 5.0×10⁷, about 9.0×10⁶ to about 5.0×10⁷, about 9.5×10⁶ to about 5.0×10⁷, about 1.0×10⁷ to about 5.0×10⁷, about 1.5×10⁷ to about 5.0×10⁷, about 2.0×10⁷ to about 5.0×10⁷, about 2.5×10⁷ to about 5.0×10⁷, about 3.0×10⁷ to about 5.0×10⁷, about 3.5×10⁷ to about 5.0×10⁷, about 4.0×10⁷ to about 5.0×10⁷, about 4.5×10⁷ to about 5.0×10⁷, about 0.5×10⁵ to about 4.5×10⁷, about 0.5×10⁵ to about 4.0×10⁷, about 0.5×10⁵ to about 3.5×10⁷, about 0.5×10⁵ to about 3.0×10⁷, about 0.5×10⁵ to about 2.5×10⁷, about 0.5×10⁵ to about 2.0×10⁷, about 0.5×10⁵ to about 1.5×10⁷, about 0.5×10⁵ to about 1.0×10⁷, about 0.5×10⁵ to about 9.5×10⁶, about 0.5×10⁵ to about 9.0×10⁶, about 0.5×10⁵ to about 8.5×10⁶, about 0.5×10⁵ to about 8.0×10⁶, about 0.5×10⁵ to about 7.5×10⁶, about 0.5×10⁵ to about 7.0×10⁶, about 0.5×10⁵ to about 6.5×10⁶, about 0.5×10⁵ to about 6.0×10⁶, about 0.5×10⁵ to about 5.5×10⁶, about 0.5×10⁵ to about 5.0×10⁶, about 0.5×10⁵ to about 4.5×10⁶, about 0.5×10⁵ to about 4.0×10⁶, about 0.5×10⁵ to about 3.5×10⁶, about 0.5×10⁵ to about 3.0×10⁶, about 0.5×10⁵ to about 2.5×10⁶, about 0.5×10⁵ to about 2.0×10⁶, 0.5×10⁵ to about 1.5×10⁶, about 0.5×10⁵ to about 1.0×10⁶, about 0.5×10⁵ to about 9.5×10⁵, about 0.5×10⁵ to about 9.0×10⁵, about 0.5×10⁵ to about 8.5×10⁵, about 0.5×10⁵ to about 8.0×10⁵, about 0.5×10⁵ to about 7.5×10⁵, about 0.5×10⁵ to about 7.0×10⁵, about 0.5×10⁵ to about 6.5×10⁵, about 0.5×10⁵ to about 6.0×10⁵, about 0.5×10⁵ to about 5.5×10⁵, about 0.5×10⁵ to about 5.0×10⁵, about 0.5×10⁵ to about 4.5×10⁵, about 0.5×10⁵ to about 4.0×10⁵, about 0.5×10⁵ to about 3.5×10⁵, about 0.5×10⁵ to about 3.0×10⁵, about 0.5×10⁵ to about 2.5×10⁵, about 0.5×10⁵ to about 2.0×10⁵, about 0.5×10⁵ to about 1.5×10⁵, about 0.5×10⁵ to about 1.0×10⁵, about 0.6×10⁵ to about 4.5×10⁷, about 0.7×10⁵ to about 4.0×10⁷, about 0.8×10⁵ to about 3.5×10⁷, about 0.9×10⁵ to about 3.0×10⁷, about 1.0×10⁵ to about 2.5×10⁷, about 1.5×10⁵ to about 2.0×10⁷, about $2.0 \times 10^5$ to about $1.5 \times 10^7$, about $2.5 \times 10^5$ to about $1.0 \times 10^7$, about $3.0 \times 10^5$ to about $9.5 \times 10^6$, about $3.5 \times 10^5$ to about $9.0 \times 10^6$, about $4.0 \times 10^5$ to about $8.5 \times 10^6$, about $4.5 \times 10^5$ to about $8.0 \times 10^6$, about $5.0 \times 10^5$ to about $7.5 \times 10^6$, about $5.5 \times 10^5$ to about $7.0 \times 10^6$, about $6.0 \times 10^5$ to about $6.5 \times 10^6$, about $6.5 \times 10^5$ to about $6.0 \times 10^6$, about $7.0 \times 10^5$ to about $5.5 \times 10^6$, about $7.5 \times 10^5$ to about $5.0 \times 10^6$, about $8.0 \times 10^5$ to about $4.5 \times 10^6$, about $8.5 \times 10^5$ to about $4.0 \times 10^6$, about $9.0 \times 10^5$ to about $3.5 \times 10^6$, about $9.5 \times 10^5$ to about $3.0 \times 10^6$, about $1.0 \times 10^6$ to about $2.5 \times 10^6$, about $1.5 \times 10^6$ to about $2.0 \times 10^6$, or about $0.5 \times 10^5$, about $0.6 \times 10^5$, about $0.7 \times 10^5$, about $0.8 \times 10^5$, about $0.9 \times 10^5$, about $1.0 \times 10^5$, about $1.1 \times 10^5$, about $1.2 \times 10^5$, about $1.3 \times 10^5$, about $1.4 \times 10^5$, about $1.5 \times 10^5$, about $1.6 \times 10^5$, about $1.7 \times 10^5$, about $1.8 \times 10^5$, about $1.9 \times 10^5$, about $2.0 \times 10^5$, about $2.1 \times 10^5$, about $2.2 \times 10^5$, about $2.3 \times 10^5$, about $2.4 \times 10^5$, about $2.5 \times 10^5$, about $2.6 \times 10^5$, about $2.7 \times 10^5$, about $2.8 \times 10^5$, about $2.9 \times 10^5$, about $3.0 \times 10^5$, about $3.1 \times 10^5$, about $3.2 \times 10^5$, about $3.3 \times 10^5$, about $3.4 \times 10^5$, about $3.5 \times 10^5$, about $3.6 \times 10^5$, about $3.7 \times 10^5$, about $3.8 \times 10^5$, about $3.9 \times 10^5$, about $4.0 \times 10^5$, about $4.1 \times 10^5$, about $4.2 \times 10^5$, about $4.3 \times 10^5$, about $4.4 \times 10^5$, about $4.5 \times 10^5$, about $4.6 \times 10^5$, about $4.7 \times 10^5$, about $4.8 \times 10^5$, about $4.9 \times 10^5$, about $5.0 \times 10^5$, about $5.1 \times 10^5$, about $5.2 \times 10^5$, about $5.3 \times 10^5$, about $5.4 \times 10^5$, about $5.5 \times 10^5$, about $5.6 \times 10^5$, about $5.7 \times 10^5$, about $5.8 \times 10^5$, about $5.9 \times 10^5$, about $6.0 \times 10^5$, about $6.1 \times 10^5$, about $6.2 \times 10^5$, about $6.3 \times 10^5$, about $6.4 \times 10^5$, about $6.5 \times 10^5$, about $6.6 \times 10^5$, about $6.7 \times 10^5$, about $6.8 \times 10^5$, about $6.9 \times 10^5$, about $7.0 \times 10^5$, about $7.1 \times 10^5$, about $7.2 \times 10^5$, about $7.3 \times 10^5$, about $7.4 \times 10^5$, about $7.5 \times 10^5$, about $7.6 \times 10^5$, about $7.7 \times 10^5$, about $7.8 \times 10^5$, about $7.9 \times 10^5$, about $8.0 \times 10^5$, about $8.1 \times 10^5$, about $8.2 \times 10^5$, about $8.3 \times 10^5$, about $8.4 \times 10^5$, about $8.5 \times 10^5$, about $8.6 \times 10^5$, about $8.7 \times 10^5$, about $8.8 \times 10^5$, about $8.9 \times 10^5$, about $9.0 \times 10^5$, about $9.1 \times 10^5$, about $9.2 \times 10^5$, about $9.3 \times 10^5$, about $9.4 \times 10^5$, about $9.5 \times 10^5$, about $9.6 \times 10^5$, about $9.7 \times 10^5$, about $9.8 \times 10^5$, about $9.9 \times 10^5$, about $1.0 \times 10^6$, about $1.1 \times 10^6$, about $1.2 \times 10^6$, about $1.3 \times 10^6$, about $1.4 \times 10^6$, about $1.5 \times 10^6$, about $1.6 \times 10^6$, about $1.7 \times 10^6$, about $1.8 \times 10^6$, about $1.9 \times 10^6$, about $2.0 \times 10^6$, about $2.1 \times 10^6$, about $2.2 \times 10^6$, about $2.3 \times 10^6$, about $2.4 \times 10^6$, about $2.5 \times 10^6$, about $2.6 \times 10^6$, about $2.7 \times 10^6$, about $2.8 \times 10^6$, about $2.9 \times 10^6$, about $3.0 \times 10^6$, about $3.1 \times 10^6$, about $3.2 \times 10^6$, about $3.3 \times 10^6$, about $3.4 \times 10^6$, about $3.5 \times 10^6$, about $3.6 \times 10^6$, about $3.7 \times 10^6$, about $3.8 \times 10^6$, about $3.9 \times 10^6$, about $4.0 \times 10^6$, about $4.1 \times 10^6$, about $4.2 \times 10^6$, about $4.3 \times 10^6$, about $4.4 \times 10^6$, about $4.5 \times 10^6$, about $4.6 \times 10^6$, about $4.7 \times 10^6$, about $4.8 \times 10^6$, about $4.9 \times 10^6$, about $5.0 \times 10^6$, about $5.1 \times 10^6$, about $5.2 \times 10^6$, about $5.3 \times 10^6$, about $5.4 \times 10^6$, about $5.5 \times 10^6$, about $5.6 \times 10^6$, about $5.7 \times 10^6$, about $5.8 \times 10^6$, about $5.9 \times 10^6$, about $6.0 \times 10^6$, about $6.1 \times 10^6$, about $6.2 \times 10^6$, about $6.3 \times 10^6$, about $6.4 \times 10^6$, about $6.5 \times 10^6$, about $6.6 \times 10^6$, about $6.7 \times 10^6$, about $6.8 \times 10^6$, about $6.9 \times 10^6$, about $7.0 \times 10^6$, about $7.1 \times 10^6$, about $7.2 \times 10^6$, about $7.3 \times 10^6$, about $7.4 \times 10^6$, about $7.5 \times 10^6$, about $7.6 \times 10^6$, about $7.7 \times 10^6$, about $7.8 \times 10^6$, about $7.9 \times 10^6$, about $8.0 \times 10^6$, about $8.1 \times 10^6$, about $8.2 \times 10^6$, about $8.3 \times 10^6$, about $8.4 \times 10^6$, about $8.5 \times 10^6$, about $8.6 \times 10^6$, about $8.7 \times 10^6$, about $8.8 \times 10^6$, about $8.9 \times 10^6$, about $9.0 \times 10^6$, about $9.1 \times 10^6$, about $9.2 \times 10^6$, about $9.3 \times 10^6$, about $9.4 \times 10^6$, about $9.5 \times 10^6$, about $9.6 \times 10^6$, about $9.7 \times 10^6$, about $9.8 \times 10^6$, about $9.9 \times 10^6$, about $1.0 \times 10^7$, about $1.1 \times 10^7$, about $1.2 \times 10^7$, about $1.3 \times 10^7$, about $1.4 \times 10^7$, about $1.5 \times 10^7$, about $1.6 \times 10^7$, about $1.7 \times 10^7$, about $1.8 \times 10^7$, about $1.9 \times 10^7$, about $2.0 \times 10^7$, about $2.1 \times 10^7$, about $2.2 \times 10^7$, about $2.3 \times 10^7$, about $2.4 \times 10^7$, about $2.5 \times 10^7$, about $2.6 \times 10^7$, about $2.7 \times 10^7$, about $2.8 \times 10^7$, about $2.9 \times 10^7$, about $3.0 \times 10^7$, about $3.1 \times 10^7$, about $3.2 \times 10^7$, about $3.3 \times 10^7$, about $3.4 \times 10^7$, about $3.5 \times 10^7$, about $3.6 \times 10^7$, about $3.7 \times 10^7$, about $3.8 \times 10^7$, about $3.9 \times 10^7$, about $4.0 \times 10^7$, about $4.1 \times 10^7$, about $4.2 \times 10^7$, about $4.3 \times 10^7$, about $4.4 \times 10^7$, about $4.5 \times 10^7$, about $4.6 \times 10^7$, about $4.7 \times 10^7$, about $4.8 \times 10^7$, about $4.9 \times 10^7$, or about $5.0 \times 10^7$ bone marrow stromal cells to the subject.

The method of treatment may include administration of less than about $0.5 \times 10^5$ to about $5.0 \times 10^7$, about $0.6 \times 10^5$ to about $5.0 \times 10^7$, about $0.7 \times 10^5$ to about $5.0 \times 10^7$, about $0.8 \times 10^5$ to about $5.0 \times 10^7$, about $0.9 \times 10^5$ to about $5.0 \times 10^7$, about $1.0 \times 10^5$ to about $5.0 \times 10^7$, about $1.5 \times 10^5$ to about $5.0 \times 10^7$, about $2.0 \times 10^5$ to about $5.0 \times 10^7$, about $2.5 \times 10^5$ to about $5.0 \times 10^7$, about $3.0 \times 10^5$ to about $5.0 \times 10^7$, about $3.5 \times 10^5$ to about $5.0 \times 10^7$, about $4.0 \times 10^5$ to about $5.0 \times 10^7$, about $4.5 \times 10^5$ to about $5.0 \times 10^7$, about $5.0 \times 10^5$ to about $5.0 \times 10^7$, about $5.5 \times 10^5$ to about $5.0 \times 10^7$, about $6.0 \times 10^5$ to about $5.0 \times 10^7$, about $6.5 \times 10^5$ to about $5.0 \times 10^7$, about $7.0 \times 10^5$ to about $5.0 \times 10^7$, about $7.5 \times 10^5$ to about $5.0 \times 10^7$, about $8.0 \times 10^5$ to about $5.0 \times 10^7$, about $8.5 \times 10^5$ to about $5.0 \times 10^7$, about $9.0 \times 10^5$ to about $5.0 \times 10^7$, about $9.5 \times 10^5$ to about $5.0 \times 10^7$, about $1.0 \times 10^6$ to about $5.0 \times 10^7$, about $1.5 \times 10^6$ to about $5.0 \times 10^7$, about $2.0 \times 10^6$ to about $5.0 \times 10^7$, about $2.5 \times 10^6$ to about $5.0 \times 10^7$, about $3.0 \times 10^6$ to about $5.0 \times 10^7$, about $3.5 \times 10^6$ to about $5.0 \times 10^7$, about $4.0 \times 10^6$ to about $5.0 \times 10^7$, about $4.5 \times 10^6$ to about $5.0 \times 10^7$, about $5.0 \times 10^6$ to about $5.0 \times 10^7$, about $5.5 \times 10^6$ to about $5.0 \times 10^7$, about $6.0 \times 10^6$ to about $5.0 \times 10^7$, about $6.5 \times 10^6$ to about $5.0 \times 10^7$, about $7.0 \times 10^6$ to about $5.0 \times 10^7$, about $7.5 \times 10^6$ to about $5.0 \times 10^7$, about $8.0 \times 10^6$ to about $5.0 \times 10^7$, about $8.5 \times 10^6$ to about $5.0 \times 10^7$, about $9.0 \times 10^6$ to about $5.0 \times 10^7$, about $9.5 \times 10^6$ to about $5.0 \times 10^7$, about $1.0 \times 10^7$ to about $5.0 \times 10^7$, about $1.5 \times 10^7$ to about $5.0 \times 10^7$, about $2.0 \times 10^7$ to about $5.0 \times 10^7$, about $2.5 \times 10^7$ to about $5.0 \times 10^7$, about $3.0 \times 10^7$ to about $5.0 \times 10^7$, about $3.5 \times 10^7$ to about $5.0 \times 10^7$, about $4.0 \times 10^7$ to about $5.0 \times 10^7$, about $4.5 \times 10^7$ to about $5.0 \times 10^7$, about $0.5 \times 10^5$ to about $4.5 \times 10^7$, about $0.5 \times 10^5$ to about $4.0 \times 10^7$, about $0.5 \times 10^5$ to about $3.5 \times 10^7$, about $0.5 \times 10^5$ to about $3.0 \times 10^7$, about $0.5 \times 10^5$ to about $2.5 \times 10^7$, about $0.5 \times 10^5$ to about $2.0 \times 10^7$, about $0.5 \times 10^5$ to about $1.5 \times 10^7$, about $0.5 \times 10^5$ to about $1.0 \times 10^7$, about $0.5 \times 10^5$ to about $9.5 \times 10^6$, about $0.5 \times 10^5$ to about $9.0 \times 10^6$, about $0.5 \times 10^5$ to about $8.5 \times 10^6$, about $0.5 \times 10^5$ to about $8.0 \times 10^6$, about $0.5 \times 10^5$ to about $7.5 \times 10^6$, about $0.5 \times 10^5$ to about $7.0 \times 10^6$, about $0.5 \times 10^5$ to about $6.5 \times 10^6$, about $0.5 \times 10^5$ to about $6.0 \times 10^6$, about $0.5 \times 10^5$ to about $5.5 \times 10^6$, about $0.5 \times 10^5$ to about $5.0 \times 10^6$, about $0.5 \times 10^5$ to about $4.5 \times 10^6$, about $0.5 \times 10^5$ to about $4.0 \times 10^6$, about $0.5 \times 10^5$ to about $3.5 \times 10^6$, about $0.5 \times 10^5$ to about $3.0 \times 10^6$, about $0.5 \times 10^5$ to about $2.5 \times 10^6$, about $0.5 \times 10^5$ to about $2.0 \times 10^6$, $0.5 \times 10^5$ to about $1.5 \times 10^6$, about $0.5 \times 10^5$ to about $1.0 \times 10^6$, about $0.5 \times 10^5$ to about $9.5 \times 10^5$, about $0.5 \times 10^5$ to about $9.0 \times 10^5$, about $0.5 \times 10^5$ to about $8.5 \times 10^5$, about $0.5 \times 10^5$ to about $8.0 \times 10^5$, about $0.5 \times 10^5$ to about $7.5 \times 10^5$, about $0.5 \times 10^5$ to about $7.0 \times 10^5$, about $0.5 \times 10^5$ to about $6.5 \times 10^5$, about $0.5 \times 10^5$ to about $6.0 \times 10^5$, about $0.5 \times 10^5$ to about $5.5 \times 10^5$, about $0.5 \times 10^5$ to about $5.0 \times 10^5$, about $0.5 \times 10^5$ to about $4.5 \times 10^5$, about $0.5 \times 10^5$ to about $4.0 \times 10^5$, about $0.5 \times 10^5$ to about $3.5 \times 10^5$, about $0.5 \times 10^5$ to about $3.0 \times 10^5$, about $0.5 \times 10^5$ to about $2.5 \times 10^5$, about $0.5 \times 10^5$ to about $2.0 \times 10^5$, about $0.5 \times 10^5$ to about $1.5 \times 10^5$, about $0.5 \times 10^5$ to about $1.0 \times 10^5$, about $0.6 \times 10^5$ to about $4.5 \times 10^7$, about $0.7 \times 10^5$ to about $4.0 \times 10^7$, about $0.8 \times 10^5$ to about $3.5 \times 10^7$, about $0.9 \times 10^5$ to about $3.0 \times 10^7$, about $1.0 \times 10^5$ to about $2.5 \times 10^7$, about $1.5 \times 10^5$ to about $2.0 \times 10^7$, about $2.0 \times 10^5$ to about $1.5 \times 10^7$, about $2.5 \times 10^5$ to about $1.0 \times 10^7$, about $3.0 \times 10^5$ to about $9.5 \times 10^6$, about $3.5 \times 10^5$ to about $9.0 \times 10^6$, about $4.0 \times 10^5$ to about $8.5 \times 10^6$, about $4.5 \times 10^5$ to about $8.0 \times 10^6$, about $5.0 \times 10^5$ to about $7.5 \times 10^6$, about $5.5 \times 10^5$ to about $7.0 \times 10^6$, about $6.0 \times 10^5$ to about $6.5 \times 10^6$, about $6.5 \times 10^5$ to about $6.0 \times 10^6$, about $7.0 \times 10^5$ to about $5.5 \times 10^6$, about $7.5 \times 10^5$ to about $5.0 \times 10^6$, about $8.0 \times 10^5$ to about $4.5 \times 10^6$, about $8.5 \times 10^5$ to about $4.0 \times 10^6$, about $9.0 \times 10^5$ to about $3.5 \times 10^6$, about $9.5 \times 10^5$ to about $3.0 \times 10^6$, about $1.0 \times 10^6$ to about $2.5 \times 10^6$, about $1.5 \times 10^6$ to about $2.0 \times 10^6$, or about $0.5 \times 10^5$, about $0.6 \times 10^5$, about $0.7 \times 10^5$, about $0.8 \times 10^5$, about $0.9 \times 10^5$, about $1.0 \times 10^5$, about $1.1 \times 10^5$, about $1.2 \times 10^5$, about $1.3 \times 10^5$, about $1.4 \times 10^5$, about $1.5 \times 10^5$, about $1.6 \times 10^5$, about $1.7 \times 10^5$, about $1.8 \times 10^5$, about $1.9 \times 10^5$, about $2.0 \times 10^5$, about $2.1 \times 10^5$, about $2.2 \times 10^5$, about $2.3 \times 10^5$, about $2.4 \times 10^5$, about $2.5 \times 10^5$, about $2.6 \times 10^5$, about $2.7 \times 10^5$, about $2.8 \times 10^5$, about $2.9 \times 10^5$, about $3.0 \times 10^5$, about $3.1 \times 10^5$, about $3.2 \times 10^5$, about $3.3 \times 10^5$, about $3.4 \times 10^5$, about $3.5 \times 10^5$, about $3.6 \times 10^5$, about $3.7 \times 10^5$, about $3.8 \times 10^5$, about $3.9 \times 10^5$, about $4.0 \times 10^5$, about $4.1 \times 10^5$, about $4.2 \times 10^5$, about $4.3 \times 10^5$, about $4.4 \times 10^5$, about $4.5 \times 10^5$, about $4.6 \times 10^5$, about $4.7 \times 10^5$, about $4.8 \times 10^5$, about $4.9 \times 10^5$, about $5.0 \times 10^5$, about $5.1 \times 10^5$, about $5.2 \times 10^5$, about $5.3 \times 10^5$, about $5.4 \times 10^5$, about $5.5 \times 10^5$, about $5.6 \times 10^5$, about $5.7 \times 10^5$, about $5.8 \times 10^5$, about $5.9 \times 10^5$, about $6.0 \times 10^5$, about $6.1 \times 10^5$, about $6.2 \times 10^5$, about $6.3 \times 10^5$, about $6.4 \times 10^5$, about $6.5 \times 10^5$, about $6.6 \times 10^5$, about $6.7 \times 10^5$, about $6.8 \times 10^5$, about $6.9 \times 10^5$, about $7.0 \times 10^5$, about $7.1 \times 10^5$, about $7.2 \times 10^5$, about $7.3 \times 10^5$, about $7.4 \times 10^5$, about $7.5 \times 10^5$, about $7.6 \times 10^5$, about $7.7 \times 10^5$, about $7.8 \times 10^5$, about $7.9 \times 10^5$, about $8.0 \times 10^5$, about $8.1 \times 10^5$, about $8.2 \times 10^5$, about $8.3 \times 10^5$, about $8.4 \times 10^5$, about $8.5 \times 10^5$, about $8.6 \times 10^5$, about $8.7 \times 10^5$, about $8.8 \times 10^5$, about $8.9 \times 10^5$, about $9.0 \times 10^5$, about $9.1 \times 10^5$, about $9.2 \times 10^5$, about $9.3 \times 10^5$, about $9.4 \times 10^5$, about $9.5 \times 10^5$, about $9.6 \times 10^5$, about $9.7 \times 10^5$, about $9.8 \times 10^5$, about $9.9 \times 10^5$, about $1.0 \times 10^6$, about $1.1 \times 10^6$, about $1.2 \times 10^6$, about $1.3 \times 10^6$, about $1.4 \times 10^6$, about $1.5 \times 10^6$, about $1.6 \times 10^6$, about $1.7 \times 10^6$, about $1.8 \times 10^6$, about $1.9 \times 10^6$, about $2.0 \times 10^6$, about $2.1 \times 10^6$, about $2.2 \times 10^6$, about $2.3 \times 10^6$, about $2.4 \times 10^6$, about $2.5 \times 10^6$, about $2.6 \times 10^6$, about $2.7 \times 10^6$, about $2.8 \times 10^6$, about $2.9 \times 10^6$, about $3.0 \times 10^6$, about $3.1 \times 10^6$, about $3.2 \times 10^6$, about $3.3 \times 10^6$, about $3.4 \times 10^6$, about $3.5 \times 10^6$, about $3.6 \times 10^6$, about $3.7 \times 10^6$, about $3.8 \times 10^6$, about $3.9 \times 10^6$, about $4.0 \times 10^6$, about $4.1 \times 10^6$, about $4.2 \times 10^6$, about $4.3 \times 10^6$, about $4.4 \times 10^6$, about $4.5 \times 10^6$, about $4.6 \times 10^6$, about $4.7 \times 10^6$, about $4.8 \times 10^6$, about $4.9 \times 10^6$, about $5.0 \times 10^6$, about $5.1 \times 10^6$, about $5.2 \times 10^6$, about $5.3 \times 10^6$, about $5.4 \times 10^6$, about $5.5 \times 10^6$, about $5.6 \times 10^6$, about $5.7 \times 10^6$, about $5.8 \times 10^6$, about $5.9 \times 10^6$, about $6.0 \times 10^6$, about $6.1 \times 10^6$, about $6.2 \times 10^6$, about $6.3 \times 10^6$, about $6.4 \times 10^6$, about $6.5 \times 10^6$, about $6.6 \times 10^6$, about $6.7 \times 10^6$, about $6.8 \times 10^6$, about $6.9 \times 10^6$, about $7.0 \times 10^6$, about $7.1 \times 10^6$, about $7.2 \times 10^6$, about $7.3 \times 10^6$, about $7.4 \times 10^6$, about $7.5 \times 10^6$, about $7.6 \times 10^6$, about $7.7 \times 10^6$, about $7.8 \times 10^6$, about $7.9 \times 10^6$, about $8.0 \times 10^6$, about $8.1 \times 10^6$, about $8.2 \times 10^6$, about $8.3 \times 10^6$, about $8.4 \times 10^6$, about $8.5 \times 10^6$, about $8.6 \times 10^6$, about $8.7 \times 10^6$, about $8.8 \times 10^6$, about $8.9 \times 10^6$, about $9.0 \times 10^6$, about $9.1 \times 10^6$, about $9.2 \times 10^6$, about $9.3 \times 10^6$, about $9.4 \times 10^6$, about $9.5 \times 10^6$, about $9.6 \times 10^6$, about $9.7 \times 10^6$, about $9.8 \times 10^6$, about $9.9 \times 10^6$, about $1.0 \times 10^7$, about $1.1 \times 10^7$, about $1.2 \times 10^7$, about $1.3 \times 10^7$, about $1.4 \times 10^7$, about $1.5 \times 10^7$, about $1.6 \times 10^7$, about $1.7 \times 10^7$, about $1.8 \times 10^7$, about $1.9 \times 10^7$, about $2.0 \times 10^7$, about $2.1 \times 10^7$, about $2.2 \times 10^7$, about $2.3 \times 10^7$, about $2.4 \times 10^7$, about $2.5 \times 10^7$, about $2.6 \times 10^7$, about $2.7 \times 10^7$, about $2.8 \times 10^7$, about $2.9 \times 10^7$, about $3.0 \times 10^7$, about $3.1 \times 10^7$, about $3.2 \times 10^7$, about $3.3 \times 10^7$, about $3.4 \times 10^7$, about $3.5 \times 10^7$, about $3.6 \times 10^7$, about $3.7 \times 10^7$, about $3.8 \times 10^7$, about $3.9 \times 10^7$, about $4.0 \times 10^7$, about $4.1 \times 10^7$, about $4.2 \times 10^7$, about $4.3 \times 10^7$, about $4.4 \times 10^7$, about $4.5 \times 10^7$, about $4.6 \times 10^7$, about $4.7 \times 10^7$, about $4.8 \times 10^7$, about $4.9 \times 10^7$, or about $5.0 \times 10^7$ bone marrow stromal cells to the subject.

The method of treatment may reduce or suppress the pain in the subject. The method of treatment may reduce or suppress the pain in the subject for at least about 15 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, or 2 years. The method of treating may reduce or suppress the pain in the subject for about 15 minutes to about 12 hours, for about 2 to about 10 hours, for about 2 to about 10 days, for about 2 to about 10 months, or for about 1 to about 2 years.

The method of treatment may also protect the peripheral nervous system, central nervous system, or a combination thereof from injury. The method of treatment may protect neurons from injury. The method of treatment may protect the axons of neurons from injury. The method of treatment may protect dorsal root ganglion neurons from injury. The method of treatment may protect the axons of dorsal root ganglion neurons from injury.

The method of treatment may also reduce inflammation in the subject, for example, but not limited to, neuroinflammation in the peripheral and/or central nervous system.

a. Pain

As described above, the method of treatment may reduce or suppress pain in the subject. The pain may be neuropathic pain, inflammation-related pain, cancer pain, or a combination thereof. The pain may be chronic pain. The pain may be caused by one or more injured neurons. The pain may be caused by one or more neurons with injured axons. The pain may be caused by one or more DRGs. The pain may be caused by one or more injured DRGs. The pain may be caused by one or more inflamed DRGs. The pain may be caused by one or more inflamed DRGs with injured axons. The pain may be caused by one or more DRGs expressing CXCL12. The pain may be caused by a peripheral nerve injury, a central nerve injury, or a combination thereof. The pain may be caused by one or more insults to the peripheral nervous system, central nervous system, or a combination thereof.

The pain may include, but is not limited to, inflammatory-related pain, neuropathic pain, hyperalgesia, chronic pain, pathological pain, allodynia, cancer-associated pain, atypical pain, neuroinflammation-associated pain conditions, neurogenic inflammation-associated pain, paroxysmal extreme pain disorder, inherited erythromelalgia, or a combination thereof. The atypical pain may be fibromyalgia or sickle cell disease associated pain.

(1) Neuropathic Pain

The pain may be neuropathic pain. Neuropathic pain may be caused by injury to or pathological changes in the peripheral or central nervous system. The neuropathic pain may be characterized by mechanical allodynia, heat hyperalgesia, increased response to heat and/or mechanical stimulation, spontaneous pain, ongoing pain, or any combination thereof.

The neuropathic pain may include pain associated with disorders and conditions including, but not limited to, diabetic neuropathy, chemotherapy, human immunodeficiency virus (HIV) infection, postherpetic neuralgia (PHN; also known as shingles), surgery (e.g., amputation, thoracotomy, mastectomy, hernia surgery, and so forth), spinal cord injury, stroke, or a combination thereof. The shingles may occur after infection with varicella zoser virus (VZV).

(2) Inflammation-Related Pain

The pain may be inflammation-related pain (also known herein as "inflammatory pain"), for example, after tissue injury (e.g., skin, muscle, bone, and joint injury). Accordingly, the method of treatment may reduce or suppress the inflammation-related pain. The inflammation-related pain may include, but is not limited to, arthritis pain, dental pain, low back pain, pain associated inflammatory bowel disease, temporomandibular joint (TMJ), or a combination thereof.

The inflammation-related pain may be pain associated with, but is not limited to, neurogenic inflammation and neuroinflammation. Diseases associated with neurogenic inflammation may include, but are not limited to, asthma, arthritis, eczema, psoriasis, and migraine or headache. Diseases associated with neuroinflammation may include, but are not limited to, complex regional pain syndrome (CRPS), headache, migraine, or a combination thereof.

5. METHOD OF PROTECTION

As described above, also provided herein is a method of protecting neurons in a subject in need thereof. As such, the method of protection may protect the peripheral nervous system, central nervous system, or a combination thereof in the subject from injury. The method of protection may protect the axons of neurons in the subject from injury. The method of protection may protect dorsal root ganglion neurons in the subject from injury. The method of protect may protect the axons of dorsal root ganglion neurons in the subject from injury. The method of protection may include administering the pharmaceutical composition. The method of protection may include administration of the bone marrow stromal cells. The method of protection may include administration of TGF-β1. The bone marrow stromal cells may be administered to the subject prior to administration of the TGF-β1. The TGF-β1 may be administered to the subject prior to the administration of the bone marrow stromal cells. The bone marrow stromal cells and the TGF-β1 may be administered to the subject concurrently.

The amount of TGF-β1 to be administered may be about 0.1 mg/kg to about 1000 mg/kg, about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg. A skilled practitioner, such as a physician (e.g., a neurologist) can readily determine optimal dosage levels. The TGF-β1 may be administered once per day, twice per day, once per week, or at a timing prescribed by a skilled artisan. The skilled artisan will appreciate that certain factors influence dosage and timing required to effectively treat a patient, including but not limited to the severity of the pain, injury, disease, previous treatments, the general health of the patient, the age of the patient, and other diseases or injuries present.

The method of protection may include administration of the bone marrow stromal cells to the subject. The method of protection may include administration of about $0.5 \times 10^5$ to about $5.0 \times 10^7$, about $0.6 \times 10^5$ to about $5.0 \times 10^7$, about $0.7 \times 10^5$ to about $5.0 \times 10^7$, about $0.8 \times 10^5$ to about $5.0 \times 10^7$, about $0.9 \times 10^5$ to about $5.0 \times 10^7$, about $1.0 \times 10^5$ to about $5.0 \times 10^7$, about $1.5 \times 10^5$ to about $5.0 \times 10^7$, about $2.0 \times 10^5$ to about $5.0 \times 10^7$, about $2.5 \times 10^5$ to about $5.0 \times 10^7$, about $3.0 \times 10^5$ to about $5.0 \times 10^7$, about $3.5 \times 10^5$ to about $5.0 \times 10^7$, about $4.0 \times 10^5$ to about $5.0 \times 10^7$, about $4.5 \times 10^5$ to about $5.0 \times 10^7$, about $5.0 \times 10^5$ to about $5.0 \times 10^7$, about $5.5 \times 10^5$ to about $5.0 \times 10^7$, about $6.0 \times 10^5$ to about $5.0 \times 10^7$, about $6.5 \times 10^5$ to about $5.0 \times 10^7$, about $7.0 \times 10^5$ to about $5.0 \times 10^7$, about $7.5 \times 10^5$ to about $5.0 \times 10^7$, about $8.0 \times 10^5$ to about $5.0 \times 10^7$, about $8.5 \times 10^5$ to about $5.0 \times 10^7$, about $9.0 \times 10^5$ to about $5.0 \times 10^7$, about $9.5 \times 10^5$ to about $5.0 \times 10^7$, about $1.0 \times 10^6$ to about $5.0 \times 10^7$, about $1.5 \times 10^6$ to about $5.0 \times 10^7$, about $2.0 \times 10^6$ to about $5.0 \times 10^7$, about $2.5 \times 10^6$ to about $5.0 \times 10^7$, about $3.0 \times 10^6$ to about $5.0 \times 10^7$, about $3.5 \times 10^6$ to about $5.0 \times 10^7$, about $4.0 \times 10^6$ to about $5.0 \times 10^7$, about $4.5 \times 10^6$ to about $5.0 \times 10^7$, about $5.0 \times 10^6$ to about $5.0 \times 10^7$, about $5.5 \times 10^6$ to about $5.0 \times 10^7$, about $6.0 \times 10^6$ to about $5.0 \times 10^7$, about $6.5 \times 10^6$ to about $5.0 \times 10^7$, about $7.0 \times 10^6$ to about $5.0 \times 10^7$, about $7.5 \times 10^6$ to about $5.0 \times 10^7$, about $8.0 \times 10^6$ to about $5.0 \times 10^7$, about $8.5 \times 10^6$ to about $5.0 \times 10^7$, about $9.0 \times 10^6$ to about $5.0 \times 10^7$, about $9.5 \times 10^6$ to about $5.0 \times 10^7$, about $1.0 \times 10^7$ to about $5.0 \times 10^7$, about $1.5 \times 10^7$ to about $5.0 \times 10^7$, about $2.0 \times 10^7$ to about $5.0 \times 10^7$, about $2.5 \times 10^7$ to about $5.0 \times 10^7$, about $3.0 \times 10^7$ to about $5.0 \times 10^7$, about $3.5 \times 10^7$ to about $5.0 \times 10^7$, about $4.0 \times 10^7$ to about $5.0 \times 10^7$, about $4.5 \times 10^7$ to about $5.0 \times 10^7$, about $0.5 \times 10^5$ to about $4.5 \times 10^7$, about $0.5 \times 10^5$ to about $4.0 \times 10^7$, about $0.5 \times 10^5$ to about $3.5 \times 10^7$, about $0.5 \times 10^5$ to about $3.0 \times 10^7$, about $0.5 \times 10^5$ to about $2.5 \times 10^7$, about $0.5 \times 10^5$ to about $2.0 \times 10^7$, about $0.5 \times 10^5$ to about $1.5 \times 10^7$, about $0.5 \times 10^5$ to about $1.0 \times 10^7$, about $0.5 \times 10^5$ to about $9.5 \times 10^6$, about $0.5 \times 10^5$ to about $9.0 \times 10^6$, about $0.5 \times 10^5$ to about $8.5 \times 10^6$, about $0.5 \times 10^5$ to about $8.0 \times 10^6$, about $0.5 \times 10^5$ to about $7.5 \times 10^6$, about $0.5 \times 10^5$ to about $7.0 \times 10^6$, about $0.5 \times 10^5$ to about $6.5 \times 10^6$, about $0.5 \times 10^5$ to about $6.0 \times 10^6$, about $0.5 \times 10^5$ to about $5.5 \times 10^6$, about $0.5 \times 10^5$ to about $5.0 \times 10^6$, about $0.5 \times 10^5$ to about $4.5 \times 10^6$, about $0.5 \times 10^5$ to about $4.0 \times 10^6$, about $0.5 \times 10^5$ to about $3.5 \times 10^6$, about $0.5 \times 10^5$ to about $3.0 \times 10^6$, about $0.5 \times 10^5$ to about $2.5 \times 10^6$, about $0.5 \times 10^5$ to about $2.0 \times 10^6$, $0.5 \times 10^5$ to about $1.5 \times 10^6$, about $0.5 \times 10^5$ to about $1.0 \times 10^6$, about $0.5 \times 10^5$ to about $9.5 \times 10^5$, about $0.5 \times 10^5$ to about $9.0 \times 10^5$, about $0.5 \times 10^5$ to about $8.5 \times 10^5$, about $0.5 \times 10^5$ to about $8.0 \times 10^5$, about $0.5 \times 10^5$ to about $7.5 \times 10^5$, about $0.5 \times 10^5$ to about $7.0 \times 10^5$, about $0.5 \times 10^5$ to about $6.5 \times 10^5$, about $0.5 \times 10^5$ to about $6.0 \times 10^5$, about $0.5 \times 10^5$ to about $5.5 \times 10^5$, about $0.5 \times 10^5$ to about $5.0 \times 10^5$, about $0.5 \times 10^5$ to about $4.5 \times 10^5$, about $0.5 \times 10^5$ to about $4.0 \times 10^5$, about $0.5 \times 10^5$ to about $3.5 \times 10^5$, about $0.5 \times 10^5$ to about $3.0 \times 10^5$, about $0.5 \times 10^5$ to about $2.5 \times 10^5$, about $0.5 \times 10^5$ to about $2.0 \times 10^5$, about $0.5 \times 10^5$ to about $1.5 \times 10^5$, about $0.5 \times 10^5$ to about $1.0 \times 10^5$, about $0.6 \times 10^5$ to about $4.5 \times 10^7$, about $0.7 \times 10^5$ to about $4.0 \times 10^7$, about $0.8 \times 10^5$ to about $3.5 \times 10^7$, about $0.9 \times 10^5$ to about $3.0 \times 10^7$, about $1.0 \times 10^5$ to about $2.5 \times 10^7$, about $1.5 \times 10^5$ to about $2.0 \times 10^7$, about $2.0 \times 10^5$ to about $1.5 \times 10^7$, about $2.5 \times 10^5$ to about $1.0 \times 10^7$, about $3.0 \times 10^5$ to about $9.5 \times 10^6$, about $3.5 \times 10^5$ to about $9.0 \times 10^6$, about $4.0 \times 10^5$ to about $8.5 \times 10^6$, about $4.5 \times 10^5$ to about $8.0 \times 10^6$, about $5.0 \times 10^5$ to about $7.5 \times 10^6$, about $5.5 \times 10^5$ to about $7.0 \times 10^6$, about $6.0 \times 10^5$ to about $6.5 \times 10^6$, about $6.5 \times 10^5$ to about $6.0 \times 10^6$, about $7.0 \times 10^5$ to about $5.5 \times 10^6$, about $7.5 \times 10^5$ to about $5.0 \times 10^6$, about $8.0 \times 10^5$ to about $4.5 \times 10^6$, about $8.5 \times 10^5$ to about $4.0 \times 10^6$, about $9.0 \times 10^5$ to about $3.5 \times 10^6$, about $9.5 \times 10^5$ to about $3.0 \times 10^6$, about $1.0 \times 10^6$ to about $2.5 \times 10^6$, about $1.5 \times 10^6$ to about $2.0 \times 10^6$, or about $0.5 \times 10^5$, about $0.6 \times 10^5$, about $0.7 \times 10^5$, about $0.8 \times 10^5$, about $0.9 \times 10^5$, about $1.0 \times 10^5$, about $1.1 \times 10^5$, about $1.2 \times 10^5$, about $1.3 \times 10^5$, about $1.4 \times 10^5$, about $1.5 \times 10^5$, about $1.6 \times 10^5$, about $1.7 \times 10^5$, about $1.8 \times 10^5$, about $1.9 \times 10^5$, about $2.0 \times 10^5$, about $2.1 \times 10^5$, about $2.2 \times 10^5$, about $2.3 \times 10^5$, about $2.4 \times 10^5$, about $2.5 \times 10^5$, about $2.6 \times 10^5$, about $2.7 \times 10^5$, about $2.8 \times 10^5$, about $2.9 \times 10^5$, about $3.0 \times 10^5$, about $3.1 \times 10^5$, about $3.2 \times 10^5$, about $3.3 \times 10^5$, about $3.4 \times 10^5$, about $3.5 \times 10^5$, about $3.6 \times 10^5$, about $3.7 \times 10^5$, about $3.8 \times 10^5$, about $3.9 \times 10^5$, about $4.0 \times 10^5$, about $4.1 \times 10^5$, about $4.2 \times 10^5$, about $4.3 \times 10^5$, about $4.4 \times 10^5$, about $4.5 \times 10^5$, about $4.6 \times 10^5$, about $4.7 \times 10^5$, about $4.8 \times 10^5$, about $4.9 \times 10^5$, about $5.0 \times 10^5$, about $5.1 \times 10^5$, about $5.2 \times 10^5$, about $5.3 \times 10^5$, about $5.4 \times 10^5$, about $5.5 \times 10^5$, about $5.6 \times 10^5$, about $5.7 \times 10^5$, about $5.8 \times 10^5$, about $5.9 \times 10^5$, about $6.0 \times 10^5$, about $6.1 \times 10^5$, about $6.2 \times 10^5$, about $6.3 \times 10^5$, about $6.4 \times 10^5$, about $6.5 \times 10^5$, about $6.6 \times 10^5$, about $6.7 \times 10^5$, about $6.8 \times 10^5$, about $6.9 \times 10^5$, about $7.0 \times 10^5$, about $7.1 \times 10^5$, about $7.2 \times 10^5$, about $7.3 \times 10^5$, about $7.4 \times 10^5$, about $7.5 \times 10^5$, about $7.6 \times 10^5$, about $7.7 \times 10^5$, about $7.8 \times 10^5$, about $7.9 \times 10^5$, about $8.0 \times 10^5$, about $8.1 \times 10^5$, about $8.2 \times 10^5$, about $8.3 \times 10^5$, about $8.4 \times 10^5$, about $8.5 \times 10^5$, about $8.6 \times 10^5$, about $8.7 \times 10^5$, about $8.8 \times 10^5$, about $8.9 \times 10^5$, about $9.0 \times 10^5$, about $9.1 \times 10^5$, about $9.2 \times 10^5$, about $9.3 \times 10^5$, about $9.4 \times 10^5$, about $9.5 \times 10^5$, about $9.6 \times 10^5$, about $9.7 \times 10^5$, about $9.8 \times 10^5$, about $9.9 \times 10^5$, about $1.0 \times 10^6$, about $1.1 \times 10^6$, about $1.2 \times 10^6$, about $1.3 \times 10^6$, about $1.4 \times 10^6$, about $1.5 \times 10^6$, about $1.6 \times 10^6$, about $1.7 \times 10^6$, about $1.8 \times 10^6$, about $1.9 \times 10^6$, about $2.0 \times 10^6$, about $2.1 \times 10^6$, about $2.2 \times 10^6$, about $2.3 \times 10^6$, about $2.4 \times 10^6$, about $2.5 \times 10^6$, about $2.6 \times 10^6$, about $2.7 \times 10^6$, about $2.8 \times 10^6$, about $2.9 \times 10^6$, about $3.0 \times 10^6$, about $3.1 \times 10^6$, about $3.2 \times 10^6$, about $3.3 \times 10^6$, about $3.4 \times 10^6$, about $3.5 \times 10^6$, about $3.6 \times 10^6$, about $3.7 \times 10^6$, about $3.8 \times 10^6$, about $3.9 \times 10^6$, about $4.0 \times 10^6$, about $4.1 \times 10^6$, about $4.2 \times 10^6$, about $4.3 \times 10^6$, about $4.4 \times 10^6$, about $4.5 \times 10^6$, about $4.6 \times 10^6$, about $4.7 \times 10^6$, about $4.8 \times 10^6$, about $4.9 \times 10^6$, about $5.0 \times 10^6$, about $5.1 \times 10^6$, about $5.2 \times 10^6$, about $5.3 \times 10^6$, about $5.4 \times 10^6$, about $5.5 \times 10^6$, about $5.6 \times 10^6$, about $5.7 \times 10^6$, about $5.8 \times 10^6$, about $5.9 \times 10^6$, about $6.0 \times 10^6$, about $6.1 \times 10^6$, about $6.2 \times 10^6$, about $6.3 \times 10^6$, about $6.4 \times 10^6$, about $6.5 \times 10^6$, about $6.6 \times 10^6$, about $6.7 \times 10^6$, about $6.8 \times 10^6$, about $6.9 \times 10^6$, about $7.0 \times 10^6$, about $7.1 \times 10^6$, about $7.2 \times 10^6$, about $7.3 \times 10^6$, about $7.4 \times 10^6$, about $7.5 \times 10^6$, about $7.6 \times 10^6$, about $7.7 \times 10^6$, about $7.8 \times 10^6$, about $7.9 \times 10^6$, about $8.0 \times 10^6$, about $8.1 \times 10^6$, about $8.2 \times 10^6$, about $8.3 \times 10^6$, about $8.4 \times 10^6$, about $8.5 \times 10^6$, about $8.6 \times 10^6$, about $8.7 \times 10^6$, about $8.8 \times 10^6$, about $8.9 \times 10^6$, about $9.0 \times 10^6$, about $9.1 \times 10^6$, about $9.2 \times 10^6$, about $9.3 \times 10^6$, about $9.4 \times 10^6$, about $9.5 \times 10^6$, about $9.6 \times 10^6$, about $9.7 \times 10^6$, about $9.8 \times 10^6$, about $9.9 \times 10^6$, about $1.0 \times 10^7$, about $1.1 \times 10^7$, about $1.2 \times 10^7$, about $1.3 \times 10^7$, about $1.4 \times 10^7$, about $1.5 \times 10^7$, about $1.6 \times 10^7$, about $1.7 \times 10^7$, about $1.8 \times 10^7$, about $1.9 \times 10^7$, about $2.0 \times 10^7$, about $2.1 \times 10^7$, about $2.2 \times 10^7$, about $2.3 \times 10^7$, about $2.4 \times 10^7$, about $2.5 \times 10^7$, about $2.6 \times 10^7$, about $2.7 \times 10^7$, about $2.8 \times 10^7$, about $2.9 \times 10^7$, about $3.0 \times 10^7$, about $3.1 \times 10^7$, about $3.2 \times 10^7$, about $3.3 \times 10^7$, about $3.4 \times 10^7$, about $3.5 \times 10^7$, about $3.6 \times 10^7$, about $3.7 \times 10^7$, about $3.8 \times 10^7$, about $3.9 \times 10^7$, about $4.0 \times 10^7$, about $4.1 \times 10^7$, about $4.2 \times 10^7$, about $4.3 \times 10^7$, about $4.4 \times 10^7$, about $4.5 \times 10^7$, about $4.6 \times 10^7$, about $4.7 \times 10^7$, about $4.8 \times 10^7$, about $4.9 \times 10^7$, or about $5.0 \times 10^7$ bone marrow stromal cells to the subject.

The method of protection may include administration of at least about $0.5 \times 10^5$ to about $5.0 \times 10^7$, about $0.6 \times 10^5$ to about $5.0 \times 10^7$, about $0.7 \times 10^5$ to about $5.0 \times 10^7$, about $0.8 \times 10^5$ to about $5.0 \times 10^7$, about $0.9 \times 10^5$ to about $5.0 \times 10^7$, about $1.0 \times 10^5$ to about $5.0 \times 10^7$, about $1.5 \times 10^5$ to about $5.0 \times 10^7$, about $2.0 \times 10^5$ to about $5.0 \times 10^7$, about $2.5 \times 10^5$ to about $5.0 \times 10^7$, about $3.0 \times 10^5$ to about $5.0 \times 10^7$, about $3.5 \times 10^5$ to about $5.0 \times 10^7$, about $4.0 \times 10^5$ to about $5.0 \times 10^7$, about $4.5 \times 10^5$ to about $5.0 \times 10^7$, about $5.0 \times 10^5$ to about $5.0 \times 10^7$, about $5.5 \times 10^5$ to about $5.0 \times 10^7$, about $6.0 \times 10^5$ to about $5.0 \times 10^7$, about $6.5 \times 10^5$ to about $5.0 \times 10^7$, about $7.0 \times 10^5$ to about $5.0 \times 10^7$, about $7.5 \times 10^5$ to about $5.0 \times 10^7$, about $8.0 \times 10^5$ to about $5.0 \times 10^7$, about $8.5 \times 10^5$ to about $5.0 \times 10^7$, about $9.0 \times 10^5$ to about $5.0 \times 10^7$, about $9.5 \times 10^5$ to about $5.0 \times 10^7$, about $1.0 \times 10^6$ to about $5.0 \times 10^7$, about $1.5 \times 10^6$ to about $5.0 \times 10^7$, about $2.0 \times 10^6$ to about $5.0 \times 10^7$, about $2.5 \times 10^6$ to about $5.0 \times 10^7$, about $3.0 \times 10^6$ to about $5.0 \times 10^7$, about $3.5 \times 10^6$ to about $5.0 \times 10^7$, about $4.0 \times 10^6$ to about $5.0 \times 10^7$, about $4.5 \times 10^6$ to about $5.0 \times 10^7$, about $5.0 \times 10^6$ to about $5.0 \times 10^7$, about $5.5 \times 10^6$ to about $5.0 \times 10^7$, about $6.0 \times 10^6$ to about $5.0 \times 10^7$, about $6.5 \times 10^6$ to about $5.0 \times 10^7$, about $7.0 \times 10^6$ to about $5.0 \times 10^7$, about $7.5 \times 10^6$ to about $5.0 \times 10^7$, about $8.0 \times 10^6$ to about $5.0 \times 10^7$, about $8.5 \times 10^6$ to about $5.0 \times 10^7$, about $9.0 \times 10^6$ to about $5.0 \times 10^7$, about $9.5 \times 10^6$ to about $5.0 \times 10^7$, about $1.0 \times 10^7$ to about $5.0 \times 10^7$, about $1.5 \times 10^7$ to about $5.0 \times 10^7$, about $2.0 \times 10^7$ to about $5.0 \times 10^7$, about $2.5 \times 10^7$ to about $5.0 \times 10^7$, about $3.0 \times 10^7$ to about $5.0 \times 10^7$, about $3.5 \times 10^7$ to about $5.0 \times 10^7$, about $4.0 \times 10^7$ to about $5.0 \times 10^7$, about $4.5 \times 10^7$ to about $5.0 \times 10^7$, about $0.5 \times 10^5$ to about $4.5 \times 10^7$, about $0.5 \times 10^5$ to about $4.0 \times 10^7$, about $0.5 \times 10^5$ to about $3.5 \times 10^7$, about $0.5 \times 10^5$ to about $3.0 \times 10^7$, about $0.5 \times 10^5$ to about $2.5 \times 10^7$, about $0.5 \times 10^5$ to about $2.0 \times 10^7$, about $0.5 \times 10^5$ to about $1.5 \times 10^7$, about $0.5 \times 10^5$ to about $1.0 \times 10^7$, about $0.5 \times 10^5$ to about $9.5 \times 10^6$, about $0.5 \times 10^5$ to about $9.0 \times 10^6$, about $0.5 \times 10^5$ to about $8.5 \times 10^6$, about $0.5 \times 10^5$ to about $8.0 \times 10^6$, about $0.5 \times 10^5$ to about $7.5 \times 10^6$, about $0.5 \times 10^5$ to about $7.0 \times 10^6$, about $0.5 \times 10^5$ to about $6.5 \times 10^6$, about $0.5 \times 10^5$ to about $6.0 \times 10^6$, about $0.5 \times 10^5$ to about $5.5 \times 10^6$, about $0.5 \times 10^5$ to about $5.0 \times 10^6$, about $0.5 \times 10^5$ to about $4.5 \times 10^6$, about $0.5 \times 10^5$ to about $4.0 \times 10^6$, about $0.5 \times 10^5$ to about $3.5 \times 10^6$, about $0.5 \times 10^5$ to about $3.0 \times 10^6$, about $0.5 \times 10^5$ to about $2.5 \times 10^6$, about $0.5 \times 10^5$ to about $2.0 \times 10^6$, $0.5 \times 10^5$ to about $1.5 \times 10^6$, about $0.5 \times 10^5$ to about $1.0 \times 10^6$, about $0.5 \times 10^5$ to about $9.5 \times 10^5$, about $0.5 \times 10^5$ to about $9.0 \times 10^5$, about $0.5 \times 10^5$ to about $8.5 \times 10^5$, about $0.5 \times 10^5$ to about $8.0 \times 10^5$, about $0.5 \times 10^5$ to about $7.5 \times 10^5$, about $0.5 \times 10^5$ to about $7.0 \times 10^5$, about $0.5 \times 10^5$ to about $6.5 \times 10^5$, about $0.5 \times 10^5$ to about $6.0 \times 10^5$, about $0.5 \times 10^5$ to about $5.5 \times 10^5$, about $0.5 \times 10^5$ to about $5.0 \times 10^5$, about $0.5 \times 10^5$ to about $4.5 \times 10^5$, about $0.5 \times 10^5$ to about $4.0 \times 10^5$, about $0.5 \times 10^5$ to about $3.5 \times 10^5$, about $0.5 \times 10^5$ to about $3.0 \times 10^5$, about $0.5 \times 10^5$ to about $2.5 \times 10^5$, about $0.5 \times 10^5$ to about $2.0 \times 10^5$, about $0.5 \times 10^5$ to about $1.5 \times 10^5$, about $0.5 \times 10^5$ to about $1.0 \times 10^5$, about $0.6 \times 10^5$ to about $4.5 \times 10^7$, about $0.7 \times 10^5$ to about $4.0 \times 10^7$, about $0.8 \times 10^5$ to about $3.5 \times 10^7$, about $0.9 \times 10^5$ to about $3.0 \times 10^7$, about $1.0 \times 10^5$ to about $2.5 \times 10^7$, about $1.5 \times 10^5$ to about $2.0 \times 10^7$, about $2.0 \times 10^5$ to about $1.5 \times 10^7$, about $2.5 \times 10^5$ to about $1.0 \times 10^7$, about $3.0 \times 10^5$ to about $9.5 \times 10^6$, about $3.5 \times 10^5$ to about $9.0 \times 10^6$, about $4.0 \times 10^5$ to about $8.5 \times 10^6$, about $4.5 \times 10^5$ to about $8.0 \times 10^6$, about $5.0 \times 10^5$ to about $7.5 \times 10^6$, about $5.5 \times 10^5$ to about $7.0 \times 10^6$, about $6.0 \times 10^5$ to about $6.5 \times 10^6$, about $6.5 \times 10^5$ to about $6.0 \times 10^6$, about $7.0 \times 10^5$ to about $5.5 \times 10^6$, about $7.5 \times 10^5$ to about $5.0 \times 10^6$, about $8.0 \times 10^5$ to about $4.5 \times 10^6$, about $8.5 \times 10^5$ to about $4.0 \times 10^6$, about $9.0 \times 10^5$ to about $3.5 \times 10^6$, about $9.5 \times 10^5$ to about $3.0 \times 10^6$, about $1.0 \times 10^6$ to about $2.5 \times 10^6$, about $1.5 \times 10^6$ to about $2.0 \times 10^6$, or about $0.5 \times 10^5$, about $0.6 \times 10^5$, about $0.7 \times 10^5$, about $0.8 \times 10^5$, about $0.9 \times 10^5$, about $1.0 \times 10^5$, about $1.1 \times 10^5$, about $1.2 \times 10^5$, about $1.3 \times 10^5$, about $1.4 \times 10^5$, about $1.5 \times 10^5$, about $1.6 \times 10^5$, about $1.7 \times 10^5$, about $1.8 \times 10^5$, about $1.9 \times 10^5$, about $2.0 \times 10^5$, about $2.1 \times 10^5$, about $2.2 \times 10^5$, about $2.3 \times 10^5$, about $2.4 \times 10^5$, about $2.5 \times 10^5$, about $2.6 \times 10^5$, about $2.7 \times 10^5$, about $2.8 \times 10^5$, about $2.9 \times 10^5$, about $3.0 \times 10^5$, about $3.1 \times 10^5$, about $3.2 \times 10^5$, about $3.3 \times 10^5$, about $3.4 \times 10^5$, about $3.5 \times 10^5$, about $3.6 \times 10^5$, about $3.7 \times 10^5$, about $3.8 \times 10^5$, about $3.9 \times 10^5$, about $4.0 \times 10^5$, about $4.1 \times 10^5$, about $4.2 \times 10^5$, about $4.3 \times 10^5$, about $4.4 \times 10^5$, about $4.5 \times 10^5$, about $4.6 \times 10^5$, about $4.7 \times 10^5$, about $4.8 \times 10^5$, about $4.9 \times 10^5$, about $5.0 \times 10^5$, about $5.1 \times 10^5$, about $5.2 \times 10^5$, about $5.3 \times 10^5$, about $5.4 \times 10^5$, about $5.5 \times 10^5$, about $5.6 \times 10^5$, about $5.7 \times 10^5$, about $5.8 \times 10^5$, about $5.9 \times 10^5$, about $6.0 \times 10^5$, about $6.1 \times 10^5$, about $6.2 \times 10^5$, about $6.3 \times 10^5$, about $6.4 \times 10^5$, about $6.5 \times 10^5$, about $6.6 \times 10^5$, about $6.7 \times 10^5$, about $6.8 \times 10^5$, about $6.9 \times 10^5$, about $7.0 \times 10^5$, about $7.1 \times 10^5$, about $7.2 \times 10^5$, about $7.3 \times 10^5$, about $7.4 \times 10^5$, about $7.5 \times 10^5$, about $7.6 \times 10^5$, about $7.7 \times 10^5$, about $7.8 \times 10^5$, about $7.9 \times 10^5$, about $8.0 \times 10^5$, about $8.1 \times 10^5$, about $8.2 \times 10^5$, about $8.3 \times 10^5$, about $8.4 \times 10^5$, about $8.5 \times 10^5$, about $8.6 \times 10^5$, about $8.7 \times 10^5$, about $8.8 \times 10^5$, about $8.9 \times 10^5$, about $9.0 \times 10^5$, about $9.1 \times 10^5$, about $9.2 \times 10^5$, about $9.3 \times 10^5$, about $9.4 \times 10^5$, about $9.5 \times 10^5$, about $9.6 \times 10^5$, about $9.7 \times 10^5$, about $9.8 \times 10^5$, about $9.9 \times 10^5$, about $1.0 \times 10^6$, about $1.1 \times 10^6$, about $1.2 \times 10^6$, about $1.3 \times 10^6$, about $1.4 \times 10^6$, about $1.5 \times 10^6$, about $1.6 \times 10^6$, about $1.7 \times 10^6$, about $1.8 \times 10^6$, about $1.9 \times 10^6$, about $2.0 \times 10^6$, about $2.1 \times 10^6$, about $2.2 \times 10^6$, about $2.3 \times 10^6$, about $2.4 \times 10^6$, about $2.5 \times 10^6$, about $2.6 \times 10^6$, about $2.7 \times 10^6$, about $2.8 \times 10^6$, about $2.9 \times 10^6$, about $3.0 \times 10^6$, about $3.1 \times 10^6$, about $3.2 \times 10^6$, about $3.3 \times 10^6$, about $3.4 \times 10^6$, about $3.5 \times 10^6$, about $3.6 \times 10^6$, about $3.7 \times 10^6$, about $3.8 \times 10^6$, about $3.9 \times 10^6$, about $4.0 \times 10^6$, about $4.1 \times 10^6$, about $4.2 \times 10^6$, about $4.3 \times 10^6$, about $4.4 \times 10^6$, about $4.5 \times 10^6$, about $4.6 \times 10^6$, about $4.7 \times 10^6$, about $4.8 \times 10^6$, about $4.9 \times 10^6$, about $5.0 \times 10^6$, about $5.1 \times 10^6$, about $5.2 \times 10^6$, about $5.3 \times 10^6$, about $5.4 \times 10^6$, about $5.5 \times 10^6$, about $5.6 \times 10^6$, about $5.7 \times 10^6$, about $5.8 \times 10^6$, about $5.9 \times 10^6$, about $6.0 \times 10^6$, about $6.1 \times 10^6$, about $6.2 \times 10^6$, about $6.3 \times 10^6$, about $6.4 \times 10^6$, about $6.5 \times 10^6$, about $6.6 \times 10^6$, about $6.7 \times 10^6$, about $6.8 \times 10^6$, about $6.9 \times 10^6$, about $7.0 \times 10^6$, about $7.1 \times 10^6$, about $7.2 \times 10^6$, about $7.3 \times 10^6$, about $7.4 \times 10^6$, about $7.5 \times 10^6$, about $7.6 \times 10^6$, about $7.7 \times 10^6$, about $7.8 \times 10^6$, about $7.9 \times 10^6$, about $8.0 \times 10^6$, about $8.1 \times 10^6$, about $8.2 \times 10^6$, about $8.3 \times 10^6$, about $8.4 \times 10^6$, about $8.5 \times 10^6$, about $8.6 \times 10^6$, about $8.7 \times 10^6$, about $8.8 \times 10^6$, about $8.9 \times 10^6$, about $9.0 \times 10^6$, about $9.1 \times 10^6$, about $9.2 \times 10^6$, about $9.3 \times 10^6$, about $9.4 \times 10^6$, about $9.5 \times 10^6$, about $9.6 \times 10^6$, about $9.7 \times 10^6$, about $9.8 \times 10^6$, about $9.9 \times 10^6$, about $1.0 \times 10^7$, about $1.1 \times 10^7$, about $1.2 \times 10^7$, about $1.3 \times 10^7$, about $1.4 \times 10^7$, about $1.5 \times 10^7$, about $1.6 \times 10^7$, about $1.7 \times 10^7$, about $1.8 \times 10^7$, about $1.9 \times 10^7$, about $2.0 \times 10^7$, about $2.1 \times 10^7$, about $2.2 \times 10^7$, about $2.3 \times 10^7$, about $2.4 \times 10^7$, about $2.5 \times 10^7$, about $2.6 \times 10^7$, about $2.7 \times 10^7$, about $2.8 \times 10^7$, about $2.9 \times 10^7$, about $3.0 \times 10^7$, about $3.1 \times 10^7$, about $3.2 \times 10^7$, about $3.3 \times 10^7$, about $3.4 \times 10^7$, about $3.5 \times 10^7$, about $3.6 \times 10^7$, about $3.7 \times 10^7$, about $3.8 \times 10^7$, about $3.9 \times 10^7$, about $4.0 \times 10^7$, about $4.1 \times 10^7$, about $4.2 \times 10^7$, about $4.3 \times 10^7$, about $4.4 \times 10^7$, about $4.5 \times 10^7$, about $4.6 \times 10^7$, about $4.7 \times 10^7$, about $4.8 \times 10^7$, about $4.9 \times 10^7$, or about $5.0 \times 10^7$ bone marrow stromal cells to the subject.

The method of protection may include administration of less than about $0.5 \times 10^5$ to about $5.0 \times 10^7$, about $0.6 \times 10^5$ to about $5.0 \times 10^7$, about $0.7 \times 10^5$ to about $5.0 \times 10^7$, about $0.8 \times 10^5$ to about $5.0 \times 10^7$, about $0.9 \times 10^5$ to about $5.0 \times 10^7$, about $1.0 \times 10^5$ to about $5.0 \times 10^7$, about $1.5 \times 10^5$ to about $5.0 \times 10^7$, about $2.0 \times 10^5$ to about $5.0 \times 10^7$, about $2.5 \times 10^5$ to about $5.0 \times 10^7$, about $3.0 \times 10^5$ to about $5.0 \times 10^7$, about $3.5 \times 10^5$ to about $5.0 \times 10^7$, about $4.0 \times 10^5$ to about $5.0 \times 10^7$, about $4.5 \times 10^5$ to about $5.0 \times 10^7$, about $5.0 \times 10^5$ to about $5.0 \times 10^7$, about $5.5 \times 10^5$ to about $5.0 \times 10^7$, about $6.0 \times 10^5$ to about $5.0 \times 10^7$, about $6.5 \times 10^5$ to about $5.0 \times 10^7$, about $7.0 \times 10^5$ to about $5.0 \times 10^7$, about $7.5 \times 10^5$ to about $5.0 \times 10^7$, about $8.0 \times 10^5$ to about $5.0 \times 10^7$, about $8.5 \times 10^5$ to about $5.0 \times 10^7$, about $9.0 \times 10^5$ to about $5.0 \times 10^7$, about $9.5 \times 10^5$ to about $5.0 \times 10^7$, about $1.0 \times 10^6$ to about $5.0 \times 10^7$, about $1.5 \times 10^6$ to about $5.0 \times 10^7$, about $2.0 \times 10^6$ to about $5.0 \times 10^7$, about $2.5 \times 10^6$ to about $5.0 \times 10^7$, about $3.0 \times 10^6$ to about $5.0 \times 10^7$, about $3.5 \times 10^6$ to about $5.0 \times 10^7$, about $4.0 \times 10^6$ to about $5.0 \times 10^7$, about $4.5 \times 10^6$ to about $5.0 \times 10^7$, about $5.0 \times 10^6$ to about $5.0 \times 10^7$, about $5.5 \times 10^6$ to about $5.0 \times 10^7$, about $6.0 \times 10^6$ to about $5.0 \times 10^7$, about $6.5 \times 10^6$ to about $5.0 \times 10^7$, about $7.0 \times 10^6$ to about $5.0 \times 10^7$, about $7.5 \times 10^6$ to about $5.0 \times 10^7$, about $8.0 \times 10^6$ to about $5.0 \times 10^7$, about $8.5 \times 10^6$ to about $5.0 \times 10^7$, about $9.0 \times 10^6$ to about $5.0 \times 10^7$, about $9.5 \times 10^6$ to about $5.0 \times 10^7$, about $1.0 \times 10^7$ to about $5.0 \times 10^7$, about $1.5 \times 10^7$ to about $5.0 \times 10^7$, about $2.0 \times 10^7$ to about $5.0 \times 10^7$, about $2.5 \times 10^7$ to about $5.0 \times 10^7$, about $3.0 \times 10^7$ to about $5.0 \times 10^7$, about $3.5 \times 10^7$ to about $5.0 \times 10^7$, about $4.0 \times 10^7$ to about $5.0 \times 10^7$, about $4.5 \times 10^7$ to about $5.0 \times 10^7$, about $0.5 \times 10^5$ to about $4.5 \times 10^7$, about $0.5 \times 10^5$ to about $4.0 \times 10^7$, about $0.5 \times 10^5$ to about $3.5 \times 10^7$, about $0.5 \times 10^5$ to about $3.0 \times 10^7$, about $0.5 \times 10^5$ to about $2.5 \times 10^7$, about $0.5 \times 10^5$ to about $2.0 \times 10^7$, about $0.5 \times 10^5$ to about $1.5 \times 10^7$, about $0.5 \times 10^5$ to about $1.0 \times 10^7$, about $0.5 \times 10^5$ to about $9.5 \times 10^6$, about $0.5 \times 10^5$ to about $9.0 \times 10^6$, about $0.5 \times 10^5$ to about $8.5 \times 10^6$, about $0.5 \times 10^5$ to about $8.0 \times 10^6$, about $0.5 \times 10^5$ to about $7.5 \times 10^6$, about $0.5 \times 10^5$ to about $7.0 \times 10^6$, about $0.5 \times 10^5$ to about $6.5 \times 10^6$, about $0.5 \times 10^5$ to about $6.0 \times 10^6$, about $0.5 \times 10^5$ to about $5.5 \times 10^6$, about $0.5 \times 10^5$ to about $5.0 \times 10^6$, about $0.5 \times 10^5$ to about $4.5 \times 10^6$, about $0.5 \times 10^5$ to about $4.0 \times 10^6$, about $0.5 \times 10^5$ to about $3.5 \times 10^6$, about $0.5 \times 10^5$ to about $3.0 \times 10^6$, about $0.5 \times 10^5$ to about $2.5 \times 10^6$, about $0.5 \times 10^5$ to about $2.0 \times 10^6$, $0.5 \times 10^5$ to about $1.5 \times 10^6$, about $0.5 \times 10^5$ to about $1.0 \times 10^6$, about $0.5 \times 10^5$ to about $9.5 \times 10^5$, about $0.5 \times 10^5$ to about $9.0 \times 10^5$, about $0.5 \times 10^5$ to about $8.5 \times 10^5$, about $0.5 \times 10^5$ to about $8.0 \times 10^5$, about $0.5 \times 10^5$ to about $7.5 \times 10^5$, about $0.5 \times 10^5$ to about $7.0 \times 10^5$, about $0.5 \times 10^5$ to about $6.5 \times 10^5$, about $0.5 \times 10^5$ to about $6.0 \times 10^5$, about $0.5 \times 10^5$ to about $5.5 \times 10^5$, about $0.5 \times 10^5$ to about $5.0 \times 10^5$, about $0.5 \times 10^5$ to about $4.5 \times 10^5$, about $0.5 \times 10^5$ to about $4.0 \times 10^5$, about $0.5 \times 10^5$ to about $3.5 \times 10^5$, about $0.5 \times 10^5$ to about $3.0 \times 10^5$, about $0.5 \times 10^5$ to about $2.5 \times 10^5$, about $0.5 \times 10^5$ to about $2.0 \times 10^5$, about $0.5 \times 10^5$ to about $1.5 \times 10^5$, about $0.5 \times 10^5$ to about $1.0 \times 10^5$, about $0.6 \times 10^5$ to about $4.5 \times 10^7$, about $0.7 \times 10^5$ to about $4.0 \times 10^7$, about $0.8 \times 10^5$ to about $3.5 \times 10^7$, about $0.9 \times 10^5$ to about $3.0 \times 10^7$, about $1.0 \times 10^5$ to about $2.5 \times 10^7$, about $1.5 \times 10^5$ to about $2.0 \times 10^7$, about $2.0 \times 10^5$ to about $1.5 \times 10^7$, about $2.5 \times 10^5$ to about $1.0 \times 10^7$, about $3.0 \times 10^5$ to about $9.5 \times 10^6$, about $3.5 \times 10^5$ to about $9.0 \times 10^6$, about $4.0 \times 10^5$ to about $8.5 \times 10^6$, about $4.5 \times 10^5$ to about $8.0 \times 10^6$, about $5.0 \times 10^5$ to about $7.5 \times 10^6$, about $5.5 \times 10^5$ to about $7.0 \times 10^6$, about $6.0 \times 10^5$ to about $6.5 \times 10^6$, about $6.5 \times 10^5$ to about $6.0 \times 10^6$, about $7.0 \times 10^5$ to about $5.5 \times 10^6$, about $7.5 \times 10^5$ to about $5.0 \times 10^6$, about $8.0 \times 10^5$ to about $4.5\times10^6$, about $8.5\times10^5$ to about $4.0\times10^6$, about $9.0\times10^5$ to about $3.5\times10^6$, about $9.5\times10^5$ to about $3.0\times10^6$, about $1.0\times10^6$ to about $2.5\times10^6$, about $1.5\times10^6$ to about $2.0\times10^6$, or about $0.5\times10^5$, about $0.6\times10^5$, about $0.7\times10^5$, about $0.8\times10^5$, about $0.9\times10^5$, about $1.0\times10^5$, about $1.1\times10^5$, about $1.2\times10^5$, about $1.3\times10^5$, about $1.4\times10^5$, about $1.5\times10^5$, about $1.6\times10^5$, about $1.7\times10^5$, about $1.8\times10^5$, about $1.9\times10^5$, about $2.0\times10^5$, about $2.1\times10^5$, about $2.2\times10^5$, about $2.3\times10^5$, about $2.4\times10^5$, about $2.5\times10^5$, about $2.6\times10^5$, about $2.7\times10^5$, about $2.8\times10^5$, about $2.9\times10^5$, about $3.0\times10^5$, about $3.1\times10^5$, about $3.2\times10^5$, about $3.3\times10^5$, about $3.4\times10^5$, about $3.5\times10^5$, about $3.6\times10^5$, about $3.7\times10^5$, about $3.8\times10^5$, about $3.9\times10^5$, about $4.0\times10^5$, about $4.1\times10^5$, about $4.2\times10^5$, about $4.3\times10^5$, about $4.4\times10^5$, about $4.5\times10^5$, about $4.6\times10^5$, about $4.7\times10^5$, about $4.8\times10^5$, about $4.9\times10^5$, about $5.0\times10^5$, about $5.1\times10^5$, about $5.2\times10^5$, about $5.3\times10^5$, about $5.4\times10^5$, about $5.5\times10^5$, about $5.6\times10^5$, about $5.7\times10^5$, about $5.8\times10^5$, about $5.9\times10^5$, about $6.0\times10^5$, about $6.1\times10^5$, about $6.2\times10^5$, about $6.3\times10^5$, about $6.4\times10^5$, about $6.5\times10^5$, about $6.6\times10^5$, about $6.7\times10^5$, about $6.8\times10^5$, about $6.9\times10^5$, about $7.0\times10^5$, about $7.1\times10^5$, about $7.2\times10^5$, about $7.3\times10^5$, about $7.4\times10^5$, about $7.5\times10^5$, about $7.6\times10^5$, about $7.7\times10^5$, about $7.8\times10^5$, about $7.9\times10^5$, about $8.0\times10^5$, about $8.1\times10^5$, about $8.2\times10^5$, about $8.3\times10^5$, about $8.4\times10^5$, about $8.5\times10^5$, about $8.6\times10^5$, about $8.7\times10^5$, about $8.8\times10^5$, about $8.9\times10^5$, about $9.0\times10^5$, about $9.1\times10^5$, about $9.2\times10^5$, about $9.3\times10^5$, about $9.4\times10^5$, about $9.5\times10^5$, about $9.6\times10^5$, about $9.7\times10^5$, about $9.8\times10^5$, about $9.9\times10^5$, about $1.0\times10^6$, about $1.1\times10^6$, about $1.2\times10^6$, about $1.3\times10^6$, about $1.4\times10^6$, about $1.5\times10^6$, about $1.6\times10^6$, about $1.7\times10^6$, about $1.8\times10^6$, about $1.9\times10^6$, about $2.0\times10^6$, about $2.1\times10^6$, about $2.2\times10^6$, about $2.3\times10^6$, about $2.4\times10^6$, about $2.5\times10^6$, about $2.6\times10^6$, about $2.7\times10^6$, about $2.8\times10^6$, about $2.9\times10^6$, about $3.0\times10^6$, about $3.1\times10^6$, about $3.2\times10^6$, about $3.3\times10^6$, about $3.4\times10^6$, about $3.5\times10^6$, about $3.6\times10^6$, about $3.7\times10^6$, about $3.8\times10^6$, about $3.9\times10^6$, about $4.0\times10^6$, about $4.1\times10^6$, about $4.2\times10^6$, about $4.3\times10^6$, about $4.4\times10^6$, about $4.5\times10^6$, about $4.6\times10^6$, about $4.7\times10^6$, about $4.8\times10^6$, about $4.9\times10^6$, about $5.0\times10^6$, about $5.1\times10^6$, about $5.2\times10^6$, about $5.3\times10^6$, about $5.4\times10^6$, about $5.5\times10^6$, about $5.6\times10^6$, about $5.7\times10^6$, about $5.8\times10^6$, about $5.9\times10^6$, about $6.0\times10^6$, about $6.1\times10^6$, about $6.2\times10^6$, about $6.3\times10^6$, about $6.4\times10^6$, about $6.5\times10^6$, about $6.6\times10^6$, about $6.7\times10^6$, about $6.8\times10^6$, about $6.9\times10^6$, about $7.0\times10^6$, about $7.1\times10^6$, about $7.2\times10^6$, about $7.3\times10^6$, about $7.4\times10^6$, about $7.5\times10^6$, about $7.6\times10^6$, about $7.7\times10^6$, about $7.8\times10^6$, about $7.9\times10^6$, about $8.0\times10^6$, about $8.1\times10^6$, about $8.2\times10^6$, about $8.3\times10^6$, about $8.4\times10^6$, about $8.5\times10^6$, about $8.6\times10^6$, about $8.7\times10^6$, about $8.8\times10^6$, about $8.9\times10^6$, about $9.0\times10^6$, about $9.1\times10^6$, about $9.2\times10^6$, about $9.3\times10^6$, about $9.4\times10^6$, about $9.5\times10^6$, about $9.6\times10^6$, about $9.7\times10^6$, about $9.8\times10^6$, about $9.9\times10^6$, about $1.0\times10^7$, about $1.1\times10^7$, about $1.2\times10^7$, about $1.3\times10^7$, about $1.4\times10^7$, about $1.5\times10^7$, about $1.6\times10^7$, about $1.7\times10^7$, about $1.8\times10^7$, about $1.9\times10^7$, about $2.0\times10^7$, about $2.1\times10^7$, about $2.2\times10^7$, about $2.3\times10^7$, about $2.4\times10^7$, about $2.5\times10^7$, about $2.6\times10^7$, about $2.7\times10^7$, about $2.8\times10^7$, about $2.9\times10^7$, about $3.0\times10^7$, about $3.1\times10^7$, about $3.2\times10^7$, about $3.3\times10^7$, about $3.4\times10^7$, about $3.5\times10^7$, about $3.6\times10^7$, about $3.7\times10^7$, about $3.8\times10^7$, about $3.9\times10^7$, about $4.0\times10^7$, about $4.1\times10^7$, about $4.2\times10^7$, about $4.3\times10^7$, about $4.4\times10^7$, about $4.5\times10^7$, about $4.6\times10^7$, about $4.7\times10^7$, about $4.8\times10^7$, about $4.9\times10^7$, or about $5.0\times10^7$ bone marrow stromal cells to the subject.

6. KIT

Also provided herein is a kit for use with the above-described method of treatment or method of protection. The kit may include a container in which the bone marrow stromal cells are contained. The kit may also include a container in which TGF-β1 may be contained. The kit may also include any buffers, diluents, and so forth required for administration of the bone marrow stromal cells. The kit may also include any buffers, diluents, and so forth required for administration of the TGF-β1. The kit may further include instructions for use of the kit in the above-described method of treatment or method of protection. Instructions included in the kit may be affixed to packaging material or may be included as a package insert. The instructions may be written or printed materials, but are not limited to such. Any medium capable of storing such instructions and communicating them to an end user is contemplated by this disclosure. Such media include, but are not limited to, electronic storage media (e.g., magnetic discs, tapes, cartridges, and chips), optical media (e.g., CD ROM), and the like. As used herein, the term "instructions" may include the address of an internet site that provides the instructions.

The present invention has multiple aspects, illustrated by the following non-limiting examples.

7. EXAMPLES

Example 1

Materials and Methods

Animals and Surgery

Adult CD1 mice (male, 25-32 g) were purchased from Charles River Laboratories and used for behavioral studies and primary cultures of BMSCs. Neuropathic pain was produced by chronic constriction injury of the sciatic nerve (CCI) (Bennett, et al. J. Neurosci. 1998, 18, 3059-3072) and spared nerve injury (SNI) (Decosterd, et al. Pain 2000, 87, 149-158). For producing the CCI model animals were anesthetized with isoflurane, the left sciatic nerve was exposed, and three ligatures (7-0 prolene) were placed around the nerve proximal to the trifurcation with one millimeter between each ligature. The ligatures were loosely tied until a short flick of the ipsilateral hind limb was observed. Animals in the sham group received surgery identical to those described but without nerve ligation. Under isoflurane anesthesia, the SNI surgery was also performed with a 5.0 silk tight ligation of the tibial and common peroneal nerves followed by transection and removal of a 3-5 mm nerve portion. However, the third peripheral branch of the sciatic nerve, the sural nerve, remained intact, and any contact or stretch to this nerve was carefully avoided. All the animal procedures performed in this study were approved by the Animal Care Committee of Duke University Medical Center. The numbers of mice used in different experiments were summarized in Table 1.

TABLE 1

Sample size and numbers of mice used in each experiment.
A total of 448 mice were used in this study.

| Experiment | Sample size | Number of Groups | Number of Samples | Number of Mice |
|---|---|---|---|---|
| 1. In vivo | | | | |
| 1.1 Behavioral test | n = 5-6 mice | 31 | 173 mice | 173 |
| 1.2 RT-PCR | n = 4-5 mice | 4 | 17 mice | 17 |
| 1.3 CSF Elisa analysis | n = 4 mice | 5 | 20 mice | 20 |
| 1.4 Elisa for DRG tissues | n = 4 mice | 6 | 24 mice | 24 |
| 1.5 Immunohistochemistry | | | | |
| 1.5.1 DRG tissues | n = 4-5 mice | 12 | 51 mice | 51 |
| 1.5.2 Spinal cord tissues | n = 4-5 mice | 7 | 31 mice | 31 |
| 2. Ex vivo | | | | |
| 2.1 Patch-clamp recording | n = 5 neurons | 8 | 40 neurons | 22 |
| 3. In vitro | | | | |
| 3.1 BMSCs culture | | | | |
| 3.1.1 Flow cytometric analysis | n = 6 cultures | 5 | 30 cultures | 15 |
| 3.1.2 Elisa | n = 4-8 cultures | 8 | 36 cultures | 20 |
| 3.1.3 Transell chemotaxis | n = 4 cultures | 5 | 20 cultures | 10 |
| 3.1.4 RT-PCR | n = 3 cultures | 2 | 6 cultures | 3 |
| 3.1.5 Intrathecal injection | n = 125 cultures | | | 62 |
| Total number of mice | | | | 448 |

Drugs and Administration

TGF-β1, TGF-0 neutralizing antibody, TNF and CXCL12/SDF-1α were purchased from R&D, LPS from Sigma. AMD3100 (CXCR4 antagonist) and SB431542 (TGF-β1R inhibitor) were purchased from Selleckchem. IL-10 neutralizing antibody was purchased from Biolegend, and normal Rabbit IgG were purchased from Santa Cruz. For intrathecal injection, spinal cord puncture was made with a 30-G needle between the L5 and L6 level to deliver reagents (10 μL) or cells (1 or $2.5 \times 10^5$ cells in 10 μL PBS) to the cerebral spinal fluid (Hylden, et al. Eur. J. Pharmacol. 1980, 67, 313-316). Before injection, BMSCs were washed with 0.01 M phosphate buffer saline (PBS) for three times, centrifuged for 5 min at 1,000 g, and then resuspended in PBS. In some cases, BMSCs were incubated with the Vybrant™ CM-Dil cell-labeling solution (Molecular Probes) for 20 minutes at 37° C. Cells were then washed three times with PBS and resuspended.

Tgfβ1 siRNA (Catalog: J-040652-06), Cxcr4 siRNA (Catalog: J-060184-06) and Non-targeting siRNA (Catalog: D-0018100-01-20) were purchased from Thermo Scientific Dharmacon. SiRNA was dissolved in RNase-free water at 1 μg/μL as stock solution and mixed with transfection reagent polyethyleneimine (PEI, Fermentas) and normal saline before use. Specifically, 1 μg siRNA was dissolved in 3.3 μL of PEI and 66 μL of normal saline (Kawasaki, et al. Nat. Med. 2008, 14, 331-336).

BMSCs Culture and Flow Cytometry Analysis

Primary cultures of BMSCs were obtained from CD-1 donor mice under aseptic conditions. The mice were sacrificed with isoflurane and the both ends of the tibiae and femurs were cut off by scissors. A syringe fitted with 20-gauge needle was inserted into the shaft of the bone, and bone marrow was flushed out with culture medium (modified Eagle's medium containing 10% fetal bovine serum, 2 mM L-glutamine, 100 U/mL penicillin and 100 μg/mL streptomycin, 250 μg/mL Fungizone, all obtained from Gibco). After the centrifuge at 1000 g for 5 min at room temperature, the pellet was resuspended in 2 mL fresh warm culture medium and mechanically dissociated, and the suspension was passed through a 40-μm cell strainer to remove debris. After the centrifuge the cells were resuspended at a concentration of $1 \times 10^6$ cells/mL. The cells were then incubated at 37° C. in 5% CO2 in 75 cm2 cell culture flasks or 6-well culture plates. After 24 hours, cells were washed gently with PBS and replaced with fresh culture media. Adherent cells were further cultured with a medium change every 2-3 days until confluence was reached (also see FIG. 11).

The property of expanded cells was assessed by flow cytometry. The adherent cells were then harvested by incubation with 0.25% trypsin/1 mM EDTA, washed with PBS and counted by the hemocytometer. A single cell suspension of 1×106 cells was placed in 0.05 mL of staining buffer (eBioscience). The cells were incubated with saturating concentrations of fluorescein isothiocyanate (FITC)-conjugated monoclonal antibodies against CD45 (1:400, eBioscience) and CD90 (1:400, eBioscience) for 20 minutes on ice in the dark. Isotype matched FITC-conjugated immunoglobulin G antibodies (1:400, eBioscience) were used as controls. Cells were then washed three times with staining buffer, centrifuged at 1000 g for 5 minutes, and resuspended in 0.5 mL ice cold staining buffer. Flow cytometry analyses were performed on Becton-Dickinson FACS Vantage Sorter Flow Cytometer (BD Biosciences) and analyzed using FlowJo analysis software (TreeStar).

ELISA

Mouse TGF-β1, IL-10, and CXCL12/SDF-1α ELISA kits were purchased from R&D Systems. ELISA was performed using BMSCs culture medium or cell lysate, CSF, and DRG tissue. Cultured cells and DRGs were homogenized in a lysis buffer containing protease and phosphatase inhibitors. CSF was collected from cisterna magna 4 or 28 days after intrathecal injection of BMSCs and diluted at 1:10 with Calibrator Diluent RD5-53 (1×, Quantikine Elisa, R&D). For each assay, 50 μg proteins, 50 μL of culture medium, or 5 μLt of CSF were used and ELISA was conducted according to manufacturer's instructions. The standard curve was included in each experiment.

Immunohistochemistry

After appropriate survival times, animals were deeply anesthetized with isoflurane and perfused through the ascending aorta with PBS, followed by 4% paraformaldehyde with 1.5% picric acid in 0.16 M phosphate buffer. After the perfusion, the lumbar spinal cord segments and DRGs were removed and postfixed in the same fixative overnight. Spinal cord sections (30 µm, free-floating) and DRG sections (12 µm) were cut in a cryostat and processed for immunofluorescence as described previously (Berta et al. J. Clin. Invest. 2014, 124, 1173-1186.). The sections were first blocked with 2% goat or horse serum for 1 h at room temperature. The sections were then incubated overnight at 4° C. with the following primary antibodies: GFAP antibody (mouse, 1:5000; Millipore Bioscience Research Reagents), IBA-1 antibody (rabbit, 1:1000, Wako), CGRP antibody (rabbit, 1:1000, Abcam), ATF3 antibody (rabbit, 1:1000, Santa Cruz), NeuN antibody (mouse, 1:1000, Millipore), and CD90 antibody (rat, 1:200, BD Pharmingen). The sections were then incubated for 1 h at room temperature with cyanine 3 (Cy3)- or FITC-conjugated secondary antibodies (1:400; Jackson ImmunoResearch). Fluorescein labeled GSLI-isolectin B4 (Vector laboratories) was used to perform IB4 staining (5 µg/mL) for 2 h at room temperature. For double immunofluorescence, sections were incubated with a mixture of polyclonal and monoclonal primary antibodies, followed by a mixture of FITC- and Cy3-conjugated secondary antibodies. In some cases DAPI (Vector laboratories) was used to stain cell nucleus. The stained sections were examined with a Nikon fluorescence microscope, and images were captured with a CCD Spot camera. We collected 6 spinal cord or DRG sections from each mouse for quantification. The intensity of fluorescence was analyzed using NIH Image J software. Some sections were also evaluated with a confocal microscope (Zeiss 510 inverted confocal).

Trafficking of BMSCs to DRGs

To examine the distribution of transplanted CM-Dil-labeled BMSCs following intrathecal injection, lumbar spinal cord segments and DRGs (L1-L6) were collected. For quantitative analysis of engrafted cells in DRGs, and 10 sections (12 µm) from each DRG were examined for the labeled BMSCs.

Quantitative Real-Time RT-PCR

Spinal dorsal horn tissues of L4-L5 segments were rapidly isolated. Total RNA was extracted using RNeasy Plus Mini kit (Qiagen) and 0.5-1 µg of RNA was reverse-transcribed. Specific primers including GAPDH control were designed using IDT SciTools Real-Time PCR software. Gene-specific mRNA analyses were performed using the MiniOpticon Real-Time PCR system (BioRad). Quantitative PCR amplification reactions contained the same amount of Reverse transcription (RT) product, including 7.5 µL of 2×iQSYBR-green mix (BioRad) and 100-300 nM of forward and reverse primers in a final volume of 15 µL. The primer sequences were described in Xu, et al. (Ann. Neurol. 2013, 74, 490-495). Primer efficiency was obtained from the standard curve and integrated for calculation of the relative gene expression, which was based on real-time PCR threshold values of different transcripts and groups.

Transwell Migration Assay

The migratory ability of BMSCs was determined using Transwell plates (Corning Costar, 6.5 mm in diameter with 8 µm pore filters). In brief, $5×10^4$ cells in 100 µL, serum-free medium were added into the upper well, and 600 µL, of CXCL12-containing medium was placed in the lower well of a Transwell plate. Following incubation for 5 h (37° C., 100% humidity, 5% $CO_2$ in air), the number of cells that had migrated to the lower side of the filter was counted under a light microscope at ×200 magnification, and the data were presented as the average number of migratory in five randomly-selected fields. Each experiment was performed in triplicate, and the data were averaged for statistical analysis.

Patch-Clamp Recordings in Spinal Cord Slices

A portion of the lumbar spinal cord (L4-L5) was removed from mice (4-7 weeks old) under urethane anesthesia (1.5-2.0 g/kg, i.p.) and kept in pre-oxygenated ice-cold Krebs solution (Xu, et al. Ann. Neurol. 2013, 74, 490-495). Transverse slices (400-600 µm) were cut on a vibrating microslicer. The slices were perfused with Kreb's solution (8-10 mL/min) that was saturated with 95% $O_2$ and 5% $CO_2$ at 36° C. for at least 1-3 h prior to experiment. The Kreb's solution contained (in mM): NaCl 117, KCl 3.6, $CaCl_2$ 2.5, $MgCl_2$ 1.2, $NaH_2PO_4$ 1.2, $NaHCO_3$ 25, and glucose. The whole-cell patch-clamp recordings were made from lamina IIo neurons in voltage-clamp mode. Patch pipettes were fabricated from thin-walled, borosilicate, glass-capillary tubing (1.5 mm outer diameter; World Precision Instruments). After establishing the whole-cell configuration, neurons were held their holding potentials at −70 mV for recording sEPSCs. The resistance of a typical patch pipette is 5-10 M. The internal solution contained the following (in mM): 135 potassium gluconate, 5 KCl, 0.5 $CaCl_2$, 2 $MgCl_2$, 5 EGTA, 5 HEPES, and 5 ATP-Mg. Membrane currents were amplified with an Axopatch 200 A amplifier (Molecular Devices) in voltage-clamp mode. Signals were filtered at 2 kHz and digitized at 5 kHz. Data were stored with a personal computer using pClamp 6 software and analyzed with Mini Analysis (Synaptosoft).

Whole-Cell Patch Clamp Recordings in Whole Mount DRG

The L4-L5 whole mount DRGs were carefully removed from the vertebral column and placed in cold oxygenated ACSF as detailed in Lee et al. (Cell 2014, 157, 1393-1404). The connective tissue was gently removed under a microscope and the ganglia were digested with a mixture of 1.0 mg/mL protease and 1.6 mg/mL collagenase (Sigma) for 30 min at 37° C. The ganglion was transferred into a holding chamber containing normal Mg2+-free ACSF with CNQX (2 µM) bubbled with 95% $O_2$ and 5% $CO_2$ at room temperature. Whole-cell current clamp recordings were performed at room temperature (28° C.) to measure action potentials with Axopatch-200B amplifier (Axon Instruments). The patch pipettes were pulled from borosilicate capillaries (Chase Scientific Glass Inc.). When filled with the pipette solution, the resistance of the pipettes was 4-5 MΩ. The recording chamber (300 µL) was continuously superfused (3-4 mL/min). Series resistance was compensated for (>80%), and leak subtraction was performed. Data were low-pass-filtered at 2 KHz, sampled at 10 KHz. The pClamp10 (Axon Instruments) software was used during experiments and analysis.

Behavioral Analysis

Animals were habituated to the testing environment daily for at least 2 days before baseline testing. The room temperature and humidity remained stable for all experiments. All the behaviors were tested blindly. For testing mechanical sensitivity, mice were confined in boxes placed on an elevated metal mesh floor and their hindpaws were stimulated with a series of von Frey hairs with logarithmically increasing stiffness (0.02-2.56 g, Stoelting), presented perpendicularly to the central plantar surface. The 50% paw withdrawal threshold was determined by Dixon's up-down method. Mechanical allodynia after SNI was also assessed by frequency response (expressed as percentage response) to a low-threshold von Frey hair (0.16 g, 10 times). Thermal sensitivity was tested using Hargreaves radiant heat apparatus (IITC Life Science), the basal paw withdrawal latency was adjusted to 9-12 s, with a cutoff of 20 s to prevent tissue damage. Randall-Selitto Analgesiometer (Ugo basile, Italy) was used to examine mechanical sensitivity by applying ascending pressure to a mouse tail, with a cutoff threshold of 250 g to avoid tissue damage. A Rota-rod system (IITC Life Science Inc.) was used to assess the motor function. Mice were tested for three trails separated by 10 min intervals. During the tests, the speed of rotation was accelerated from 2 to 20 r.p.m. in 3 min. The falling latency was recorded and averaged.

To test spontaneous/ongoing pain measurement, a single trial conditioning protocol for conditioned place preference (CPP) was used as described in King et al. (Nat. Neurosci. 2009, 12, 1364-1366) and Xu et al. (Ann. Neurol. 2013, 74, 490-495). All mice underwent a 3-day pre-conditioning habituation and animal behavior was video-recorded. Analyses of the pre-conditioning (baseline) behavior showed no pre-existing chamber preference. On the conditioning day, mice received the vehicle (saline) control paired with a randomly chosen chamber in the morning, and then the appropriate treatment (clonidine, 10 µg, i.t.) paired with the other chamber 4 h later. Chamber pairings were counterbalanced. On the test day, 20 h following the afternoon pairing, mice were placed in the CPP box with access to both chambers and the behavior was recorded for 15 min and analyzed by ANY-maze software for chamber preference.

Statistics

All data were expressed as mean±SEM. The sample size for each experiment was summarized in Table 1 and also described in figure legends. Behavioral data were analyzed by 2-way repeated-measures ANOVA followed by Bonferroni post hoc test. Differences between 2 groups were compared using Student t test. One-way ANOVA was used for the statistical analyses in other tests. The criterion for statistical significance was $P<0.05$.

Example 2

Early or Late Treatment of BMSCs Via Intrathecal Route Produces Long-Term Relief of Neuropathic Pain after CCI Neuropathic pain was induced in mice via chronic constriction injury (CCI) of the sciatic nerve. In this model, neuropathic pain was characterized by mechanical allodynia and heat hyperalgesia; both lasted >5 weeks but recovered after 6-8 weeks (FIG. 1A and FIG. 1B). To test the hypothesis that BMSCs would alleviate behavioral signs of neuropathic pain, BMSCs were injected intrathecally into spinal cerebrospinal fluid (CSF) via a lumbar puncture, 4 days after CCI when neuropathic pain developed but had not reached to the peak yet. BMSCs were characterized in FIG. 11 with a purity of 88%, and $1.0\times10^5$ or $2.5\times10^5$ BMSCs (prepared in 10 µL PBS) were collected for intrathecal injection. As shown in FIG. 1A and FIG. 1B, a single intrathecal injection of BMSCs, given on CCI day 4, produced a rapid (within 1 day) inhibition of CCI-induced mechanical allodynia and thermal hyperalgesia. Notably, these antinociceptive effects lasted for >5 weeks following either low-dose or high-dose treatment of BMSCs (FIG. 1A and FIG. 1B). The effects of BMSCs on established late-phase neuropathic pain, 14 days after CCI, were examined next. As shown in FIG. 1C and FIG. 1D, intrathecal BMSCs effectively reversed mechanical allodynia and thermal hyperalgesia in a dose-dependent manner: low-dose of BMSCs ($1.0\times10^5$) only reversed mechanical allodynia and heat hyperalgesia for 1 week, whereas high-dose of BMSCs ($2.5\times10^5$) reversed these neuropathic pain symptoms for >4 weeks (FIG. 1C and FIG. 1D).

Given the limitations of measuring evoked pain and withdrawal reflex, it was tested whether BMSCs would also alleviate nerve injury-induced ongoing pain, based on the finding that negative reinforcement can unmask ongoing neuropathic pain in a 2-chamber conditioned place preference (CPP) test. The paradigm of the CPP tested was described in FIG. 1E. The result showed that mice spent more time in the chamber paired with the analgesic clonidine than in the chamber paired with vehicle injection (FIG. 1F), indicating that mice developed ongoing pain after CCI. Importantly, CCI-induced ongoing pain was abolished by the intrathecal treatment of BMSCs ($2.5\times10^5$ cells, FIG. 1F).

Figure 2:
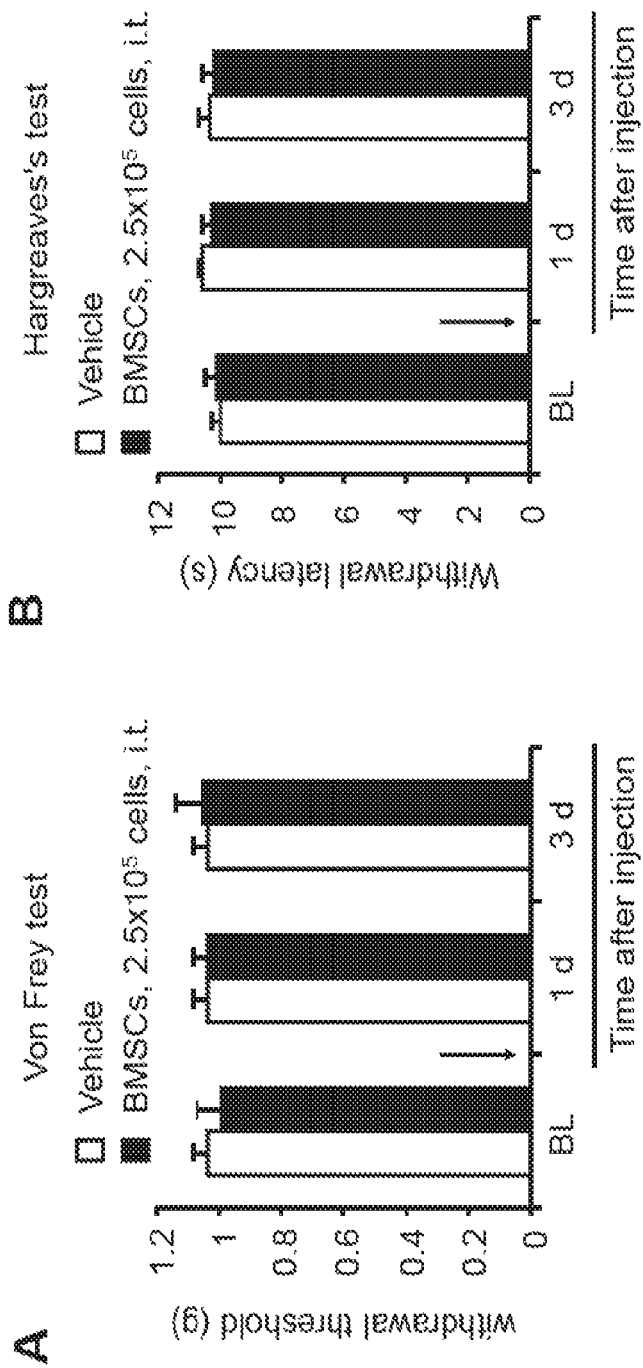
FIG. 2 shows that baseline pain and motor function are not altered by intrathecal injection of BMSCs. (A-C) Baseline pain sensitivity evaluated in von Frey test for mechanical sensitivity (A), Hargreaves' test for heat sensitivity (B), and Randall-Selitto test for mechanical sensitivity. (D) Rota-Rod test for the evaluation of motor function. n=6 mice/group.
Figure 2:
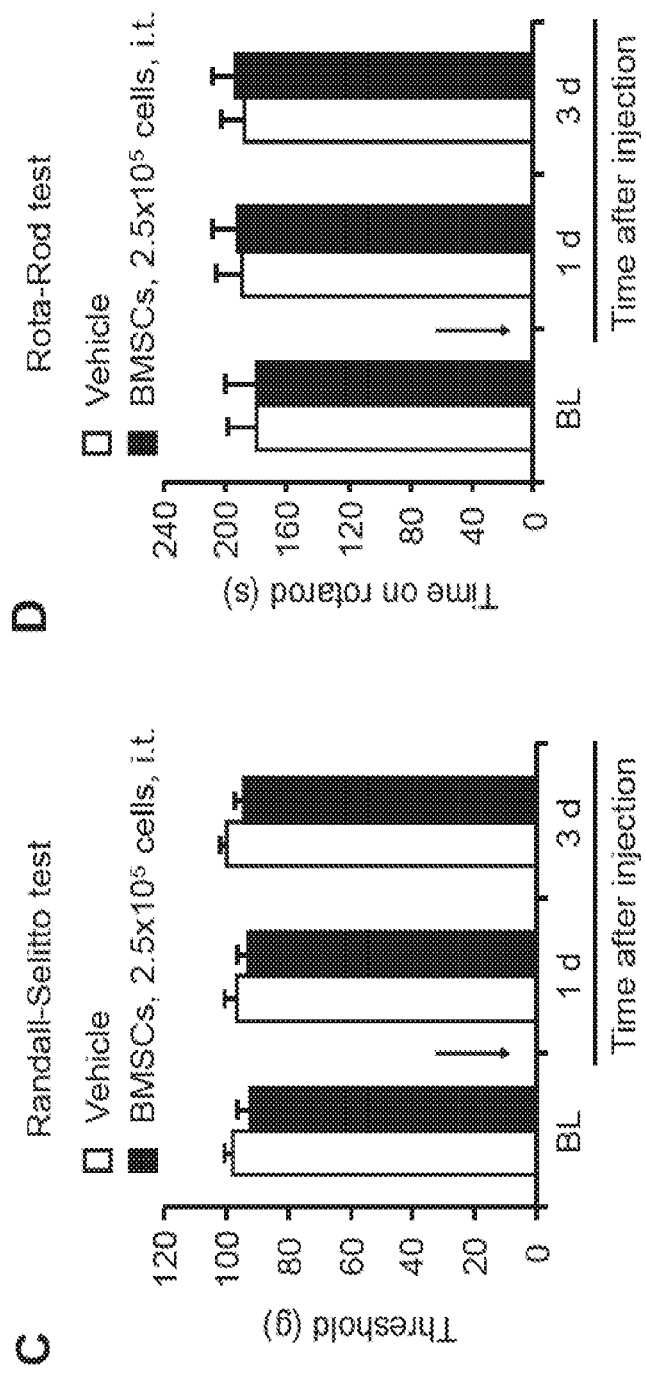

While chronic pain is destructive, physiological pain is protective. It was also tested whether intrathecal BMSCs would affect physiological pain (basal pain) in the normal conditions. Notably, intrathecal BMSCs treatment, even at a high dose ($2.5\times10^5$), did not change mechanical and thermal pain thresholds in naïve mice (FIG. 2A-C). Neither did this treatment affect motor function, as evaluated in Rota-rod test (FIG. 2D). Collectively, these data suggest that intrathecal injection of BMSCs, either in the early or late phase of CCI, can elicit long-lasting relief of neuropathic pain symptoms, without affecting baseline pain thresholds (physiological pain states) and motor function.

Example 3

Figure 3:
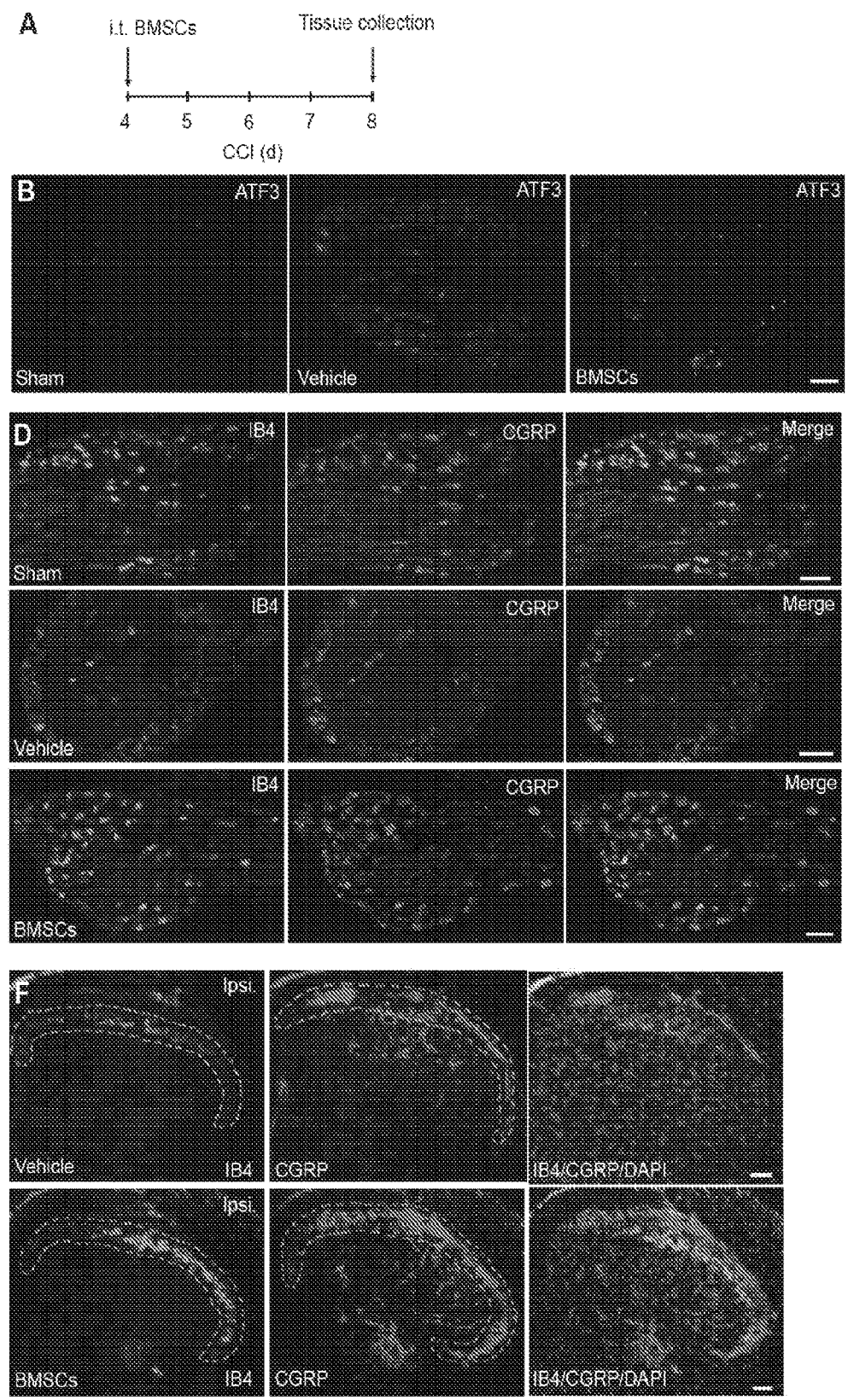
FIG. 3 shows that intrathecal administration of BMSCs inhibits CCI-induced up-regulation of ATF3 in DRG and reduces CCI-induced down-regulations of CGRP and IB4 in DRG and spinal cord dorsal horn. (A) Paradigm showing the time of BMSCs treatment (CCI-4 d) and tissue collection (CCI-8 d). (B-G) Inhibition of CCI-induced up-regulation of ATF3 (B, C) and down-regulations of IB4 and CGRP (D, E) in L4-L5 DRGs as well as down-regulations of IB4 and CGRP in L4-L5 spinal cord dorsal horn (F, G) by i.t. injection of BMSCs ($2.5 \times 10^5$ cells, 4 d after CCI). Scales, 50 μm. C, E, G are quantification results of ATF3 staining in DRGs (C), IB4 and CGRP staining in DRGs (E), and IB4 and CGRP staining in dorsal horns (G). *P<0.05, compared to sham or contralateral group; #P<0.05, n=4-5 mice/group.
Figure 3:
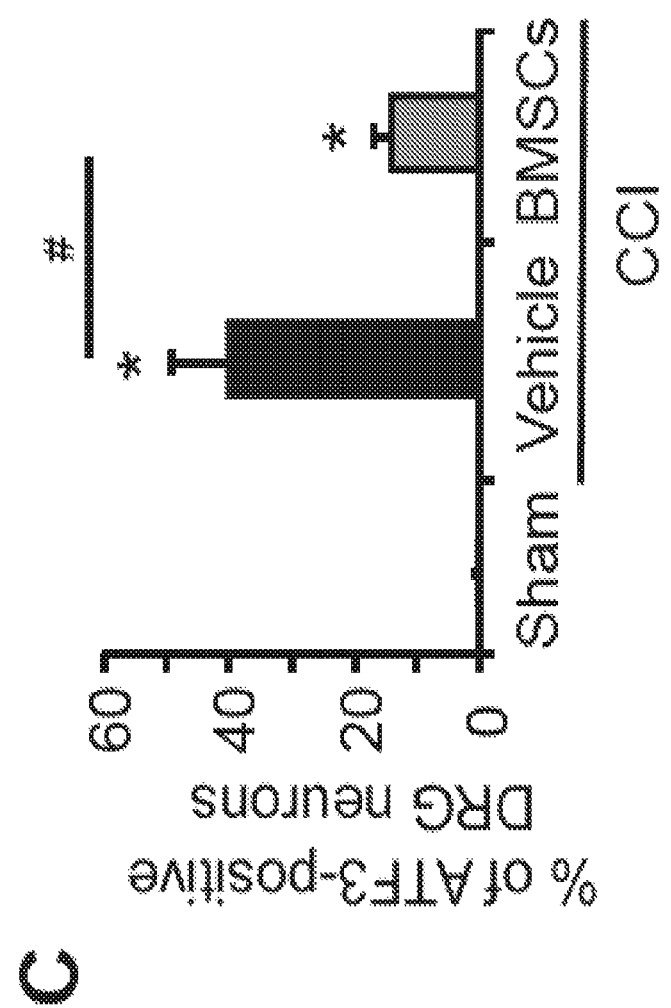
Figure 3:
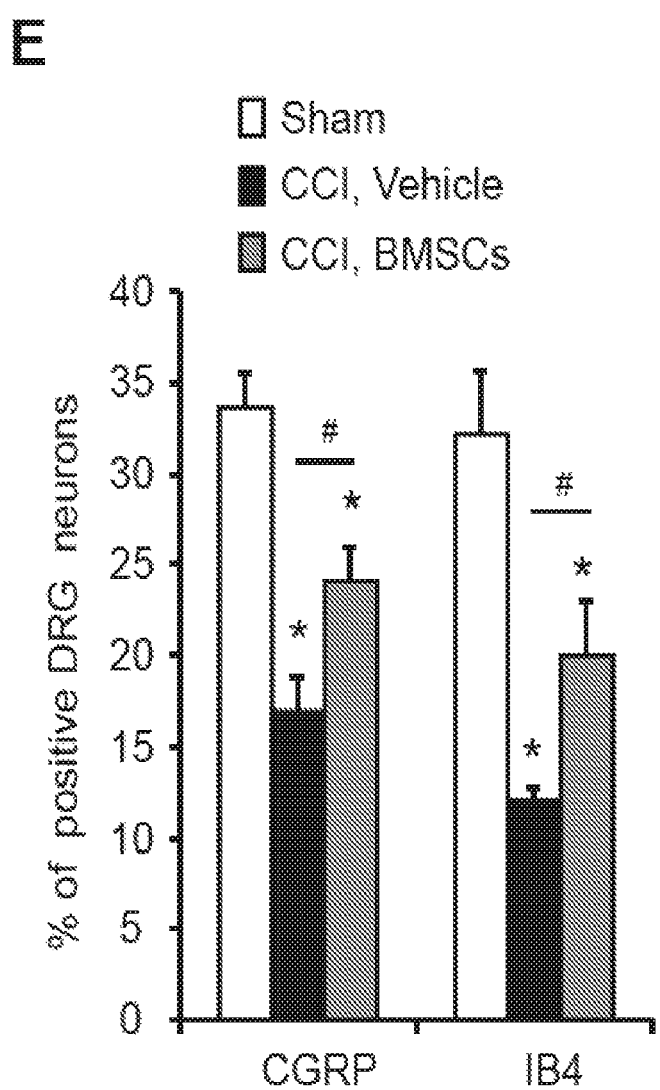
Figure 3:
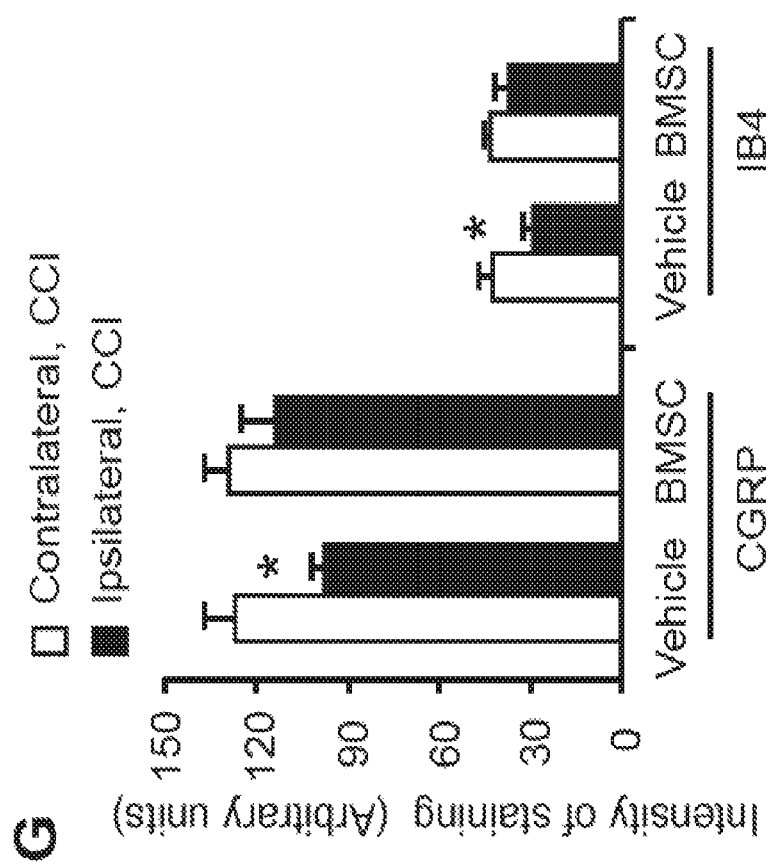

Intrathecal BMSCs Protect Primary Sensory Neurons from CCI-Induced Axonal Injury The activating transcription factor 3 (ATF3) is a widely used marker for DRG neuron injury. ATF3 immunoreactivity (IR) was barely detected in DRG neurons of sham surgery mice, but was markedly increased to 40% neurons in L4-L5 DRGs after CCI (FIG. 3A-C). Intrathecal BMSCs treatment ($2.5\times10^5$), given 4 days after CCI, inhibited CCI-induced ATF3 expression in DRG neurons 8 days after CCI, and the percentage of ATF3-IR neurons was reduced to 14% after the BMSCs treatment (FIG. 3A-C). Nerve injury is also known to down-regulate the neuropeptide calcitonin gene-related peptide (CGRP) in peptidergic neurons and isolectin B4 (IB4) binding in non-peptidergic neurons in DRG. Notably, intrathecal BMSCs reversed CCI-induced down-regulations of both CGRP and IB4 staining in DRG neurons (FIG. 3D and FIG. 3E) and also in their central axonal terminals in the spinal cord dorsal horn (FIG. 3F and FIG. 3G). These results suggest that intrathecal BMSCs can protect DRG neurons from axonal injury.

Example 4

Intrathecal BMSCs Control Neuroinflammation in DRG and Spinal Cord after CCI

Neuroinflammation is an inflammatory response in the peripheral and central nervous system and has been strongly implicated in the genesis of neuropathic pain. CCI caused a marked increase in IBA-1-labeled macrophages in the injured L4-L5 DRGs, but this increase on CCI-day 8 was blocked by intrathecal BMSCs treatment ($2.5\times10^5$) given on CCI-day 4 (FIG. 4A-C). Quantitative PCR revealed that CCI also produced upregulations of Gfap (marker for satellite glial cells) and Il1β and Il6 but not Tnf (key pro-inflammatory cytokines) in the L4-L5 DRGs, and all these upregulations were suppressed by BMSCs treatment (FIG. 4D).

Neuroinflammation is also characterized by activation of glial cells including microglia and astroctyes in spinal cord, and this activation plays an essential role in the pathogenesis of neuropathic pain by producing IMP, IL-6, and TNF to enhance spinal cord synaptic transmission. At 8 days post-surgery, CCI caused marked increases in IR of GFAP (astrocyte marker) and IBA-1 (microglial marker) as well as morphological changes of astrocytes and microglia in the ipsilateral side of the spinal dorsal horn. All these glial changes were attenuated by BMSCs treatment (FIG. 4E and FIG. 4F). Quantitative PCR result showed that CCI induced upregulations of Iba1, Il1β, Il6, and Tnf transcripts in the L4-L5 spinal dorsal horn, which were all suppressed by BMSCs (FIG. 4G). Thus, intrathecal BMSCs can effectively control neuroinflammation in the neuro-axis of pain including DRG and spinal cord.

Example 5

BMSCs Release TGF-β1 to Inhibit Neuropathic Pain

Given the rapid analgesic effect observed on day 1, it was reasoned that BMSCs might control neuropathic pain by paracrine signaling through secretion of potential "pain killers." The anti-inflammatory cytokines TGF-β and IL-10 have been implicated in beneficial effects of BMSCs in asthma and sepsis. TGF-β and IL-10 also inhibit neuropathic pain and spinal neuroinflammation after nerve injury. To assess their involvement in BMSCs-elicited pain relief, TGF-β1 and IL-10 release were measured in the culture medium of BMSCs. High basal release of TGF-β1 (120 pg/mL) was detected, but a very low basal release of IL-10 (<5 pg/mL, FIG. 5A) was detected. It was next examined whether inflammatory challenge would boost the release of IL-10 and TGF-β1. Exposure of BMSCs to TNF-α or LPS significantly increased TGF-β1 but not IL-10 release (FIG. 5A). Furthermore, TGF-β1 release was examined in cerebrospinal fluid (CSF) collected from naïve and CCI mice with or without BMSCs-treatment. TGF-β1 release in CSF did not increase in CCI mice but was substantially increased after intrathecal injection of BMSCs in CCI mice (FIG. 5B).

To determine whether TGF-β1 and IL-10 contribute to the antinociceptive effects of BMSCs in neuropathic pain, mice were treated with a specific neutralizing antibody against TGF-β or IL-10, 3 days after BMSCs injection (i.e. 7 days after CCI). Strikingly, the anti-allodynic effect of BMSCs was reversed by intrathecal TGF-β neutralization but not by control serum and IL-10 neutralization (FIG. 5C). The reversal by the TGF-β neutralization was transient and recovered after 24 h (FIG. 5C). TGF-β neutralization was further tested at additional two time points, an earlier time point (1 day after BMSCs injection) and a later time point (24 days after BMSCs injection). Notably, TGF-β antibody was still capable of reversing BMSCs-induced inhibition of allodynia and hyperalgesia at 1 or 24 days after BMSCs injection (FIGS. 12A-D). At 28 days after BMSCs injection, TGF-β1 levels in L5 DRGs but not in CSF were still elevated compared to vehicle control (FIGS. 12E-F).

To further validate a critical role of TGF-β1 release for neuropathic pain relief of BMSCs, TGF-β1 expression in BMSCs was knocked down by treating BMSCs cultures with a specific siRNA (1 µg/mL) for 18 h. This treatment resulted in 67% reduction in TGF-β1 release and 55% reduction in TGF-β1 expression in BMSCs cultures compared to the non-targeting siRNA treatment (FIG. 5D). BMSCs-induced anti-allodynic effect was compromised for several days after intrathecal administration of siRNA-treated BMSCs (FIG. 5E and FIG. 13).

Since only 88% cells in bone marrow cultures expressed the stem cell marker CD90 (FIG. 11C), it was next assessed whether the remaining CD90-negative cells would also modulate pain via TGF-β1. After cell sorting, CD90-negative cells were amplified and collected for testing their analgesic effects. Intrathecal injection of these CD90-negative cells, 2 weeks after CCI, only elicited mild and transient inhibition of CCI-induced allodynia and hyperalgesia (FIGS. 14A-B). Furthermore, these CD90-negative cells secreted much less TGF-β1 compared to CD90-positive cells (FIG. 14C). Together, these results strongly suggest that intrathecal BMSCs inhibit neuropathic pain symptoms via releasing TGF-β1.

Example 6

Exogenous TGF-β1 Attenuates Neuropathic Pain Through TGF-βR1

To further test the hypothesis that TGF-β1 is sufficient to alleviate behavioral signs of neuropathic pain, the antinociceptive effects of exogenous recombinant TGF-β1 on CCI-induced mechanical allodynia and heat hyperalgesia were evaluated. Intrathecal TGF-β1 was highly potent in inhibiting neuropathic pain; both mechanical allodynia (FIG. 5F) and thermal hyperalgesia (FIG. 15A) at 5 days after CCI were dose-dependently inhibited by very low doses of TGF-β1 (2 ng=16 pmol, 10 ng=78 pmol). This reversal recovered after 24 h (FIG. 5F and FIG. 15A). The effects of TGF-β1 on established of neuropathic pain were also examined. TGF-β1 effectively inhibited late-phase neuropathic pain on post-CCI day 21 d (FIG. 5G and FIG. 15B). It was next tested whether TGF-β receptor 1 (TGF-βR1), the major receptor for canonical signaling of TGF-β1, would be responsible for the anti-allodynic effects of TGF-β1. Intrathecal injection of SB431542 (100 pmol), a potent and selective inhibitor of TGF-βR1, eliminated the anti-allodynic and anti-hyperalgesic effects of TGF-β1 (10 ng) in CCI mice (FIG. 5H and FIG. 15C).

Example 7

TGF-β1 Modulates Excitatory Synaptic Transmission in Spinal Cord Neurons after CCI Via TGF-βR1

Spinal cord synaptic plasticity (central sensitization) plays an essential role in driving neuropathic pain. Spinal cord slices were prepared from sham and CCI mice (4 d) for patch-clamp recordings in lamina IIo neurons. These interneurons from a pain circuit by receiving input from C-fiber afferents and sending output to lamina I projection neurons. CCI resulted in significant increases in the frequency and amplitude of spontaneous excitatory postsynaptic currents (sEPSCs) in IIo neurons (FIG. 6A and FIG. 6B). The EPSCs are mediated by AMPA glutamate receptors and their increases in lamina IIo neurons may drive pathological pain. Superfusion of spinal cord slices with TGF-β1 (2 or 10 ng/mL) dose-dependently and rapidly (with 2 min) blocked the CCI-induced increases in sEPSC frequency and amplitude (FIG. 6A and FIG. 6B). Moreover, this blockade of TGF-β1 (10 ng/mL) signaling was abrogated by the TGF-βR1 antagonist SB431542 (10 μM, FIG. 6A and FIG. 6C). For comparison, superfusion of TGF-β1 (10 ng/mL) had no effects on sEPSC frequency and amplitude in sham mice (FIG. 6A and FIG. 6B), suggesting that TGF-β1 selectively modulates nerve injury-induced synaptic plasticity but not basal synaptic transmission.

Example 8

TGF-β1 Modulates Neuronal Excitability in DRG Neurons after CCI Via TGF-βR1

Neuropathic pain is also driven by hyperexcitability of primary sensory neurons. The effects of TGF-β1 on the firing frequency of evoked action potentials in small-sized DRG neurons were tested using whole-mount DRG preparations from sham and CCI mice. Compared to sham surgery, CCI resulted in a profound increase in spike frequency in small-sized DRG neurons (FIG. 7A and FIG. 7B). TGF-β1 rapidly (2-5 min) and dose-dependently suppressed this increase. Further, SB431542 (10 μM) reversed this effect, conforming an essential involvement of TGF-β1R1 in TGF-β1 signaling (FIG. 7A and FIG. 7B).

Example 9

Intrathecal BMSCs Target the Injured Lumbar DRGs Via CXCL12-CXCR4 Axis

To determine the destination of the intrathecally implanted BMSCs in mice following nerve injury, BMSCs were labelled with a fluorescent dye DiI, and DRG and spinal cord tissues were collected 3 days after the intrathecal injection of DiI-labeled BMSCs (i.e. 7 days after CCI). Interestingly, many labeled DiI-BMSCs were found in the injured lumbar DRGs (L4-L6 DRGs that send axons to the sciatic nerve), 7 days after CCI (FIG. 8A). In contrast, only a few DiI-BMSCs were detected in the contralateral DRGs (L2-L6, FIG. 8A) or ipsilateral L2-L3 DRGs (FIG. 8A). DiI-labeled BMSCs were also found at the borders of the white matter of the L4-L6 spinal cord, especially in the ipsilateral dorsal horn (FIG. 16A).

Chemokines play an important role in chronic pain via regulating leukocyte trafficking, glial activation, and neuronal activities. Interestingly, CXCL12 (also named SDF-1) and its receptor CXCR4 were not only involved in neuropathic pain but also implied in BMSCs trafficking. CCI caused marked increase in CXCL12 levels in L4-L6 DRGs compared with that in sham control mice (FIG. 8B). Furthermore, transwell migration assay showed that CXCL12 induced migration of BMSCs in vitro, and the CXCR4 antagonist AMD3100 blocked the migration (FIG. 8C and FIG. 17).

To define the role of the CXCL12/CXCR4 axis in regulating the migration of BMSCs in vivo, BMSCs were treated with Cxcr4 siRNA or non-targeting control siRNA (1 μg/mL, 18 h) and observed 85% reduction in Cxcr4 mRNA levels after the siRNA treatment (FIG. 8D). Notably, BMSCs-induced inhibition of mechanical allodynia was gradually (5-7 days) compromised after intrathecal injection of siRNA-treated BMSCs (FIG. 8E). To check the effect of Cxcr4 knockdown on BMSCs trafficking, the ipsilateral L4-L6 DRGs from Cxcr4 siRNA and control siRNA-treated mice 7 d after the BMSCs injection were collected. Strikingly, the number of BMSCs migrating to the injured DRG was substantially reduced in the siRNA-treated group compared with the control group (22.6±5.4 vs. 280.8±54.3/ganglion, t-test, P<0.05, n=5 mice/group) (FIG. 8F and FIG. 8G).

Example 10

Long-Term Survival of BMSCs in DRGs of CCI Mice Following Intrathecal Injection

Figure 19A:
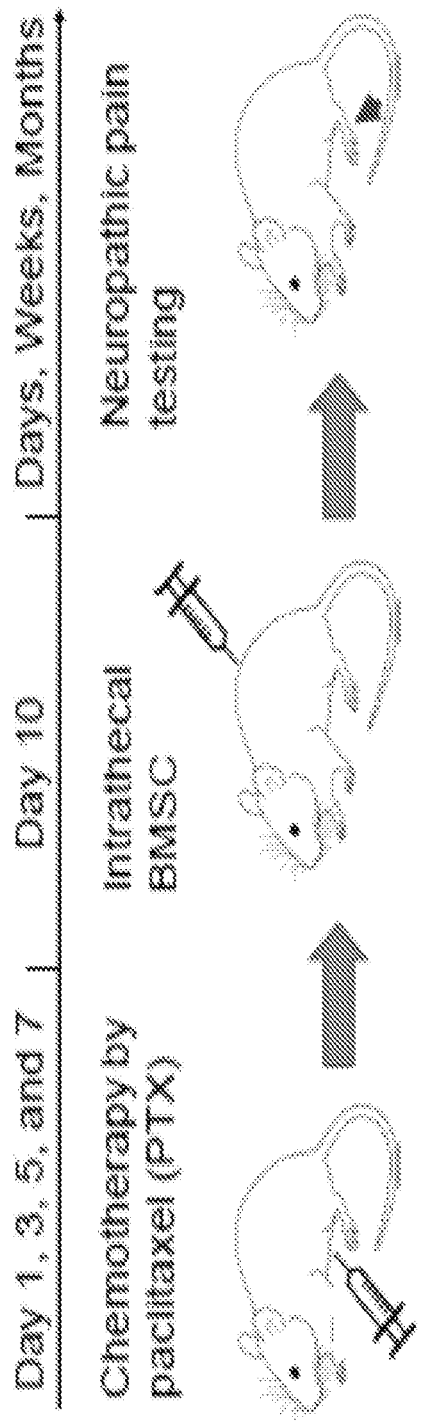

To define the destination and fate of intrathecally implanted BMSCs, ipsilateral L5 DRGs were collected 3-84 days after the intrathecal injection in CCI mice. The number of DiI-labeled BMSCs reached to a peak on day 3 and then gradually declined (FIG. 9A-B). Notably DiI-labeled BMSCs were detected in ipsilateral L5 DRGs even 56 days after the implantation (FIG. 9A-B), suggesting a long-term survival of BMSCs in DRGs. Double immunostaining results showed that the majority of DiI-labeled BMSCs still expressed CD90 28 days after CCI (FIG. 9C). The BMSCs were primarily localized on the edge of DRGs, and no evidence of new cell genesis for neurons (NeuN+), satellite glial cells (GFAP+), and monocytes (Iba1+) from the implanted BMSCs was found (FIG. 18A-B). Of interest, confocal images showed DiI uptake by neurons near the BMSCs, suggesting an interaction (molecule exchange) between the infiltrated BMSCs and neurons (FIG. 19A). However, the number of the labeled BMSCs dramatically reduced on day 70, and only a few BMSCs were seen on day 84 (FIG. 9B). Thus, the potential health risk of the intrathecally implanted BMSCs (e.g., conversion into tumor cells) should be very low.

Example 11

Early or Late Intrathecal Delivery of BMSCs Produces Long-Term Relief of Neuropathic Pain after Spared Nerve Injury (SNI)

Figure 1:
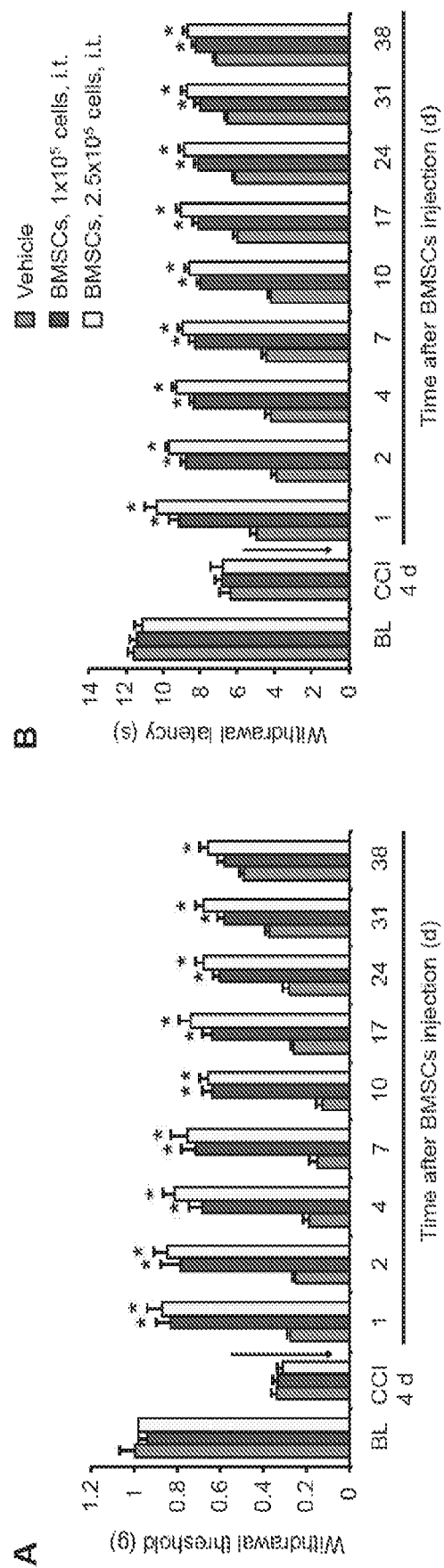
FIG. 1 shows that inhibition of CCI-induced evoked and ongoing neuropathic pain in mice by single intrathecal injection of BMSCs. (A and B) Prolonged inhibition of mechanical allodynia (A) and thermal hyperalgesia (B) for 5 weeks by early treatment of BMSCs (1.0 or $2.5 \times 10^5$ cells) via intrathecal (i.t.) injection, given 4 days after CCI. BL, baseline. *P<0.05, compared with vehicle (PBS), n=6 mice/group. (C and D) Reversal of mechanical allodynia (C) and thermal hyperalgesia (D) by late treatment of BMSCs (1.0 or $2.5 \times 10^5$ cells, i.t.), given 14 days after CCI. Arrows indicate the time of BMSCs injection. *P<0.05, compared with vehicle; #P<0.05, n=6 mice/group. (E) The paradigm for measuring ongoing pain using two-chamber conditioned place preference test. (F) CCI induced ongoing pain was abolished by the BMSCs treatment. *P<0.05, compared with saline, n=5 mice/group. Statistical significance was determined by 2-way repeated-measures ANOVA followed by Bonferroni post-hoc test (A-D) or Student's t test (F). All data are expressed as mean±S.E.M.
Figure 1:
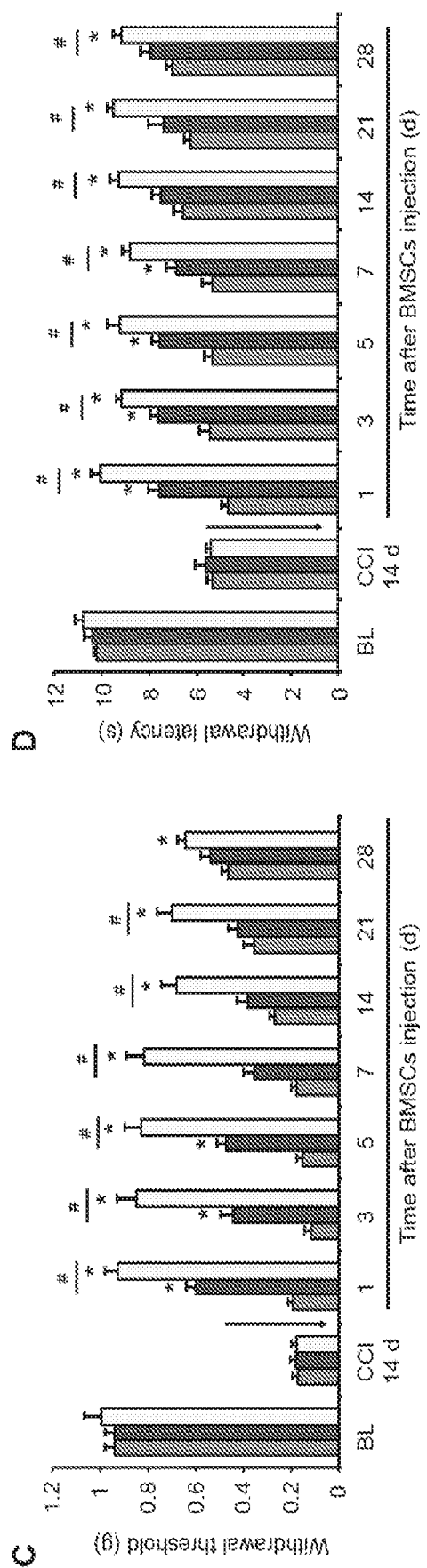
Figure 1:
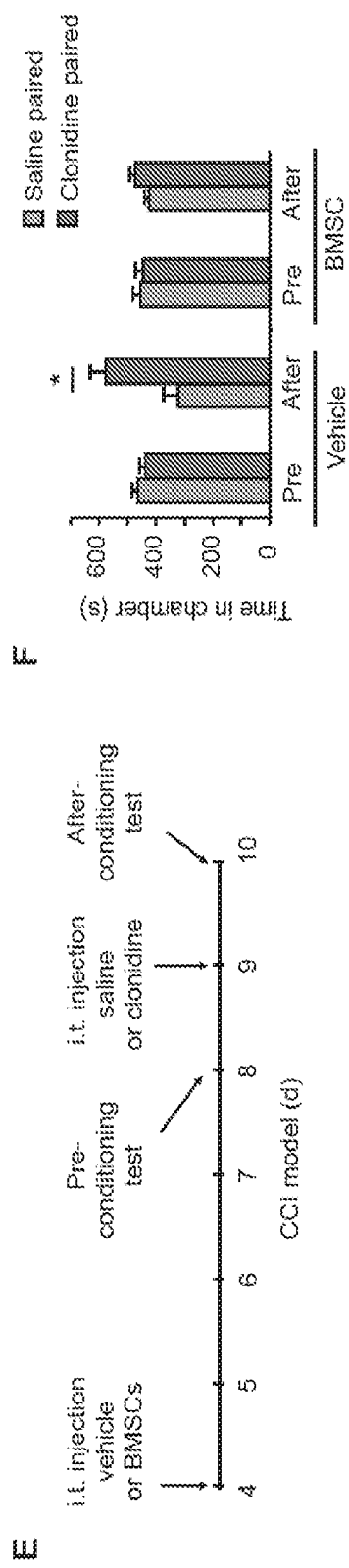

The analgesic efficacy of BMSCs was tested in a more persistent neuropathic pain model, induced by SNI. In this model, mechanical allodynia is rapidly induced within one day and maintains for several months in rodents. Intrathecal injection of BMSCs ($2.5 \times 10^5$), 4 days after SNI, produced a rapid (<1 day) and long-lasting (>42 days) inhibition of SNI-induced mechanical allodynia (reduction in paw withdrawal threshold, FIG. 10A). This anti-allodynic effect was more robust when mechanical allodynia was assessed by frequency (percentage) response to a single low-threshold von Frey hair (0.16 g, FIG. 10B). Intrathecal BMSCs ($2.5 \times 10^5$), given 3 weeks after SNI, also significantly reversed late-phase mechanical allodynia for >5 weeks (FIG. 10C-D), although the analgesic efficacy in the SNI model was not as great as that in the CCI model (FIG. 1). In this model, TGF-β1 was still responsible for BMSCs-induced analgesia, since the BMSCs-induced anti-allodynic effect was revered by TGF-β1 antibody, given 17 days after BMSCs injection (i.e. 21 days after SNI, FIG. 10E).

Example 12

Intrathecal Injection of BMSCs Produces Long-Term Relief of Neuropathic Pain after Chemotherapy Chemotherapy-induced peripheral neuropathy is the dose-limiting toxicity for commonly used anti-cancer agents and can lead to dose reductions or discontinuation of cancer therapy. Paclitaxel (PAX) is one of the most effective and commonly used drugs for chemotherapy; however, paclitaxel causes painful neuropathy in about 20% of cancer patients receiving standard doses and majority of patients receiving high doses of therapy. As such, the analgesic efficacy of BMSCs was also tested in a PAX-induced neuropathic pain model.

Paclitaxel (2 mg/kg, i.p.) was given on day 1, 3, 5 and 7, and BMSC were intrathecally injected on day 10 (FIG. 19A).

Figure 19B:
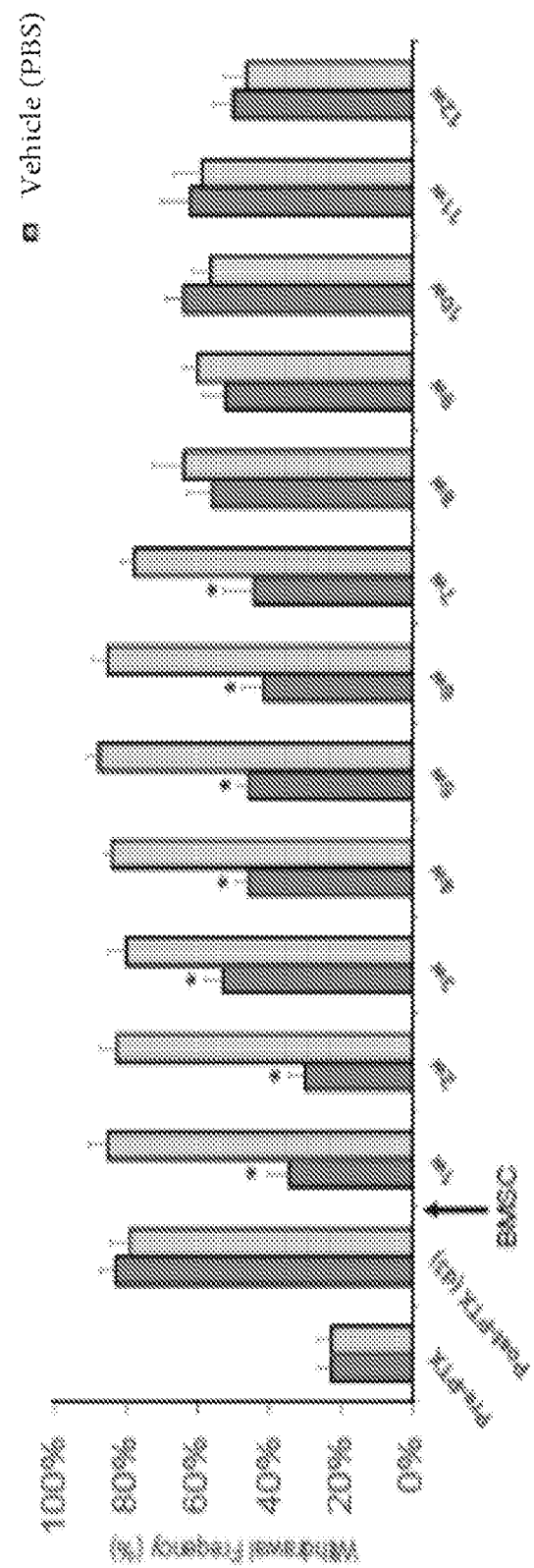

PAX-induced neuropathic pain (mechanical allodynia) was evaluated by paw withdrawal frequency to von Frey hair (0.4 g) stimuli (10×). Intrathecal BMSCs ($2.5 \times 10^5$) produced a rapid (1 week) and long lasting (7 weeks) reduction in PAX-induced mechanical allodynia (FIG. 19B).

Example 13

Intrathecal Injection of TGF-β Produces Long-Term Relief of Neuropathic Pain after Chemotherapy The analgesic efficacy of TGF-β1 was also tested in a PAX-induced neuropathic pain model. Paclitaxel (2 mg/kg, i.p.) was given on day 1, 3, 5, and 7. At 7 weeks following the first injection with Paclitaxel, mice were intrathecally injected with TGF-β1 (100 ng). PAX-induced neuropathic pain was evaluated by paw withdrawal frequency to von Frey hair (0.4 g) stimuli (10×). Intrathecal TGF-β1 transiently reversed PAX-induced mechanical allodynia for 3 hours following injection (FIG. 20).

8. CLAUSES

For reasons of completeness, various aspects of the invention are set out in the following numbered clauses:

Clause 1

A method of treating pain in a subject in need thereof, the method comprising administering to the subject a composition comprising bone marrow stromal cells (BMSCs).

Clause 2

The method of clause 1, wherein the composition is administered by injection.

Clause 3

The method of clause 2, wherein the composition is administered by intrathecal injection.

Clause 4

The method of clause 2, wherein the composition is administered by direct injection into the dorsal root ganglia.

Clause 5

The method of clause 1, wherein the pain comprises neuropathic pain, inflammatory pain, cancer pain, or a combination thereof.

Clause 6

The method of any one of clauses 1-5, wherein the pain is chronic.

Clause 7

The method of any one of clauses 1-6, wherein the subject is mammalian.

Clause 8

The method of any one of clauses 1-7, wherein the subject is human.

Clause 9

The method of any one of clauses 1-8, wherein the BMSCs are autologous BMSCs, heterologous BMSCs, or a combination thereof.

Clause 10

The method of clause 9, wherein the BMSCs are autologous BMSCs.

Clause 11

The method of clause 9, wherein the BMSCs are heterologous BMSCs.

Clause 12

The method of clause 1, wherein the BMSCs are derived from a cell line, a donor subject, or a combination thereof.

Clause 13

The method of any one of clauses 1-12, wherein about $0.5 \times 10^5$ to about $5.0 \times 10^7$ BMSCs are administered to the subject.

Clause 14

The method of any one of clauses 1-12, wherein at least about $0.5 \times 10^5$ BMSCs are administered to the subject.

Clause 15

The method of any one of clauses 1-14, wherein the pain is reduced or suppressed in the subject for at least about 30 minutes.

Clause 16

The method of clause 15, wherein the pain is reduced or suppressed in the subject for at least about 12 hours.

Clause 17

The method of clause 16, wherein the pain is reduced or suppressed in the subject for at least about 7 days.

Clause 18

The method of clause 17, wherein the pain is reduced or suppressed in the subject for at least about 2 weeks.

Clause 19

The method of clause 18, wherein the pain is reduced or suppressed in the subject for at least about 6 months.

Clause 20

The method of any one of clauses 1-19, wherein the BMSCs secrete TGF-β1.

Clause 21

The method of any one of clauses 1-19, wherein the BMSCs express CXCR4.

Clause 22

The method of any one of clauses 1-19, wherein the BMSCs secrete TGF-β1 and express CXCR4.

Clause 23

The method of any one of clauses 1-22, wherein the BMSCs are targeted to one or more injured neurons, inflamed dorsal root ganglia (DRGs), or a combination thereof.

Clause 24

The method of any one of clauses 1-22, wherein the BMSCs are targeted to one or more dorsal root ganglia (DRGs) with injured axons, inflamed DRGs, or a combination thereof.

Clause 25

The method any one of clauses 1-24, wherein axons in the subject are protected from injury.

Clause 26

The method of any one of clauses 1-25, wherein after administration of the composition, the BMSCs migrate to dorsal root ganglions (DRGs) expressing CXCL12.

Clause 27

The method of clause 26, wherein after migration, the BMSCs are localized at an edge or surrounding membrane of the dorsal root ganglia (DRGs), spinal cord, or a combination thereof.

Clause 28

The method of any one of clauses 1-27, wherein after administration of the composition, the BMSCs are present in the subject for at least about 1 day.

Clause 29

The method of clause 28, wherein after administration of the composition, the BMSCs are present in the subject for at least about 1 week.

Clause 30

The method of clause 29, wherein after administration of the composition, the BMSCs are present in the subject for at least about 1 month.

Clause 31

The method of any one of clauses 1-30, wherein the BMSCs are tolerated by an immune system of the subject.

Clause 32

The method of any one of clauses 1-31, wherein the method further comprises administering to the subject a composition comprising TGF-β1.

Clause 33

The method of clause 32, wherein the composition comprising TGF-β1 is administered by injection.

Clause 34

The method of clause 33, wherein the composition comprising TGF-β1 is administered by intrathecal injection

Clause 35

The method of clause 33, wherein the composition comprising TGF-β1 is administered by direct injection into the dorsal root ganglia.

Clause 36

The method of any one of clauses 1-31, wherein the composition further comprises TGF-β1.

Clause 37

A method of treating pain in a subject in need thereof, the method comprising administering to the subject a composition comprising bone marrow stromal cells (BMSCs) and TGF-β1.

Clause 38

The method of clause 32, wherein the composition is administered by injection.

Clause 39

The method of clause 38, wherein the composition is administered by intrathecal injection.

Clause 40

The method of clause 38, wherein the composition is administered by direct injection into the dorsal root ganglia.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method of treating pain in a subject in need thereof, the method comprising administering to the subject a composition comprising a homogeneous population of bone marrow stromal cells (BMSCs);
wherein the BMSCs secrete TGF-µ1 and express CXCR4 and do not differentiate into another cell type after administration of the BMSCs to the subject; and,
wherein the composition is administered by a single intrathecal injection.

2. The method of claim 1, wherein the pain comprises neuropathic pain, inflammatory pain, cancer pain, or a combination thereof.

3. The method of claim 1, wherein the pain is chronic.

4. The method of claim 1, wherein the BMSCs are autologous BMSCs, heterologous BMSCs, or a combination thereof.

5. The method of claim 1, wherein the BMSCs are derived from a cell line, a donor subject, or a combination thereof.

6. The method of claim 1, wherein at least $0.5 \times 10^5$ BMSCs are administered to the subject.

7. The method of claim 1, wherein the pain is reduced or suppressed in the subject for at least 30 minutes as compared to an untreated subject.

8. The method of claim 1, wherein the BMSCs are targeted to one or more injured neurons, inflamed dorsal root ganglia (DRGs), or a combination thereof.

9. The method of claim 1, wherein axons in the subject are protected from injury.

10. The method of claim 1, wherein after administration of the composition, the BMSCs migrate to dorsal root ganglions (DRGs) expressing CXCL12.

11. The method of claim 1, wherein after administration of the composition, the BMSCs are present in the subject for at least 1 day.

12. The method of claim 1, wherein the BMSCs are tolerated by an immune system of the subject.

13. The method of claim 1, wherein the method further comprises administering to the subject a composition comprising TGF-µ1.

14. The method of claim 13, wherein the composition comprising TGF-µ1 is administered by injection.

15. The method of claim 1, wherein the composition further comprises TGF-µ1.

16. A method of treating pain in a subject in need thereof, the method comprising administering to the subject a composition comprising a homogeneous population of bone marrow stromal cells (BMSCs) and TGF-µ1;
wherein the BMSCs secrete TGF-µ1 and express CXCR4 and do not differentiate into another type of cell after administration of the BMSCs to the subject; and,
wherein the composition is administered by a single intrathecal injection.

17. The method of claim 1, wherein $0.5 \times 10^5$ to $9.5 \times 10^5$ BMSCs are administered to the subject.

18. The method of claim 1, wherein the BMSCs are modified to express higher levels of CXCR4 than unmodified BMSCs.

19. The method of claim 16, wherein $0.5 \times 10^5$ to $9.5 \times 10^5$ BMSCs are administered to the subject.

20. The method of claim 16, wherein the BMSCs are modified to express higher levels of CXCR4 than unmodified BMSCs.

21. The method of claim 1, wherein the BMSCs do not differentiate into another cell type 28 days after administration of the BMSCs to the subject.

22. The method of claim 16, wherein the BMSCs do not differentiate into another cell type 28 days after administration of the BMSCs to the subject.

* * * * *

UNITED STATES PATENT AND TRADEMARK OFFICE
CERTIFICATE OF CORRECTION

| | | |
|---|---|---|
| PATENT NO. | : 11,389,483 B2 | |
| APPLICATION NO. | : 15/743208 | |
| DATED | : July 19, 2022 | |
| INVENTOR(S) | : Ru-Rong Ji et al. | |

It is certified that error appears in the above-identified patent and that said Letters Patent is hereby corrected as shown below:

In the Claims

On Column 48, Claim 13, Line 5, replace "TGF-µ1" with –TGF-β1–

On Column 48, Claim 14, Line 7, replace "TGF-µ1" with –TGF-β1–

On Column 48, Claim 15, Line 9, replace "TGF-µ1" with –TGF-β1–

On Column 48, Claim 16, Line 13, replace "TGF-µ1" with –TGF-β1–

On Column 48, Claim 16, Line 14, replace "TGF-µ1" with –TGF-β1–

Signed and Sealed this
Second Day of April, 2024

*Katherine Kelly Vidal*

Katherine Kelly Vidal
*Director of the United States Patent and Trademark Office*